US009452238B2

(12) United States Patent
Thomson et al.

(10) Patent No.: US 9,452,238 B2
(45) Date of Patent: Sep. 27, 2016

(54) TISSUE IMPLANT

(75) Inventors: Brian Mark Thomson, York (GB);
Mark Frederick Smith, York (GB);
Charles William Archer, Mid Glamorgan (GB); Gary Paul Dowthwaite, Mid Glamorgan (GB)

(73) Assignee: Smith & Nephew LLP, Memphis, TN (US)

( * ) Notice: Subject to any disclaimer, the term of this patent is extended or adjusted under 35 U.S.C. 154(b) by 1299 days.

(21) Appl. No.: 10/333,973

(22) PCT Filed: Jul. 30, 2001

(86) PCT No.: PCT/GB01/03463
§ 371 (c)(1),
(2), (4) Date: Aug. 26, 2003

(87) PCT Pub. No.: WO02/10348
PCT Pub. Date: Feb. 7, 2002

(65) Prior Publication Data
US 2004/0033212 A1 Feb. 19, 2004

(30) Foreign Application Priority Data

Jul. 29, 2000 (GB) .................................. 0018583.5
Oct. 24, 2000 (GB) .................................. 0025939.0
Jul. 11, 2001 (GB) .................................. 0116885.5
Jul. 11, 2001 (GB) .................................. 0116886.3
Jul. 11, 2001 (GB) .................................. 0116888.9

(51) Int. Cl.
*A61F 2/28* (2006.01)
*A01N 63/00* (2006.01)
*C12N 5/00* (2006.01)
*A61L 27/38* (2006.01)
*C12N 5/077* (2010.01)
*C12N 5/0775* (2010.01)
*C12N 5/071* (2010.01)
*A61F 2/30* (2006.01)
*A61K 35/12* (2015.01)

(52) U.S. Cl.
CPC ........ *A61L 27/3817* (2013.01); *A61L 27/3852* (2013.01); *C12N 5/0068* (2013.01); *C12N 5/0655* (2013.01); *C12N 5/0662* (2013.01); *C12N 5/0697* (2013.01); *A61F 2/30756* (2013.01); *A61F 2002/30766* (2013.01); *A61K 35/12* (2013.01); *A61L 2430/06* (2013.01); *C12N 2501/15* (2013.01); *C12N 2501/39* (2013.01); *C12N 2501/42* (2013.01); *C12N 2501/585* (2013.01); *C12N 2502/1317* (2013.01); *C12N 2502/1358* (2013.01); *C12N 2502/1394* (2013.01); *C12N 2509/00* (2013.01); *C12N 2533/50* (2013.01); *C12N 2533/52* (2013.01)

(58) Field of Classification Search
CPC C12N 5/0655; C12N 5/0662; C12N 5/0697; C12N 2501/42; C12N 2501/585; C12N 2502/1358; C12N 2533/50; A61L 27/3817; A61L 2430/06; A61F 2/30756; A61F 2002/30766
USPC ........................ 623/23.63; 424/93.7; 435/325
See application file for complete search history.

(56) References Cited

U.S. PATENT DOCUMENTS

| | | | |
|---|---|---|---|
| 5,326,357 A | 7/1994 | Kandel | |
| 5,736,372 A | 4/1998 | Vacanti et al. | |
| 5,786,217 A | 7/1998 | Tubo et al. | |
| 5,904,717 A | 5/1999 | Brekke et al. | |
| 5,962,325 A | 10/1999 | Naughton et al. | |
| 6,051,750 A | 4/2000 | Bell | |
| 6,426,088 B1 * | 7/2002 | Piechaczyk et al. | 424/451 |

FOREIGN PATENT DOCUMENTS

| | | | |
|---|---|---|---|
| WO | WO 97/30662 | * 8/1997 | ............... A61F 2/30 |
| WO | WO 9730662 | 8/1997 | |
| WO | WO 0029552 | 5/2000 | |

OTHER PUBLICATIONS

Cooper et al., Alloantibody and xenoantibody cross-reactivity in transplantation. Transplantation 77(1): 1-5, 2004.*
Tew et al., Differences in repair responses between immature and mature cartilage. Clin Orthop Relat Res. 391 (Suppl): S142-52, 2001.*
Dowthwaite et al., The surface of articular cartilage contains a progenitor cell population. J Cell Sci. 117(Pt 6): 889-97, 2004.*
Schreiber et al. A method for tissue engineering of cartilage by cell seeding on bioresorbable scaffolds. Ann N Y Acad Sci. 875:398-404, 1999 (one page abstract).*
Grande et al. Evaluation of matrix scaffolds for tissue engineering of articular cartilage grafts. J Biomed Mater Res. 34(2): 211-20, 1997.*

(Continued)

*Primary Examiner* — Shin Lin Chen
(74) *Attorney, Agent, or Firm* — Smith & Nephew LLP; Joseph M. Maraia

(57) ABSTRACT

An implant, artificial or semi-artificial at implantation, for repairing an articular cartilage and osteochondral defect site in a mammalian, such as a human. The implant having at least a first surface and a second surface. The first surface shaped for being press-fitted into the defect site to create an interface between the first surface and a bone-cartilage region of the defect site, and the second surface shaped for being press-fitted into the defect site to create an interface between the second surface and an articular cartilage region of the defect site. The implant being seeded, prior to implantation, with chondroprogenitor cells, including superficial zone chondroprogenitor cells.

17 Claims, 35 Drawing Sheets

(56) References Cited

OTHER PUBLICATIONS

Schreiber et al. A method for tissue engineering of cartilage by cell seeding on bioresorbable scaffolds. Ann N Y Acad Sci. 875:398-404, 1999.*
Livne et al., Age-related changes in the role of matrix vesicles in the mandibular condylar cartilage, J. Anat. 150:61-74, 1987.*
Angele et al., Engineering of osteochondral tissue with bone marrow mesenchymal progenitor cells in a derivatized hyaluronan-gelatin composite sponge, Tissue Eng. 5(6):545-54, 1999.*
Alsalameh et al., 2004, Arthritis & Rheumatism, vol. 50, No. 5, pp. 1522-1532.*
De Bari et al., 2001, Arthritis & Rheumatism, vol. 44, No. 8, pp. 1928-1942.*
Caterson, et al. 'Production and characterization of monoclonal antibodies directed against connective tissue proteoglycans,' *Fed. Proc.*, 44(2):386-393 (1985).
Couchman, et al., 'Mapping by monoclonal antibody detection of glycosaminoglycans in connective tissues,' Nature, 307(5952):650-652 (1984).
Coombes and Meikle, 'Resorbable Synthetic Polymers as Replacements for Bone Graft,' *Clinical Materials*, 17:35-67 (1994).
Mankin, 'The reaction of articular cartilage to injury and osteoarthritis,' Part I, *N. Engl. J. Med.*, 291(24):1285-1292 (1974), Operative Arthroscopy, Editor-in-Chief John B. McGinty.
Mankin, 'The reaction of articular cartilage to injury and osteoarthritis,' Part II, N.Engl. J. Med., 241:1335 (1974), Operative Arthroscopy, Editor-in-Chief John B. McGinty.
Robinson, et al., 'Implants Composed of Carbon Fiber Mesh and Bone-Marrow-Derived, Chondrocyte-Enriched Cultures for Joint Surface Reconstruction,' Bulletin—Hospital for Joint Diseases, Hospital of Joint Diseases, New York, New York, 53(1):75-82 (1993).
Stockwell, 'The cell density of human articular and costal cartilage,' *J.Anat.*, 101(4):753-763 1967.
Stockwell, et al., The chondrocytes, in Freeman MAR (ed): *Adult Articular Cartilage*, ed. 2, Tunbridge Wells, Pitman Medical, 69-144 (1979).
American Academy of Orthopaedic Surgeons Symposium, Injury and Repair of the Musculoskeletal Soft Tissues, Chapter 9, Articular Cartilage: Composition and Structure, pp. 414-426 (1987) Savannah, Georgia, (Chondrocytes paragraph p. 414).
Articular Cartilage and Knee Joint Function, Basic Science and Arthroscopy, Perforation or Abrasion of Subchondral Bone paragraph, p. 4, A symposium organized by the Arthroscopy Associate of North America sponsored by Bristol-Myers/Zimmer, edited by J. Whit Ewing (1988) Chicago, Illinois, pp. 1-18.
International Search Report dated May 7, 2002 in Application No. PCT/GB2001/03463.
Ahsan, T. and Sah, R.L., "Biomechanics of integratice cartilage repair", Journal of the OsteoArthritis Research Society International, (1999), 7:29-40.
Hayato Hirotani and Tetsuo Ito, "Chrondocyte Mitosis in the Articular Cartilage of Femoral Heads With Various Diseases", Acta orthop. scand., 46, 979-986, 1975, 8 pages.
G. Lapadula et al., "Chondrocyte Phenotyping in Human Osteoarthritis", Clinical Rheumatology, 17, 99-104, 1998, 6 pages.
Mary B. Goldring, "The Role of the Chondrocyte in Osteoarthritis", Arthritis & Rheumatism, 43, No. 9, 1916-1926, 2000, 11 pages.

* cited by examiner

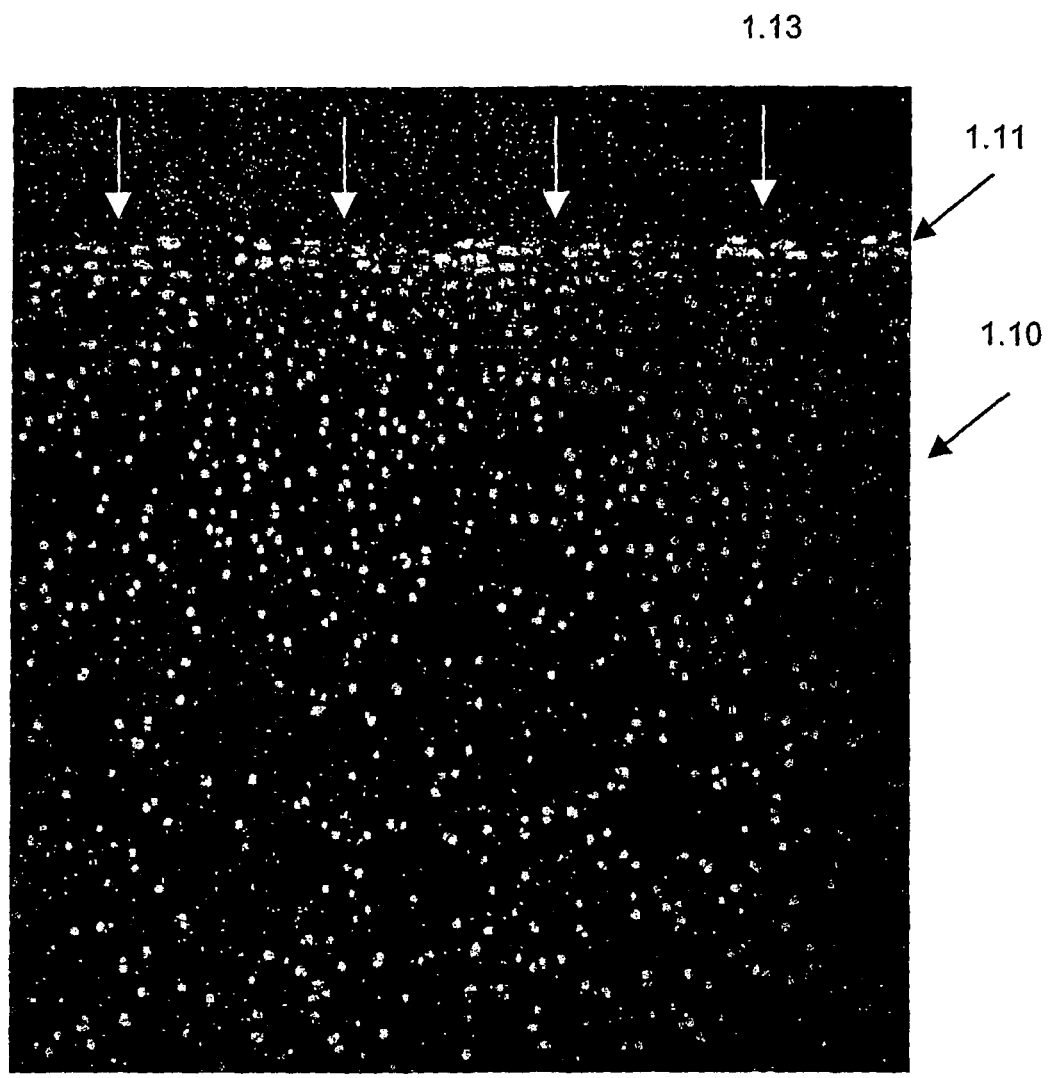
Fig. 1.1

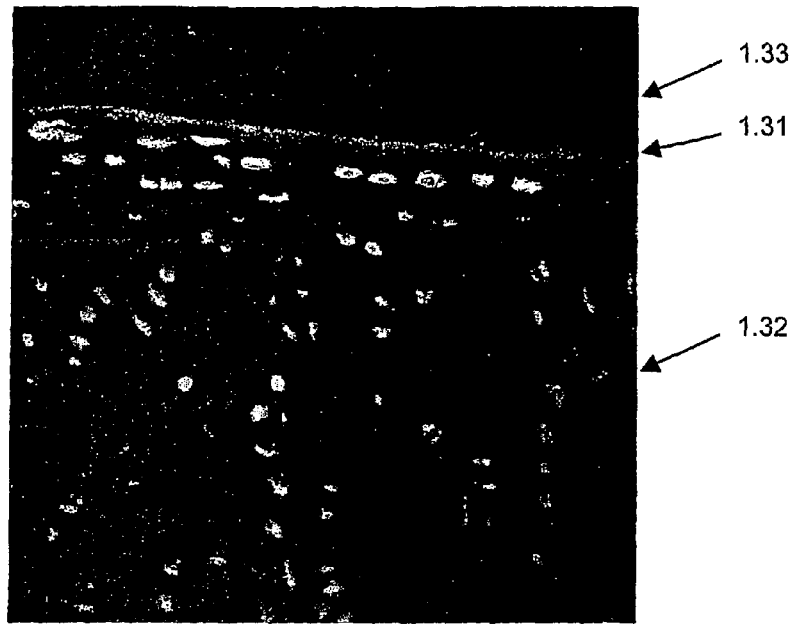
Fig. 1.3
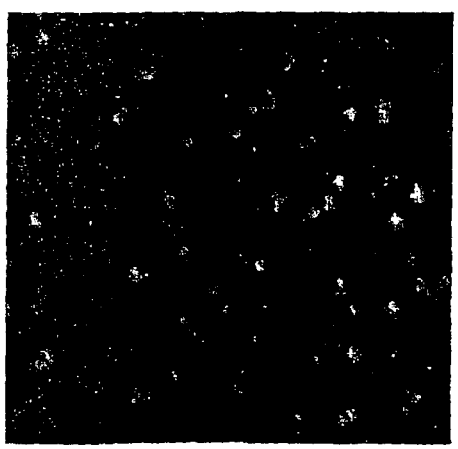
Fig. 1.4
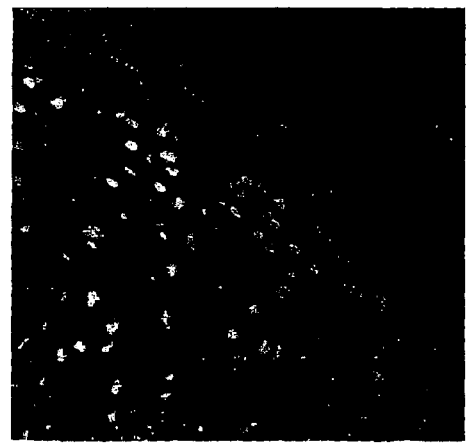
Fig. 1.5

Fig. 1.6          Fig. 1.7
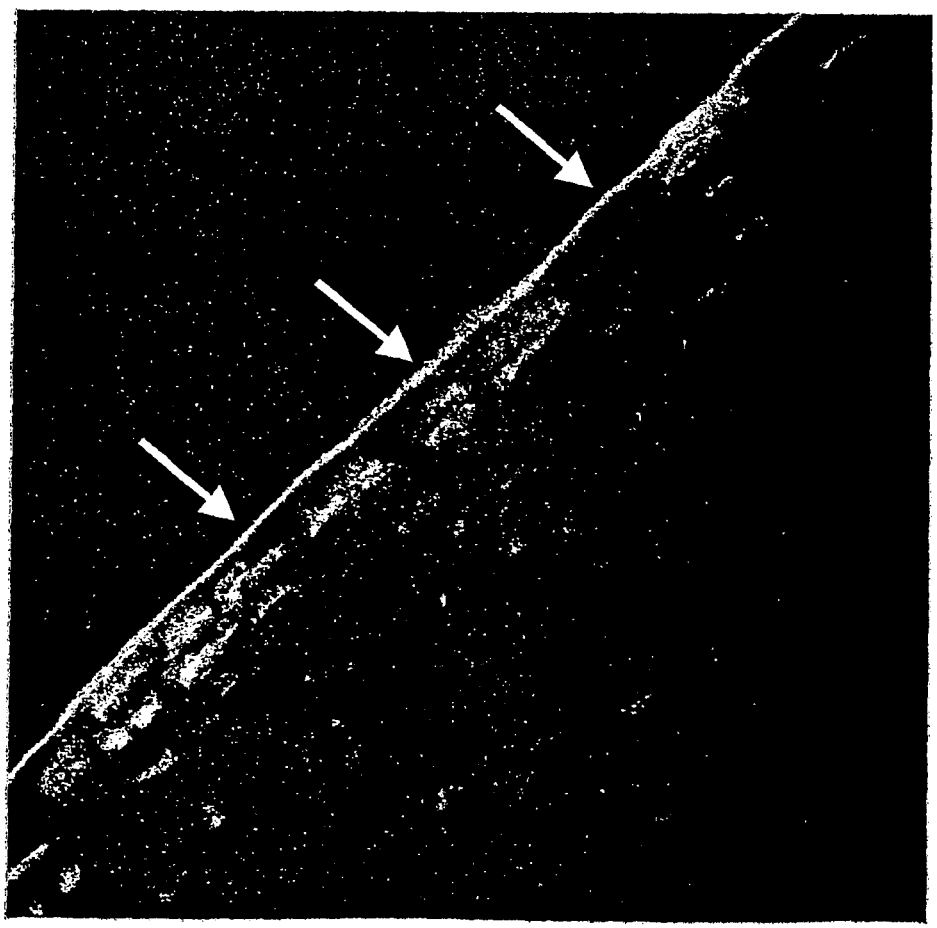
Fig. 1.8

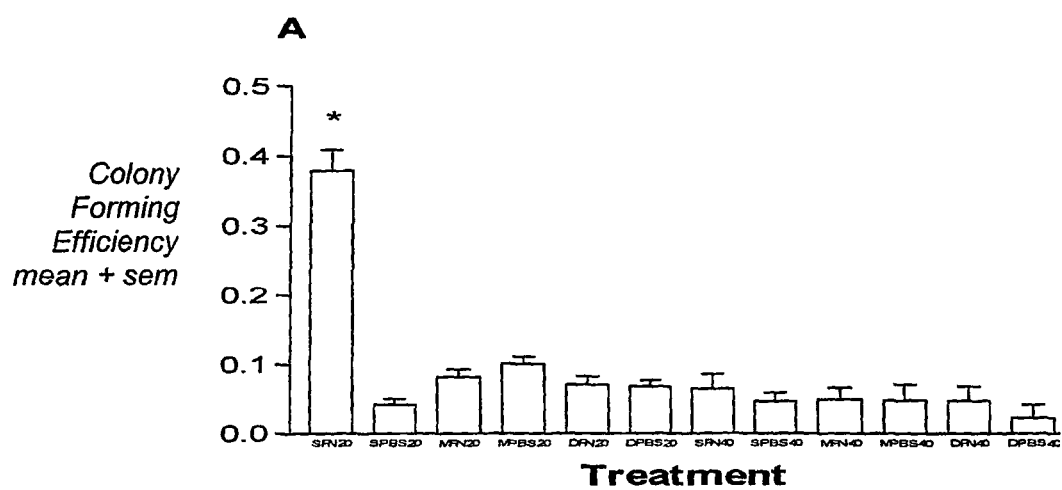
Fig. 1.9

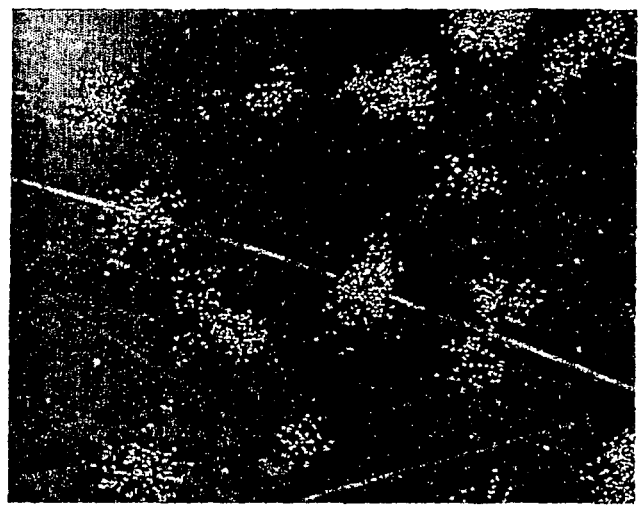
Fig. 1.10
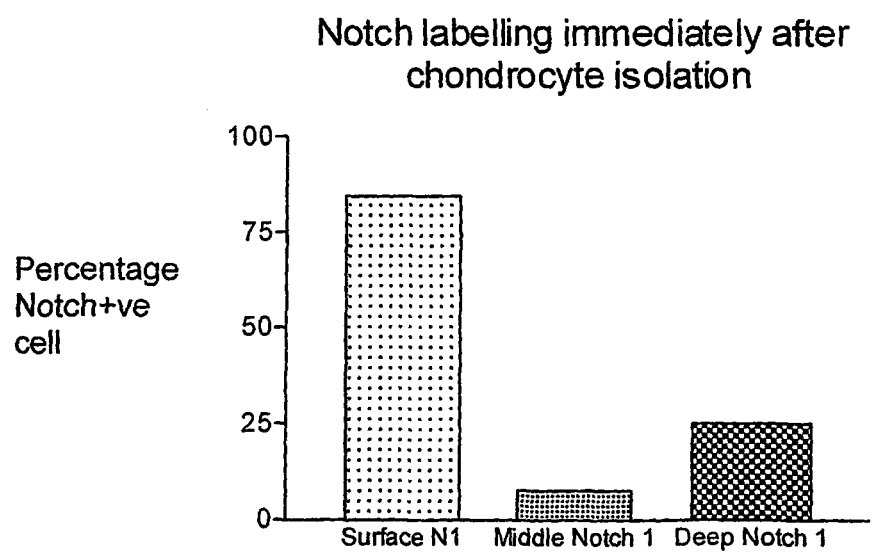
Fig. 1.11

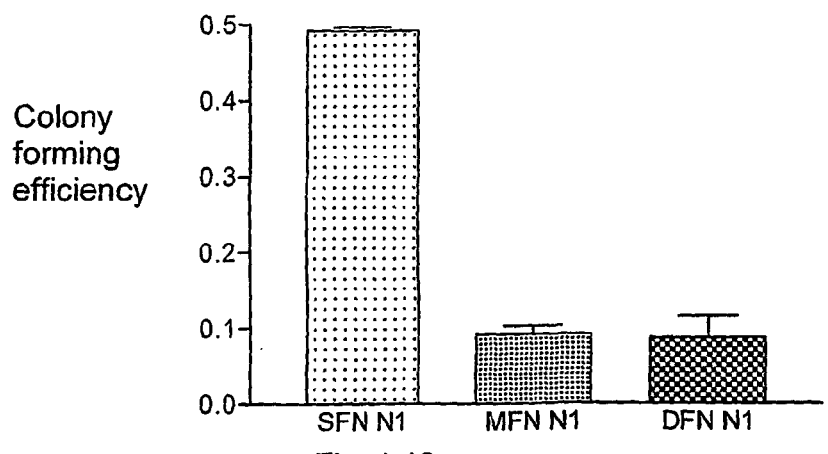
Fig. 1.12
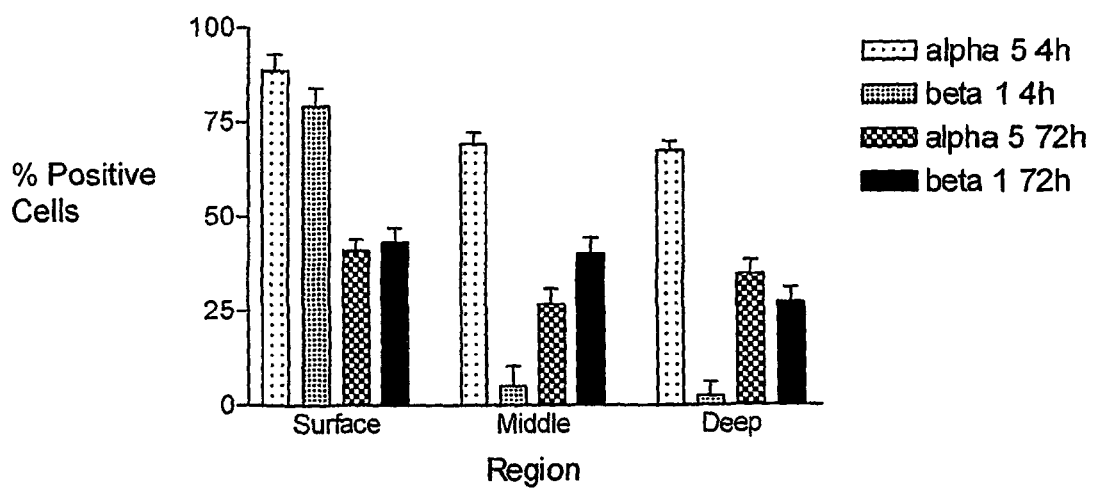
Fig. 1.13

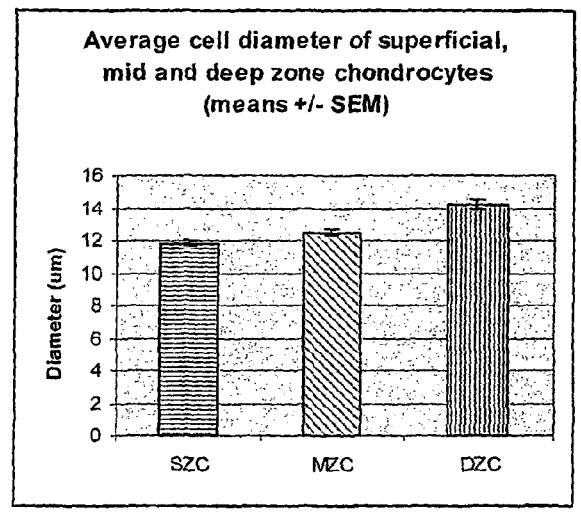
Fig. 1.14
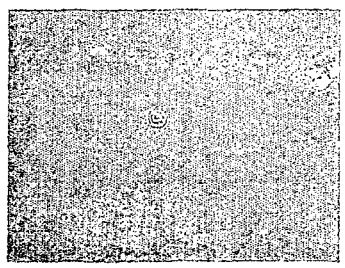 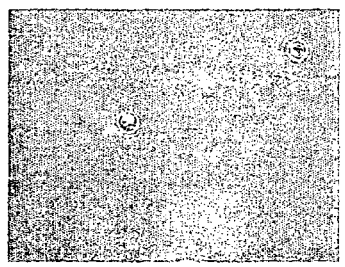 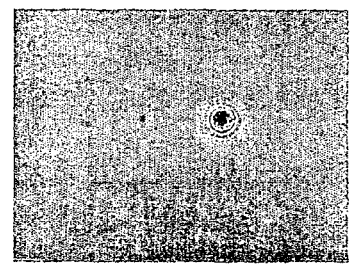
Fig. 1.15a  Fig. 1.15b  Fig. 1.15c
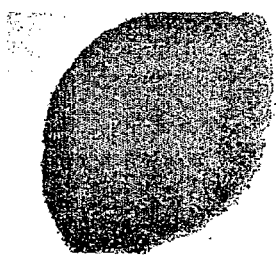 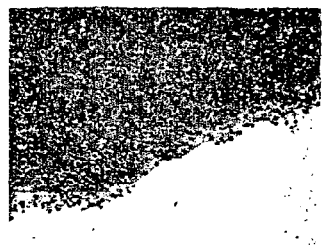
Fig. 1.16a  Fig. 1.16b

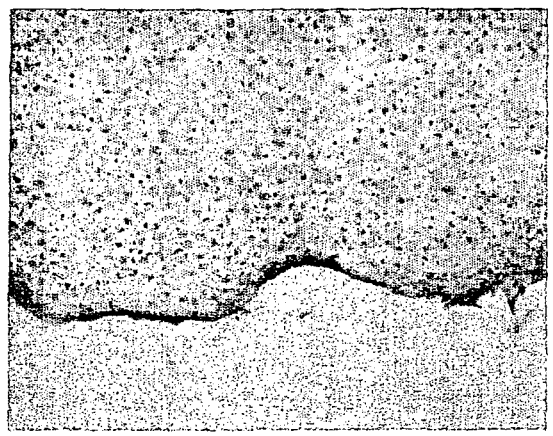
Fig. 1.17
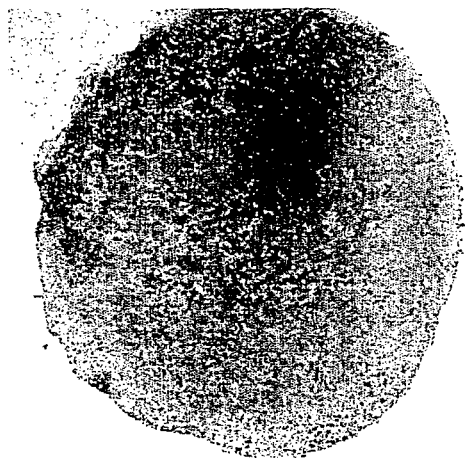
Fig. 1.18

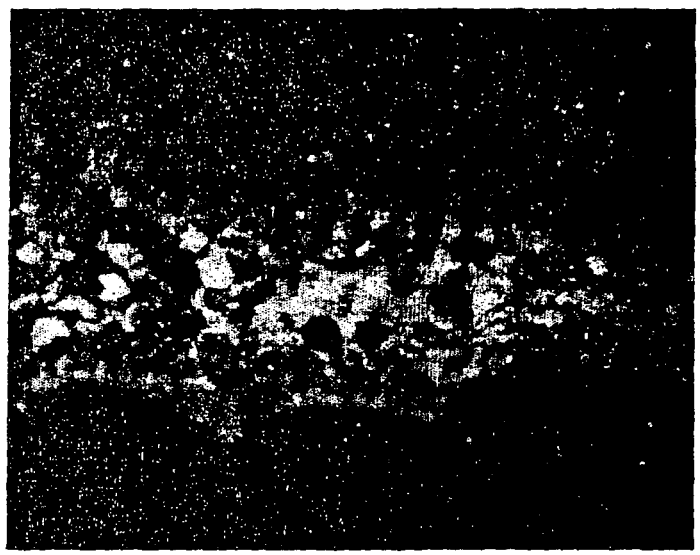
Fig. 1.19
Fig. 1.20

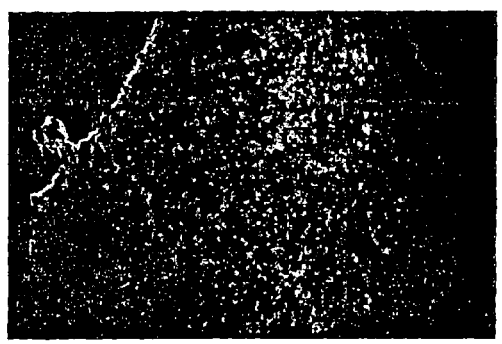
Fig. 1.21
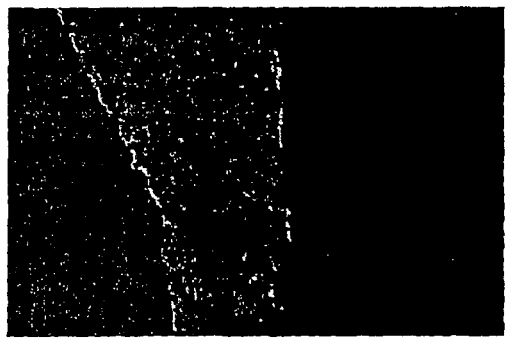
Fig. 1.22
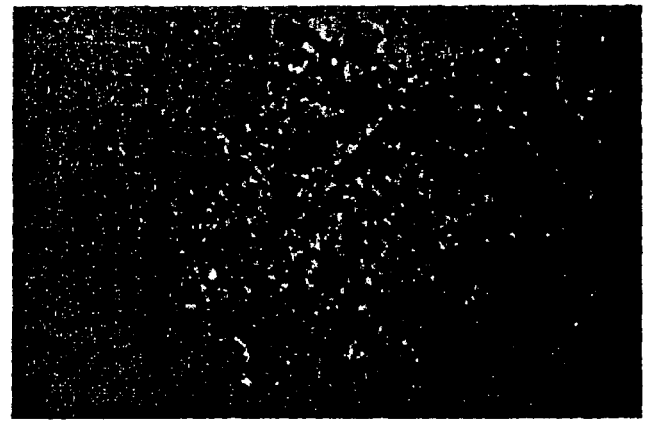
Fig. 1.23

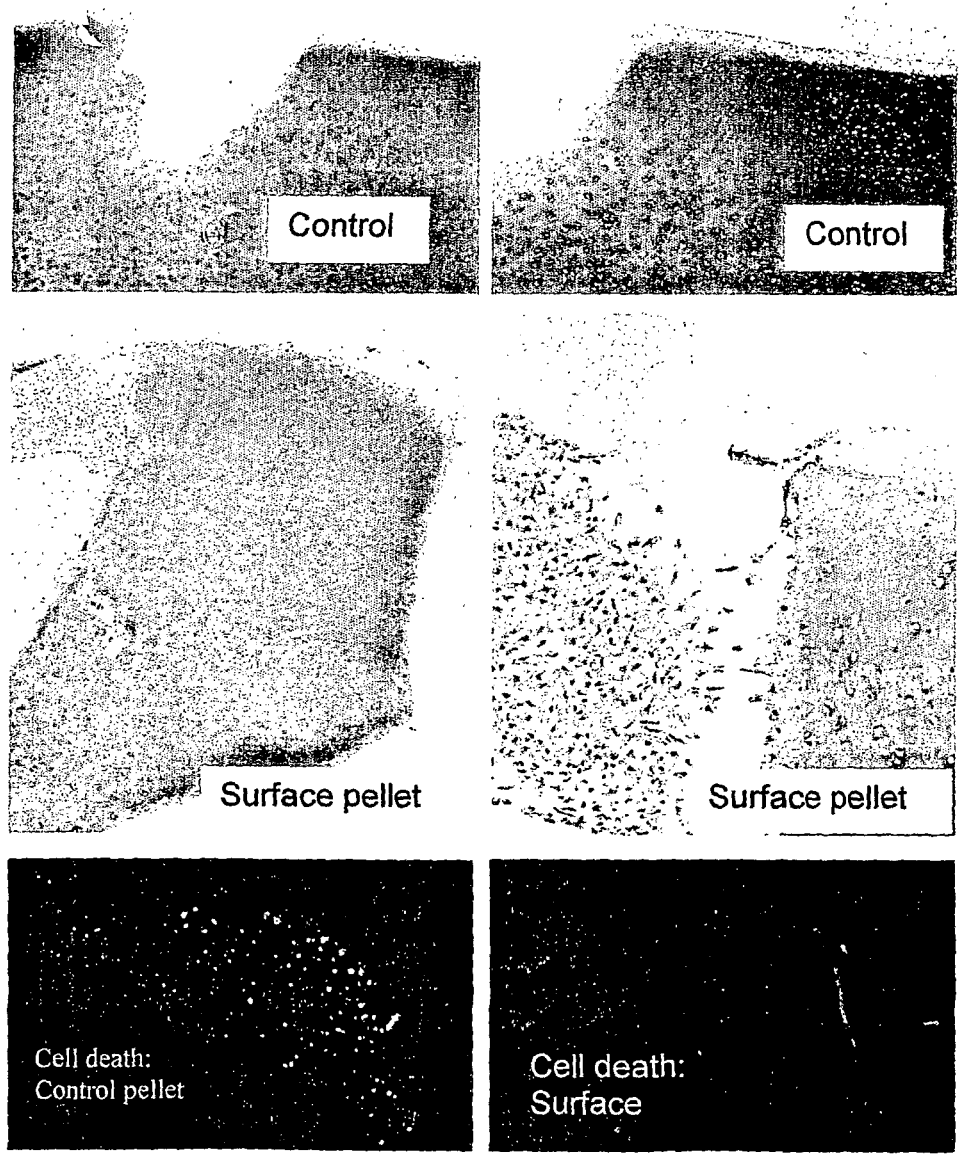
Fig. 1.24

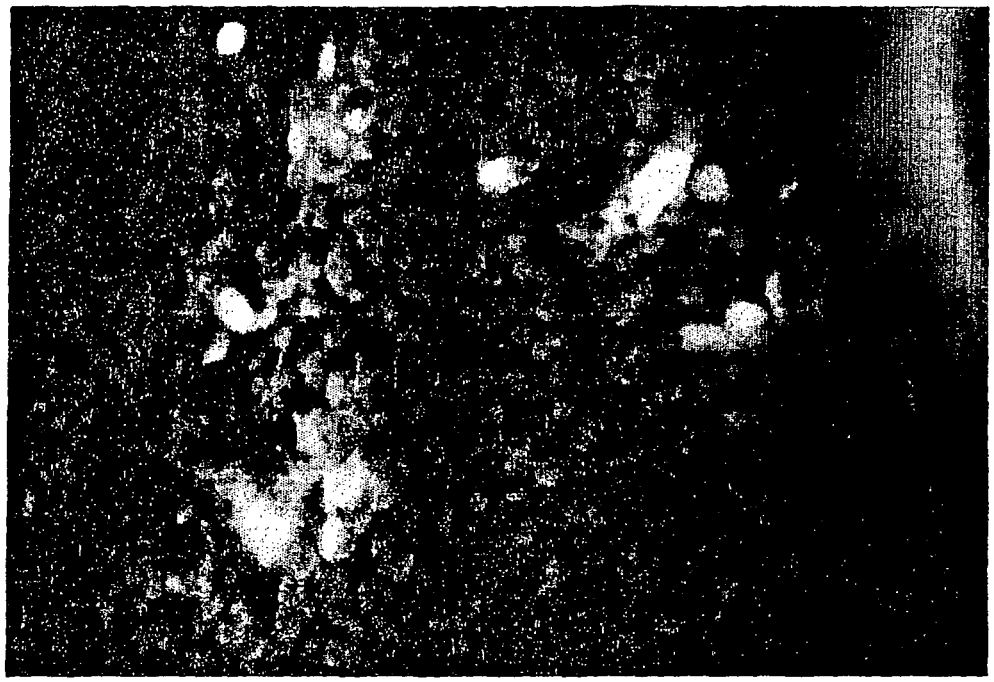
Fig. 1.25
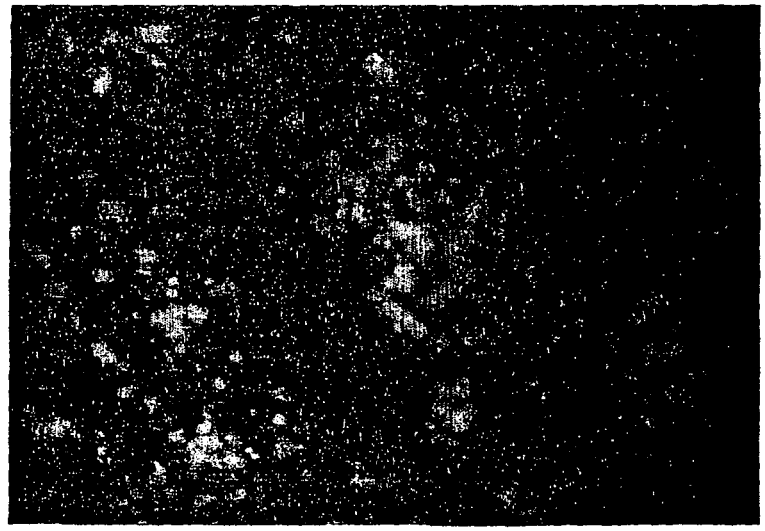
Fig. 1.26

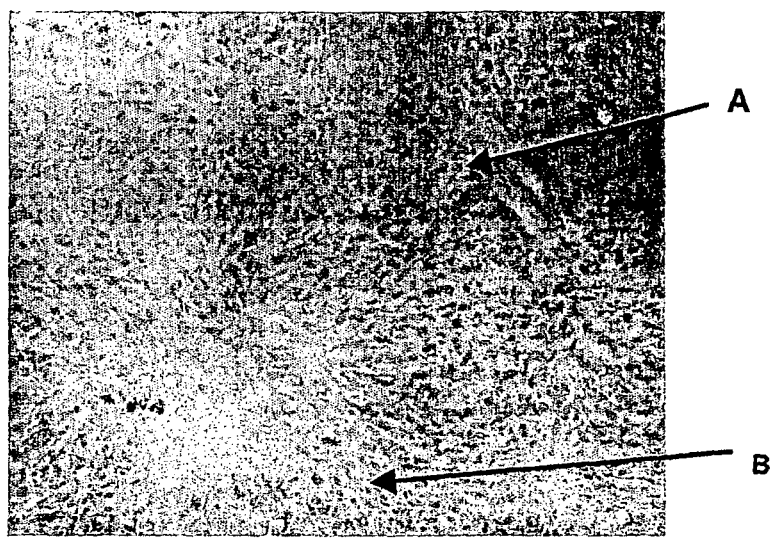
Fig. 1.27

Fig. 2.1
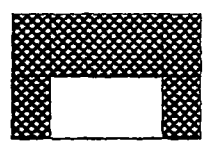
Fig. 2.2
Fig. 2.3

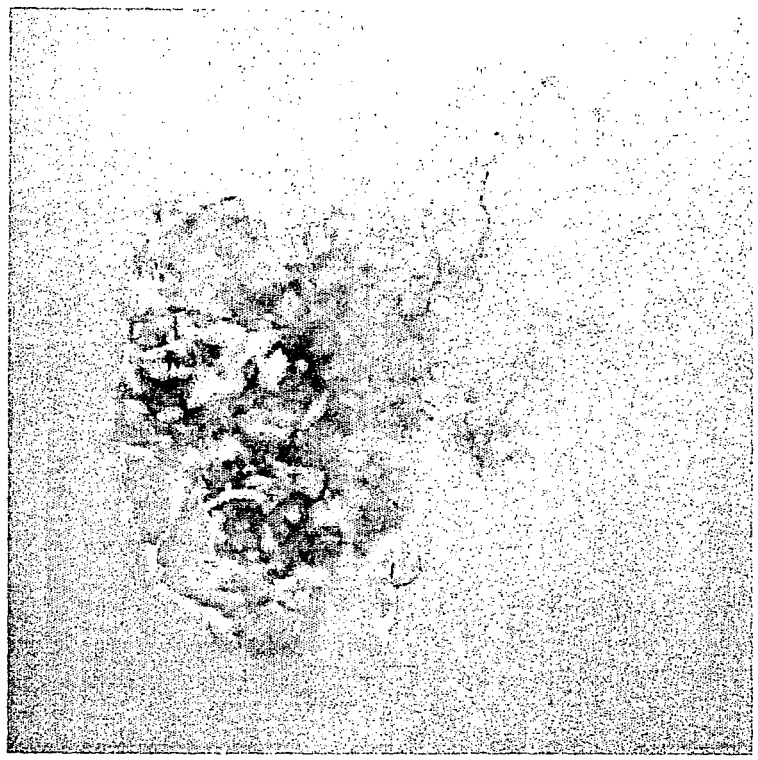
Fig. 2.4
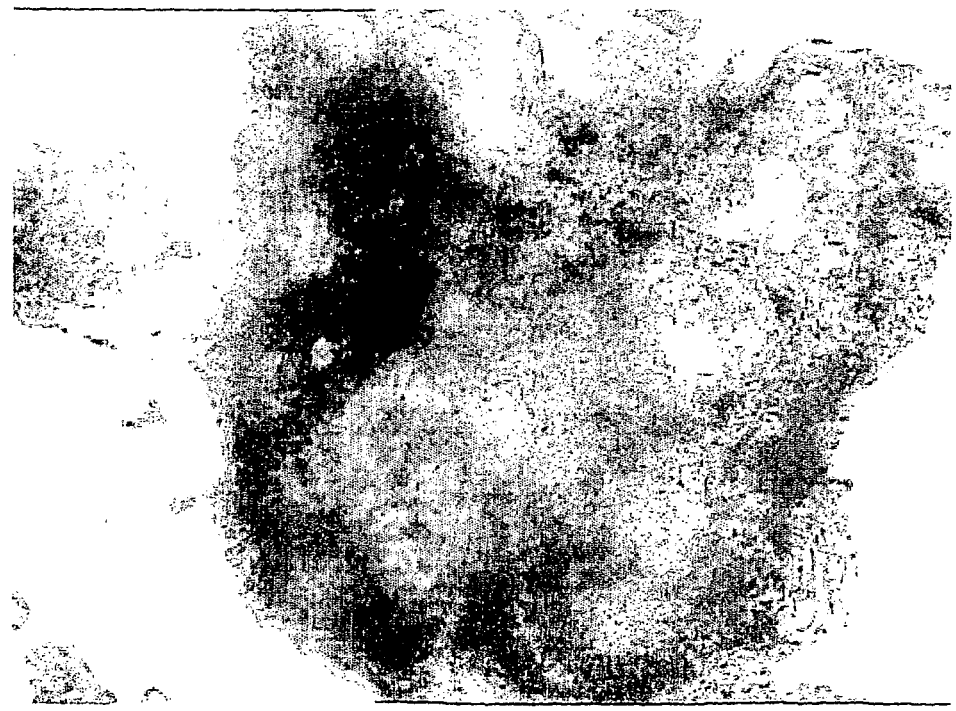
Fig. 2.5

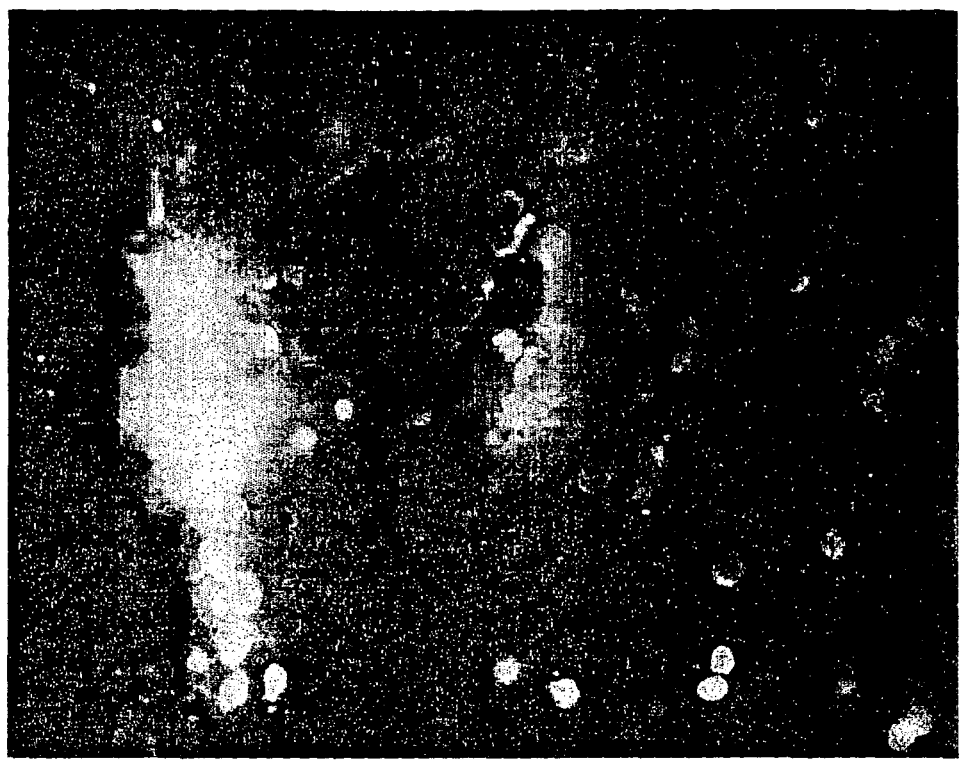
Fig. 2.6
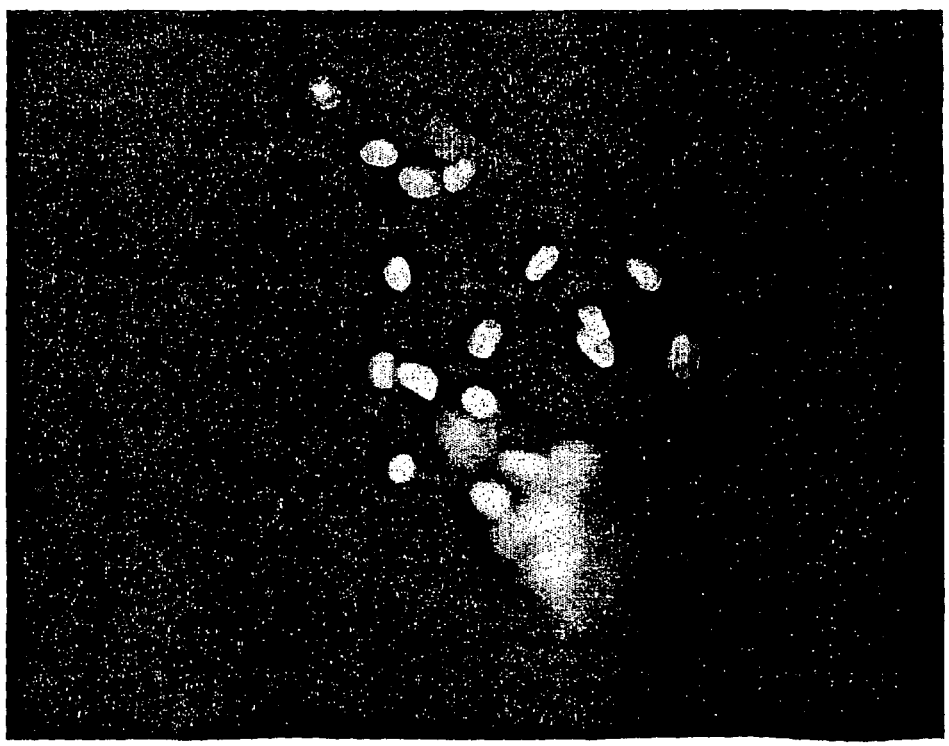
Fig. 2.7

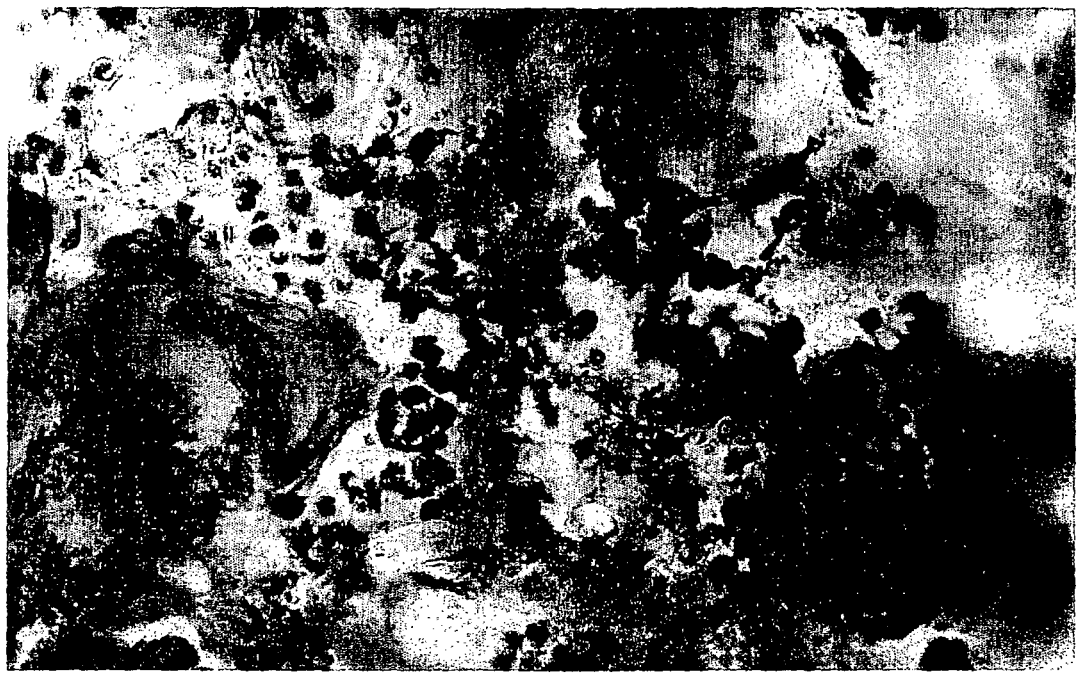
Fig. 2.8
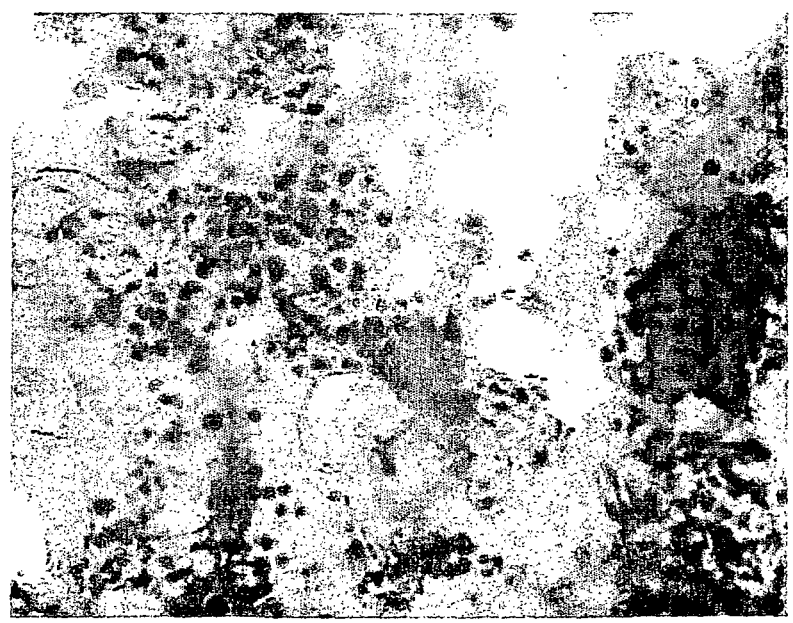
Fig. 2.9a

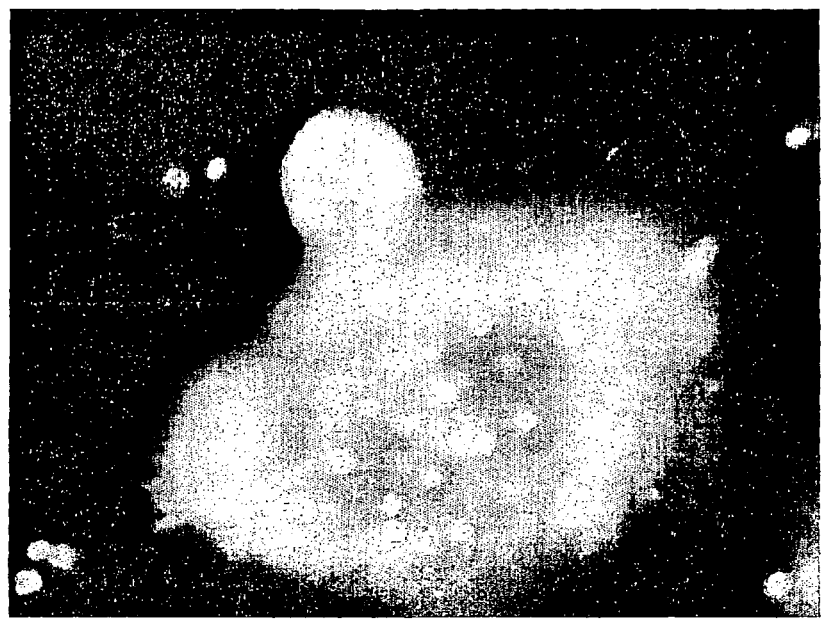
Fig. 2.9b
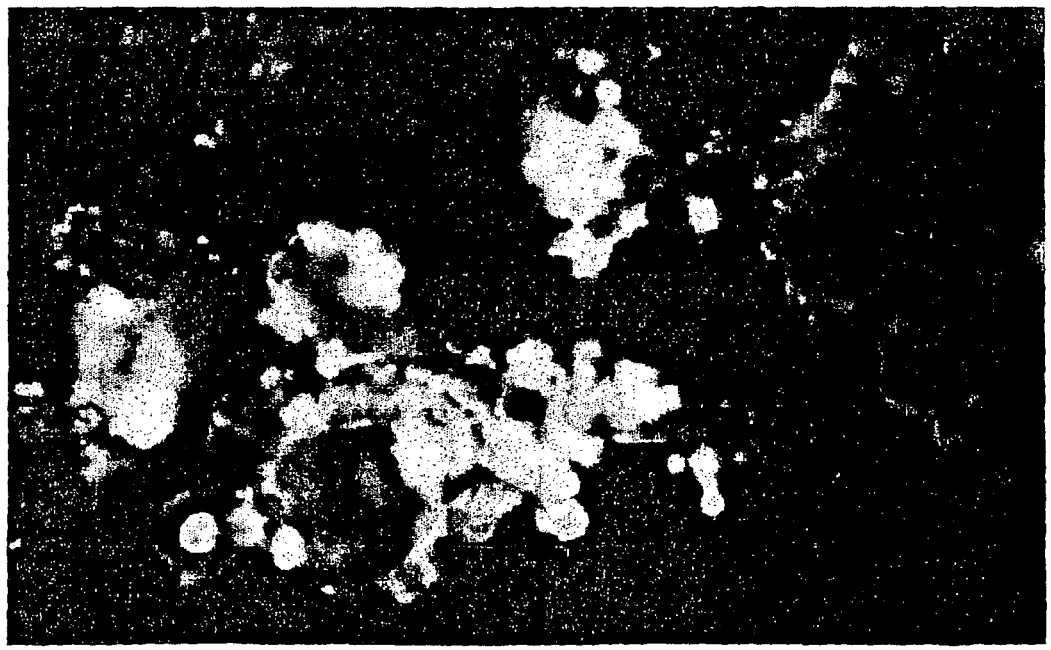
Fig. 2.10

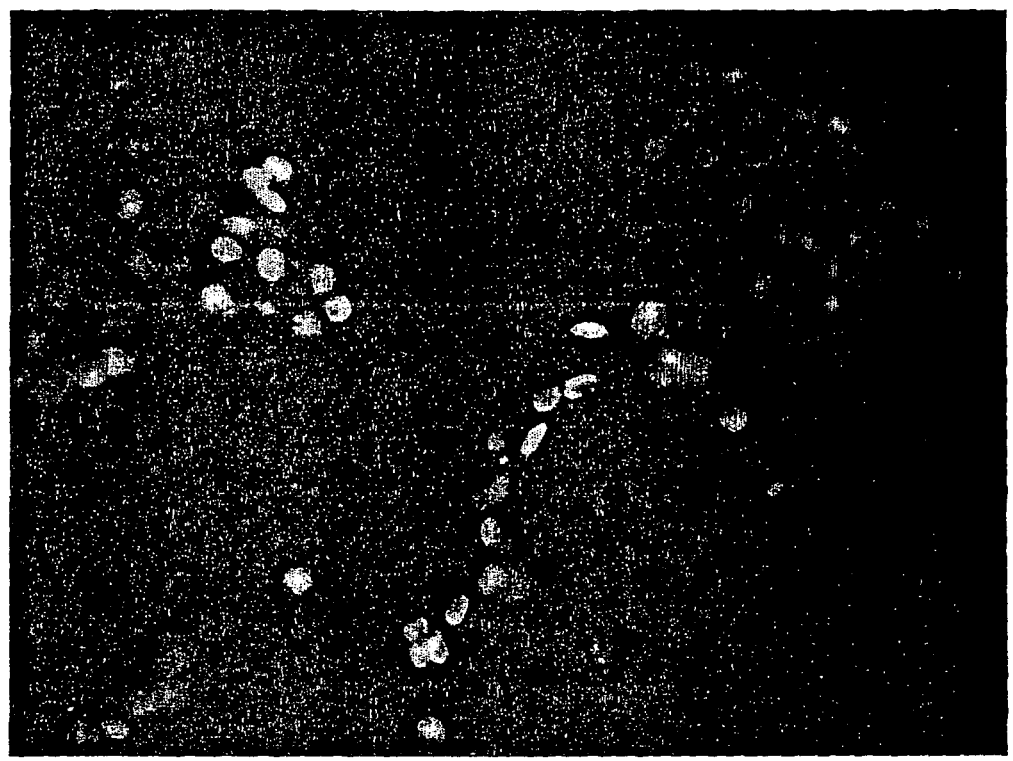
Fig. 2.11
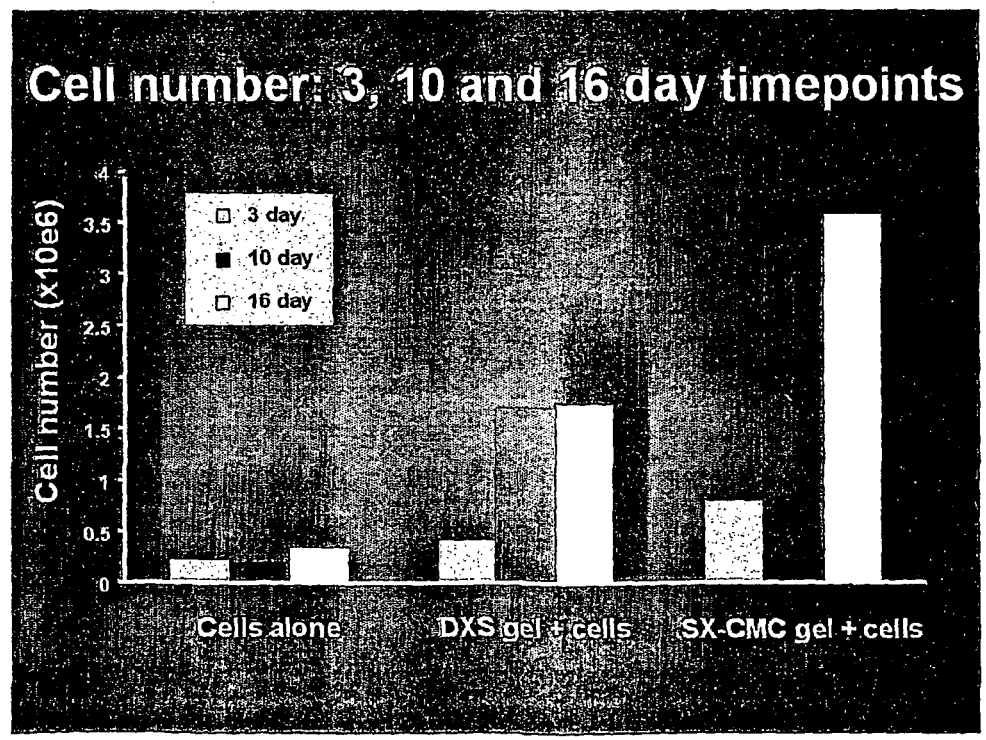
Fig. 2.12

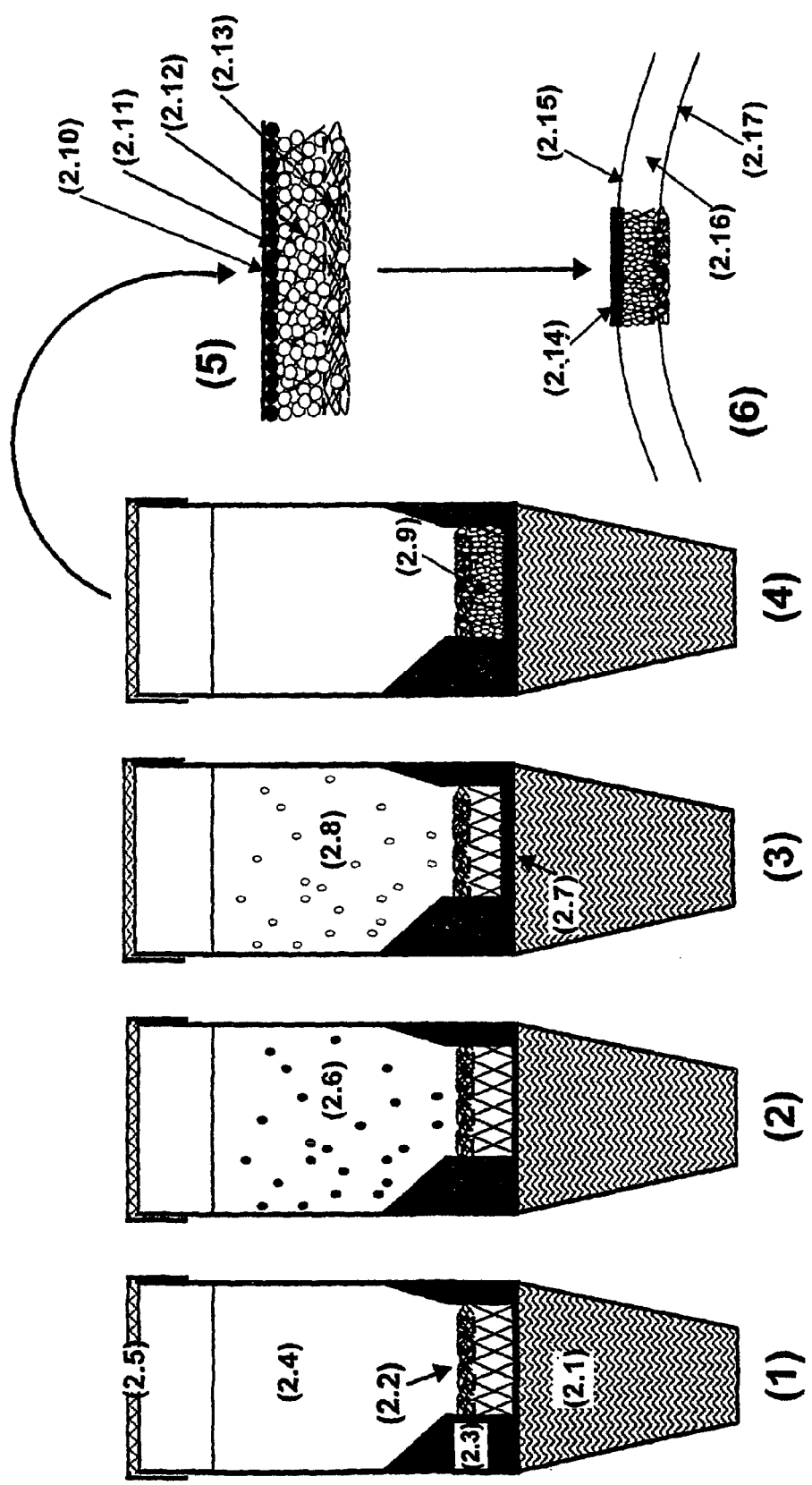
Fig. 2.13

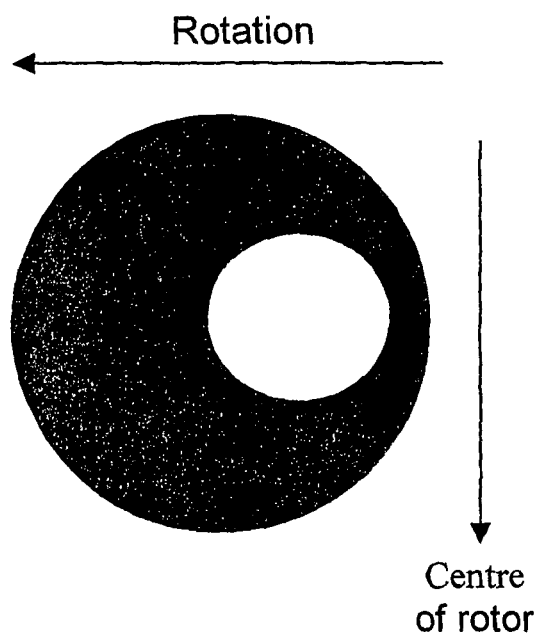
Fig. 2.14
Fig. 2.15

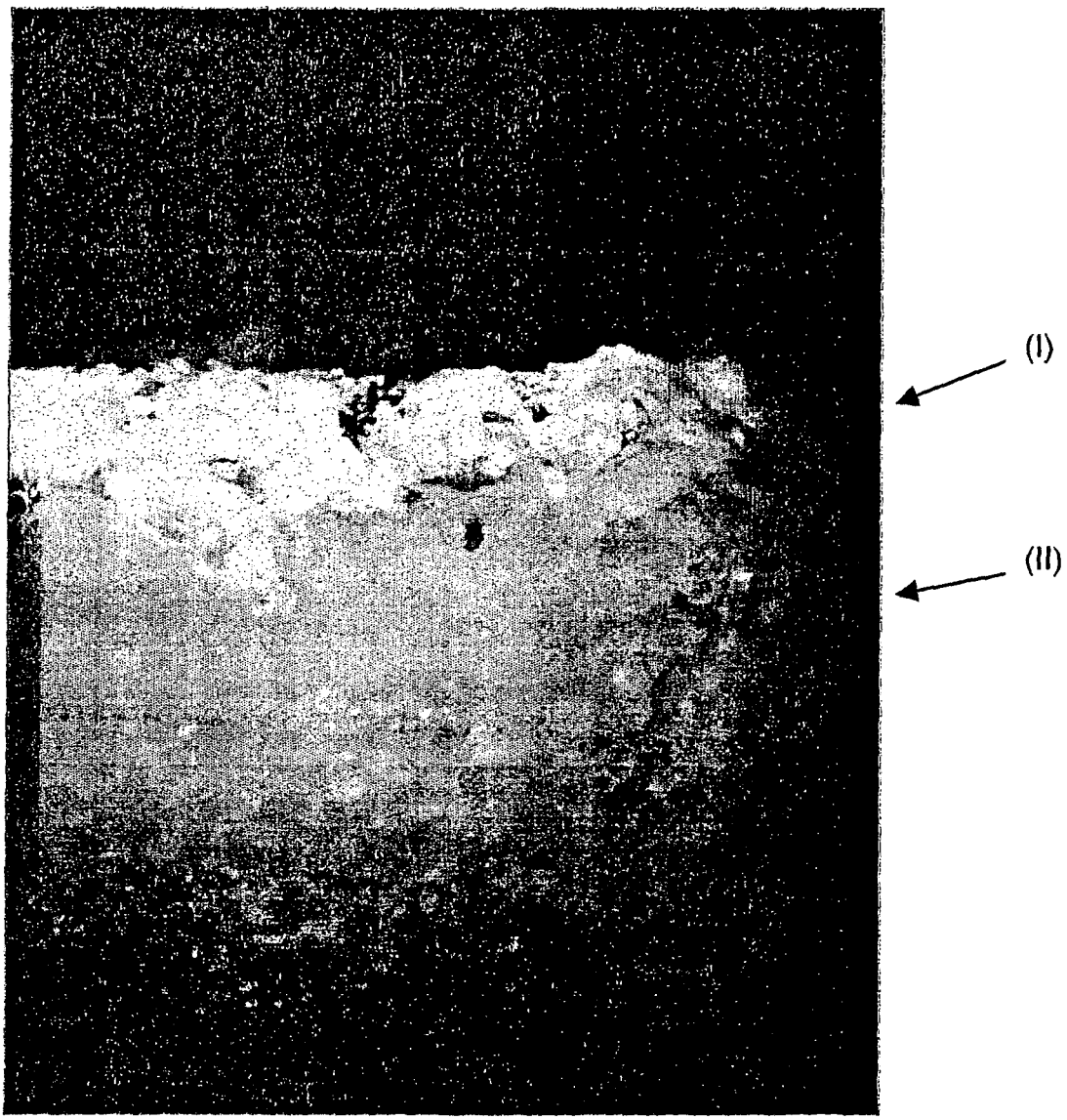
Fig. 2.16

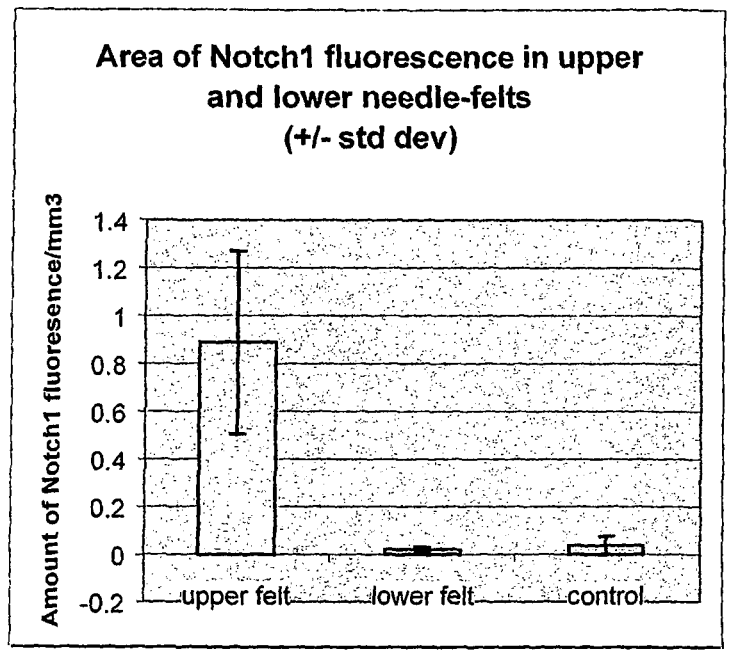
Fig. 2.17
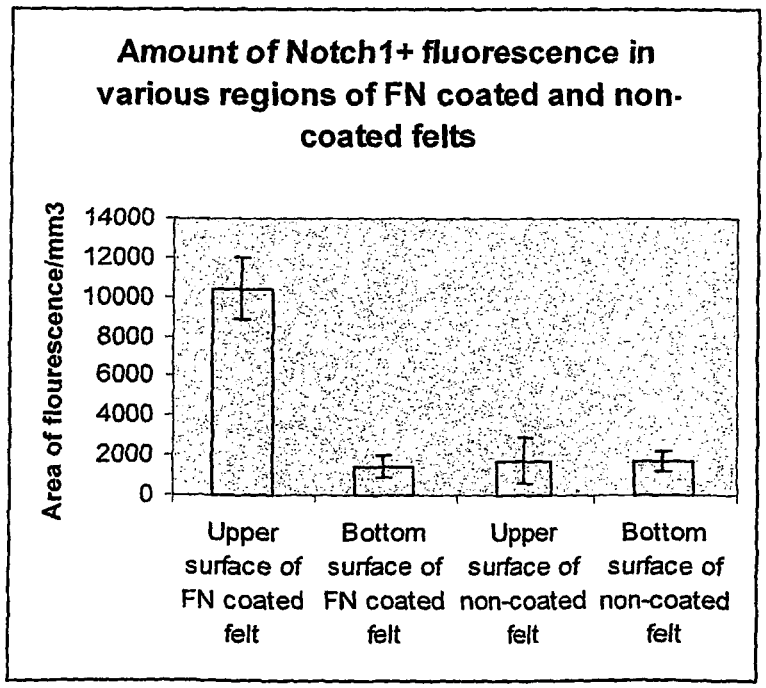
Fig. 2.18

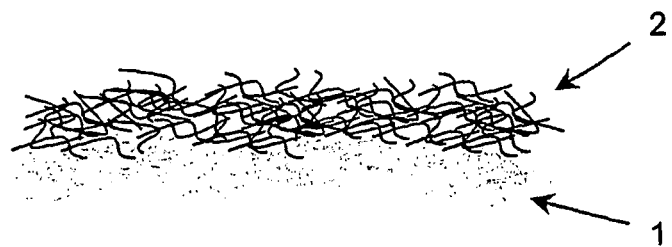
Fig. 3.1a
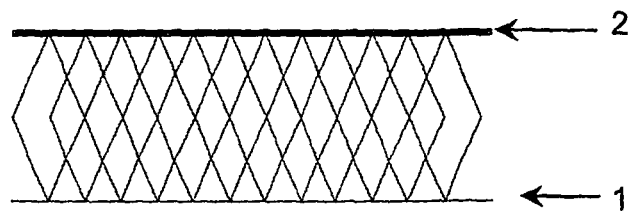
Fig. 3.1b
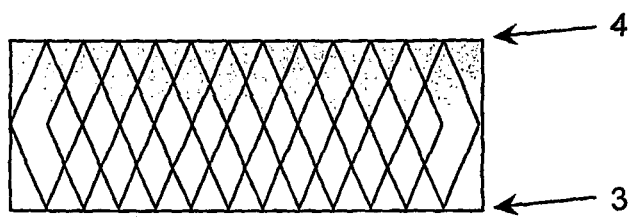
Fig. 3.1c
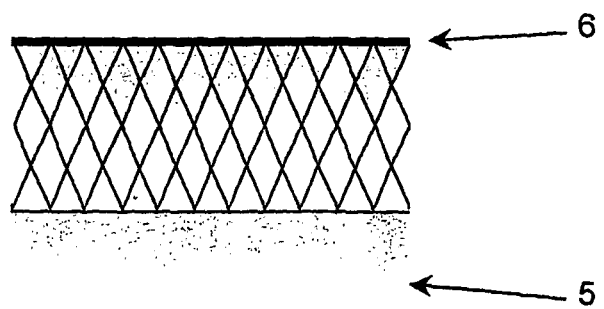
Fig. 3.1d

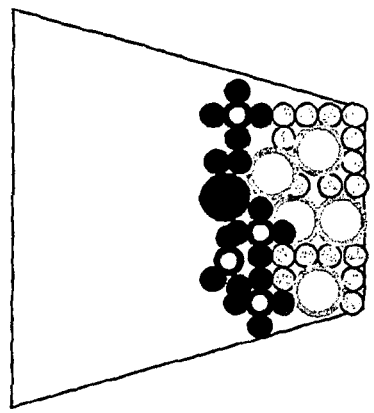
Fig. 3.2c
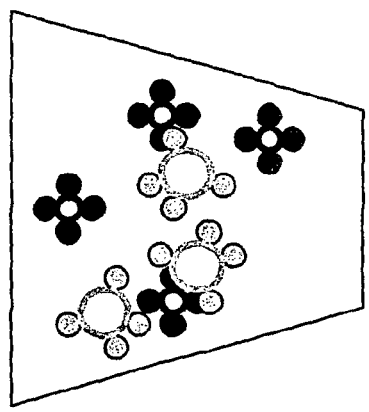
Fig. 3.2b
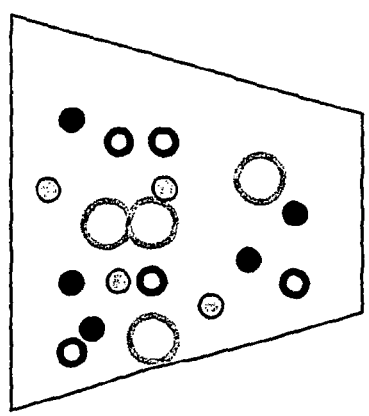
Fig. 3.2a
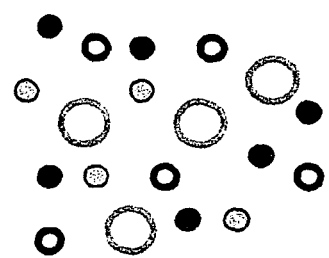
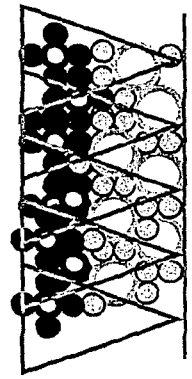
Fig. 3.3c
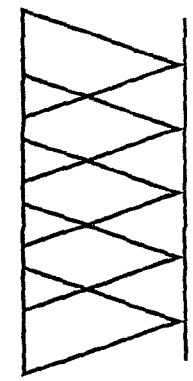
Fig. 3.3b
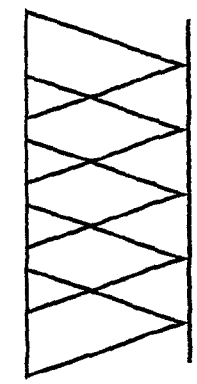
Fig. 3.3a

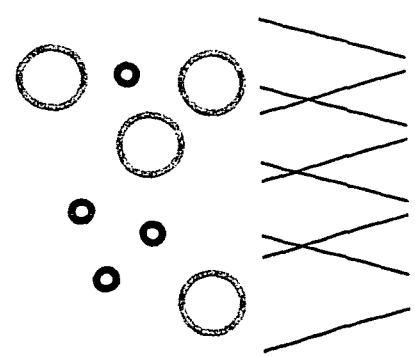
Fig. 3.4a
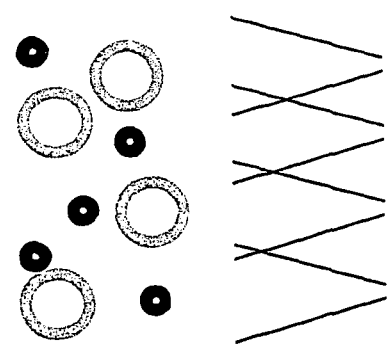
Fig. 3.4b
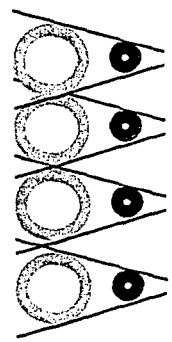
Fig. 3.4c

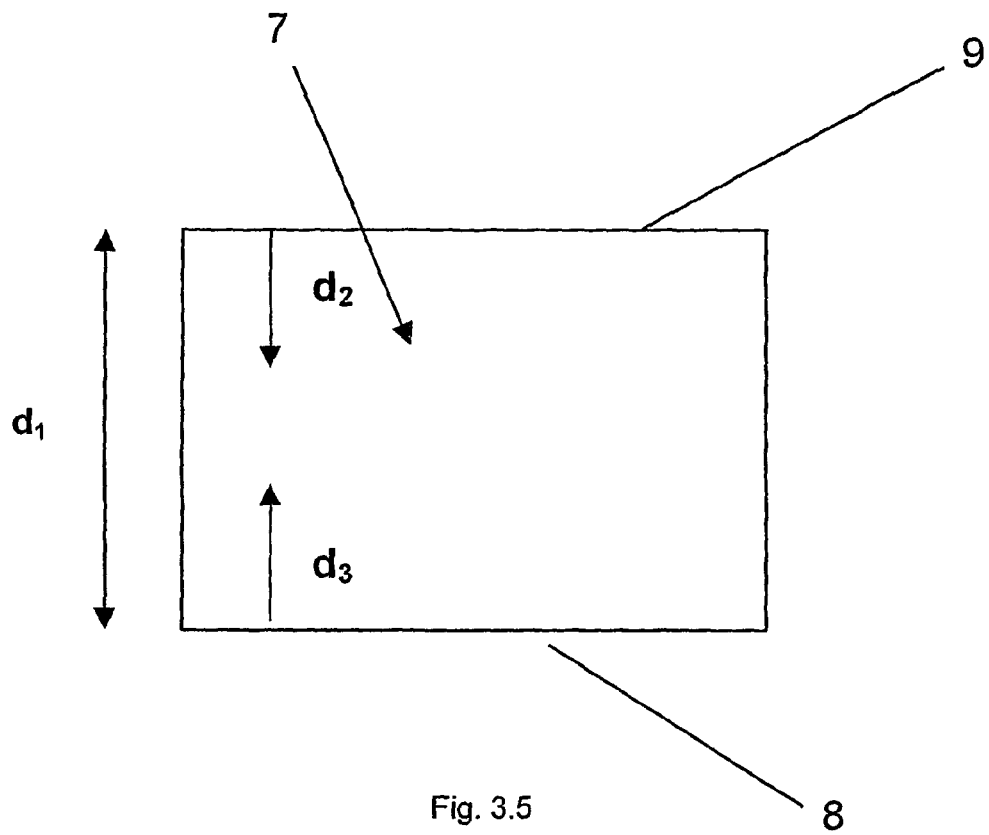
Fig. 3.5
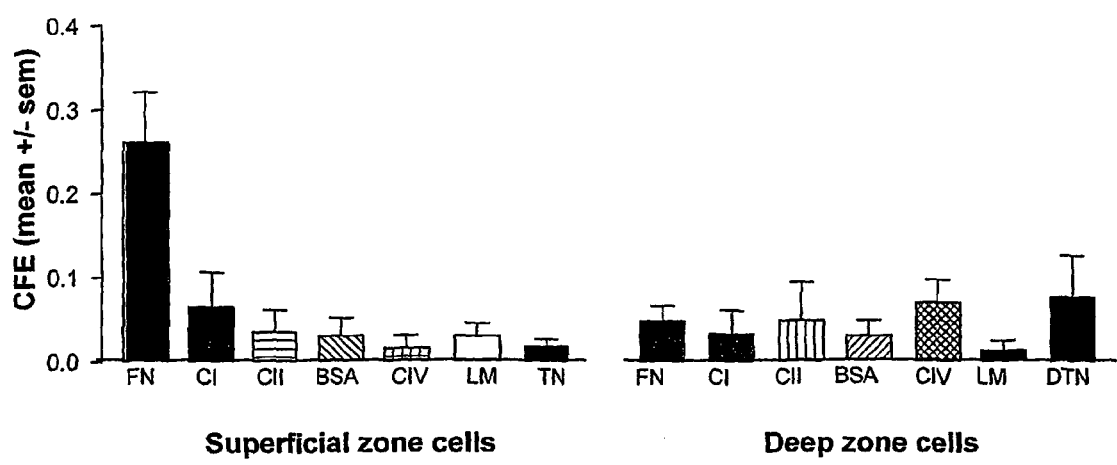
Fig. 3.6

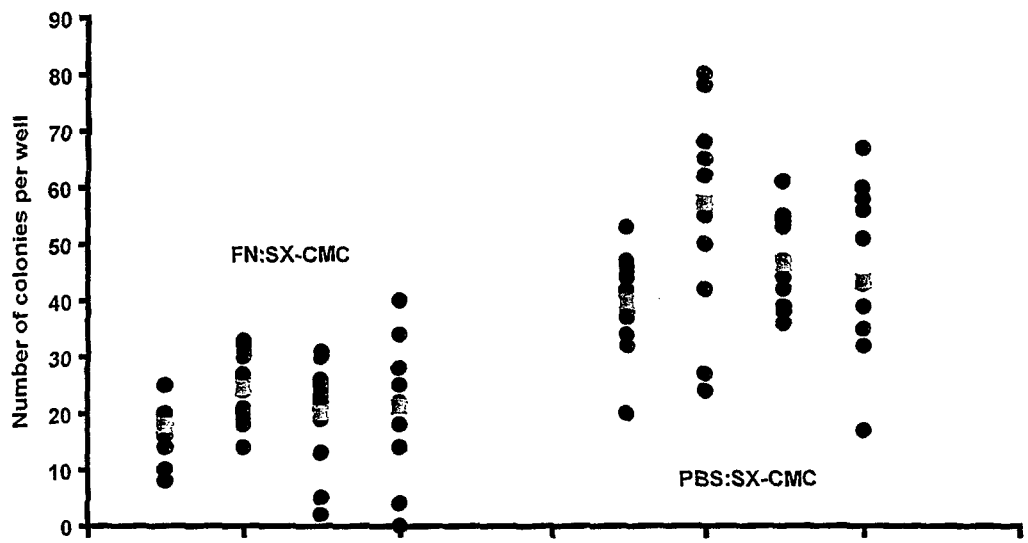
Fig. 3.7
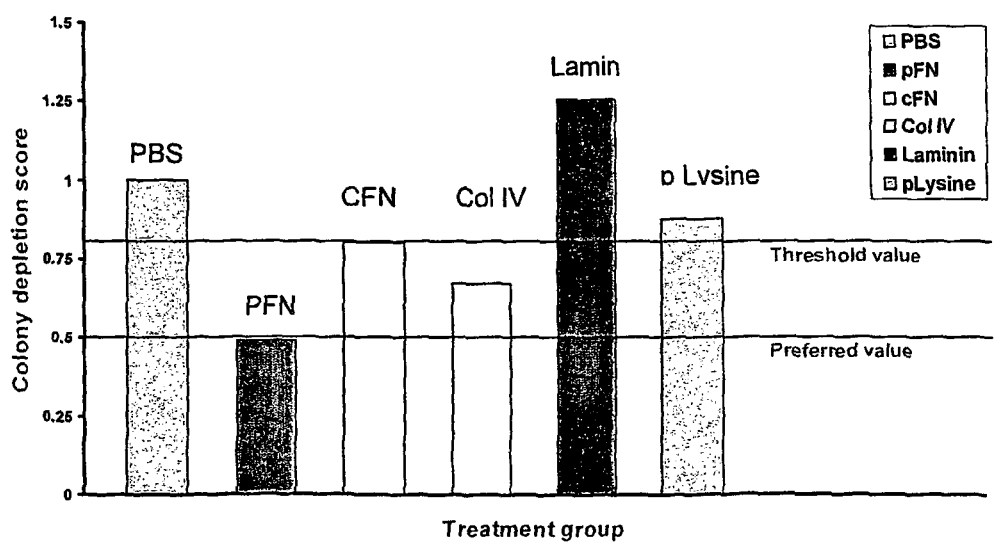
Fig. 3.8

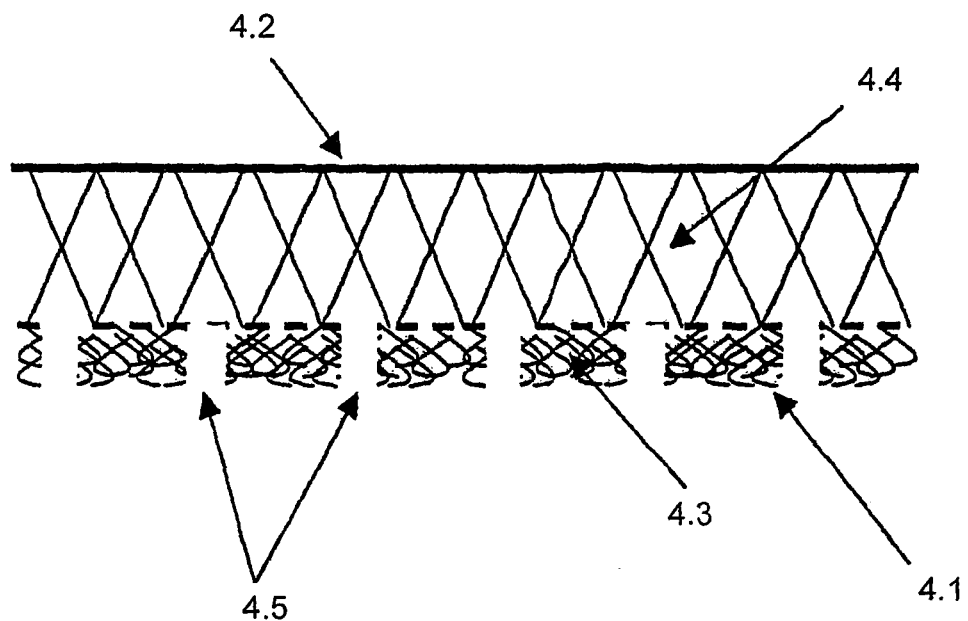
Fig. 4.1
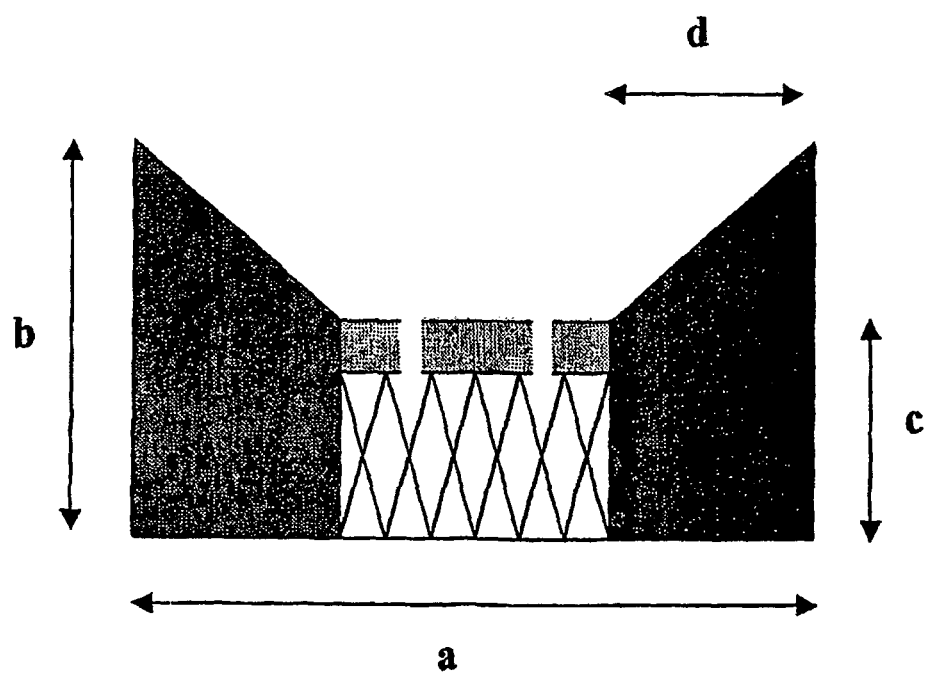
Fig. 4.2

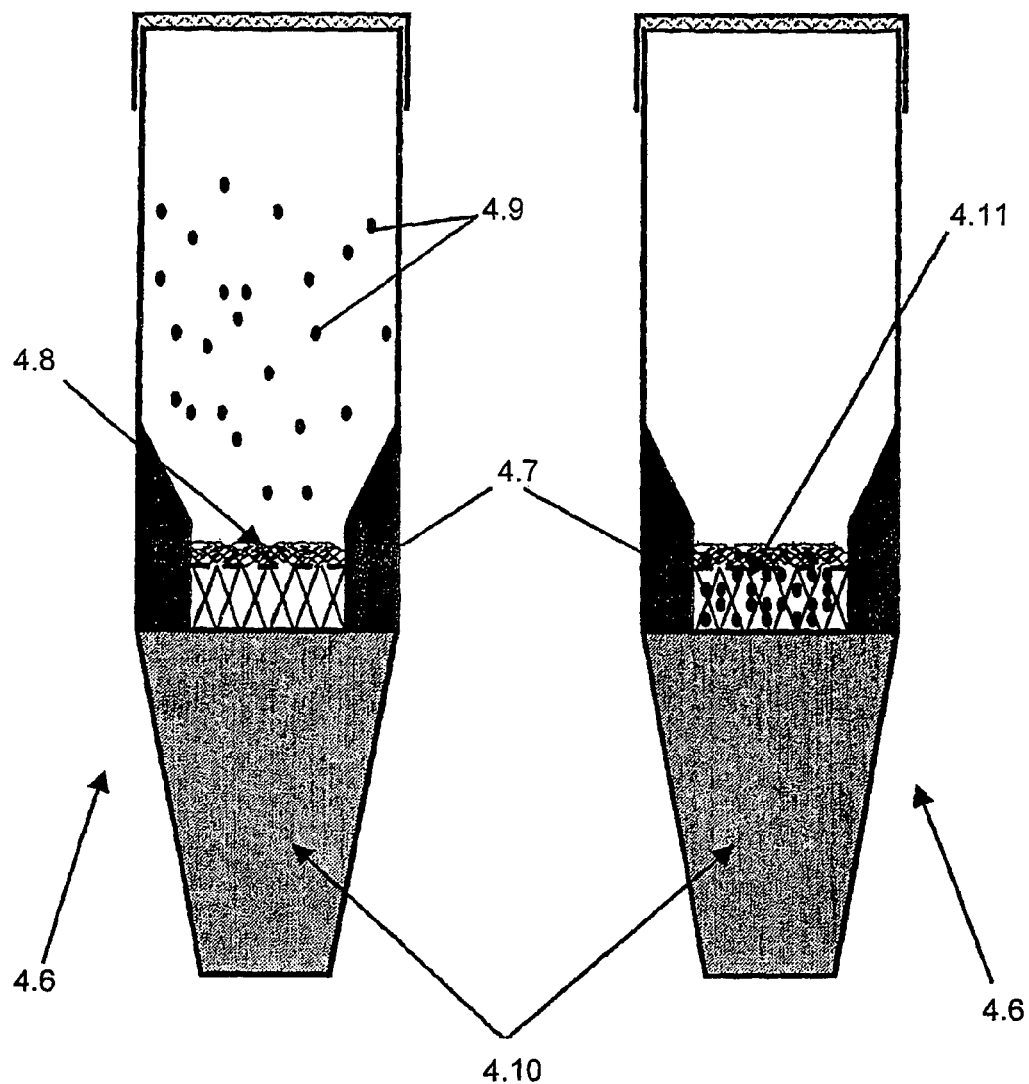
Fig 4.3　　　　　　　　　　Fig. 4.4

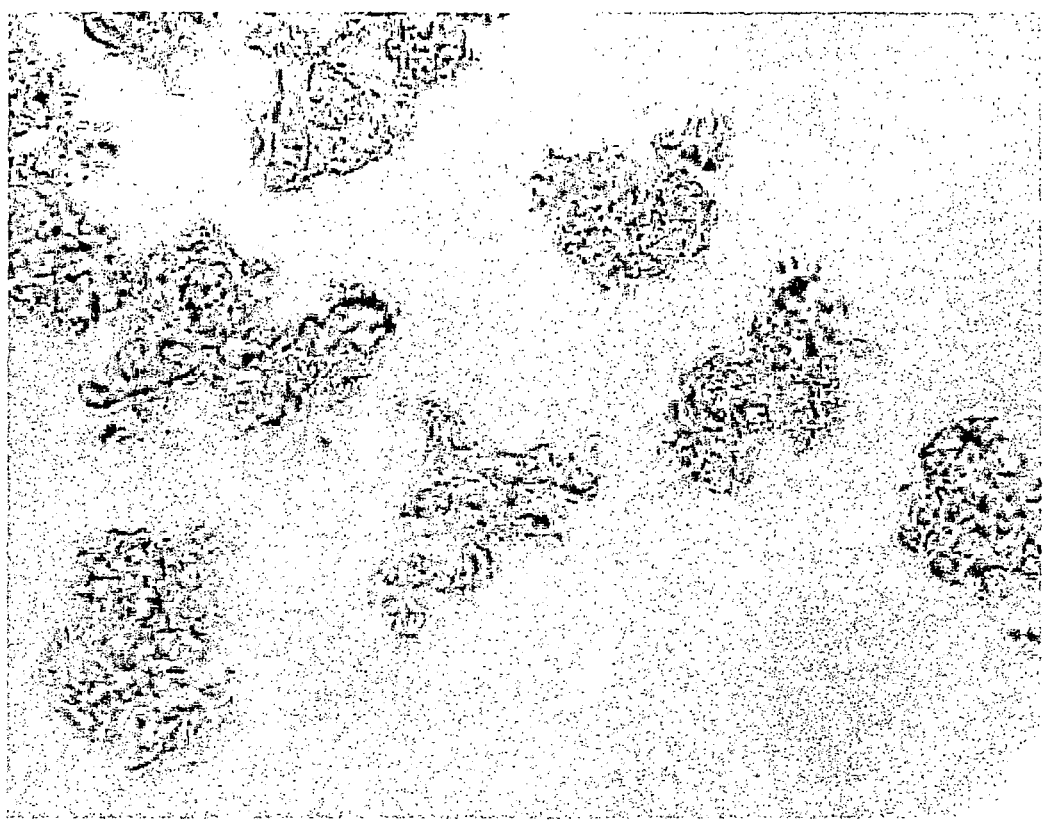
Fig. 4.5
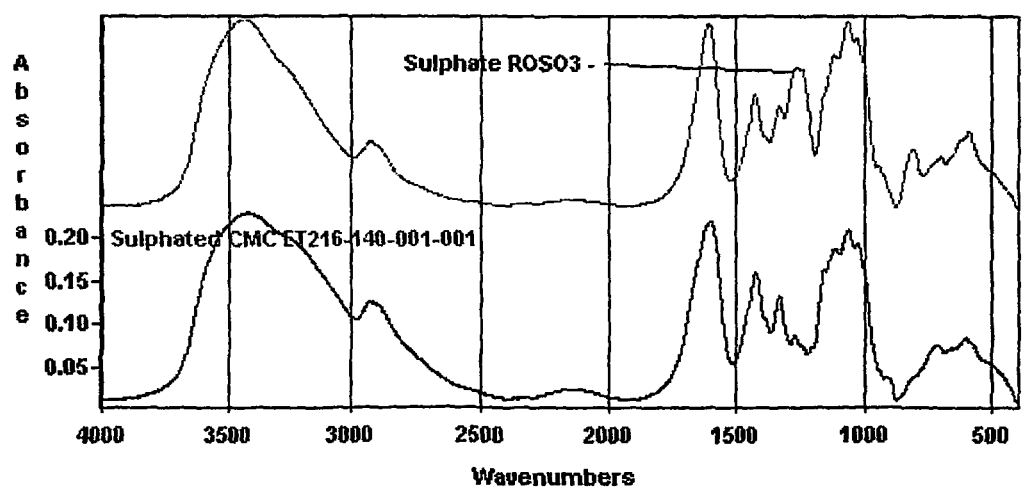
Fig. 4.6

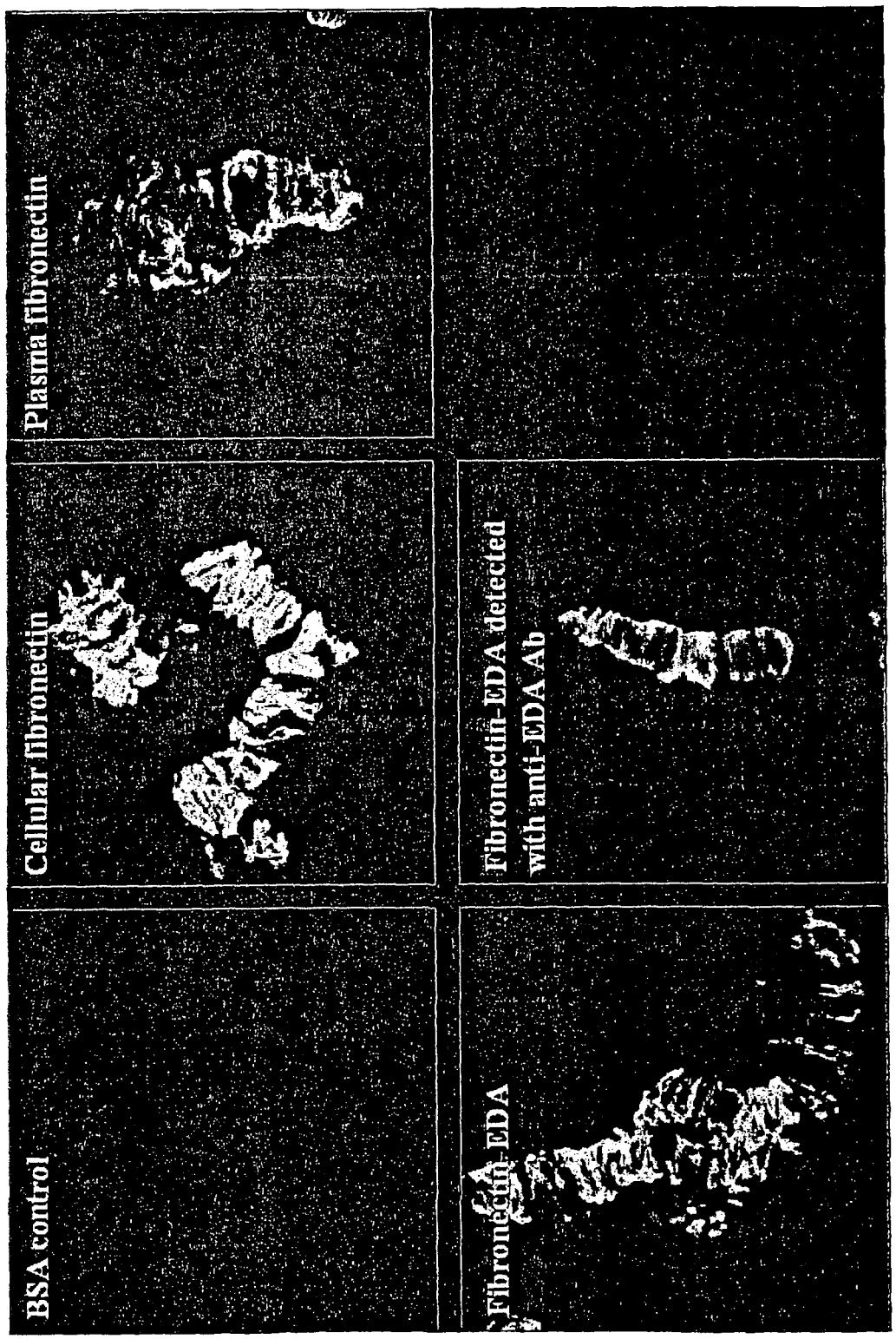
Fig. 4.7

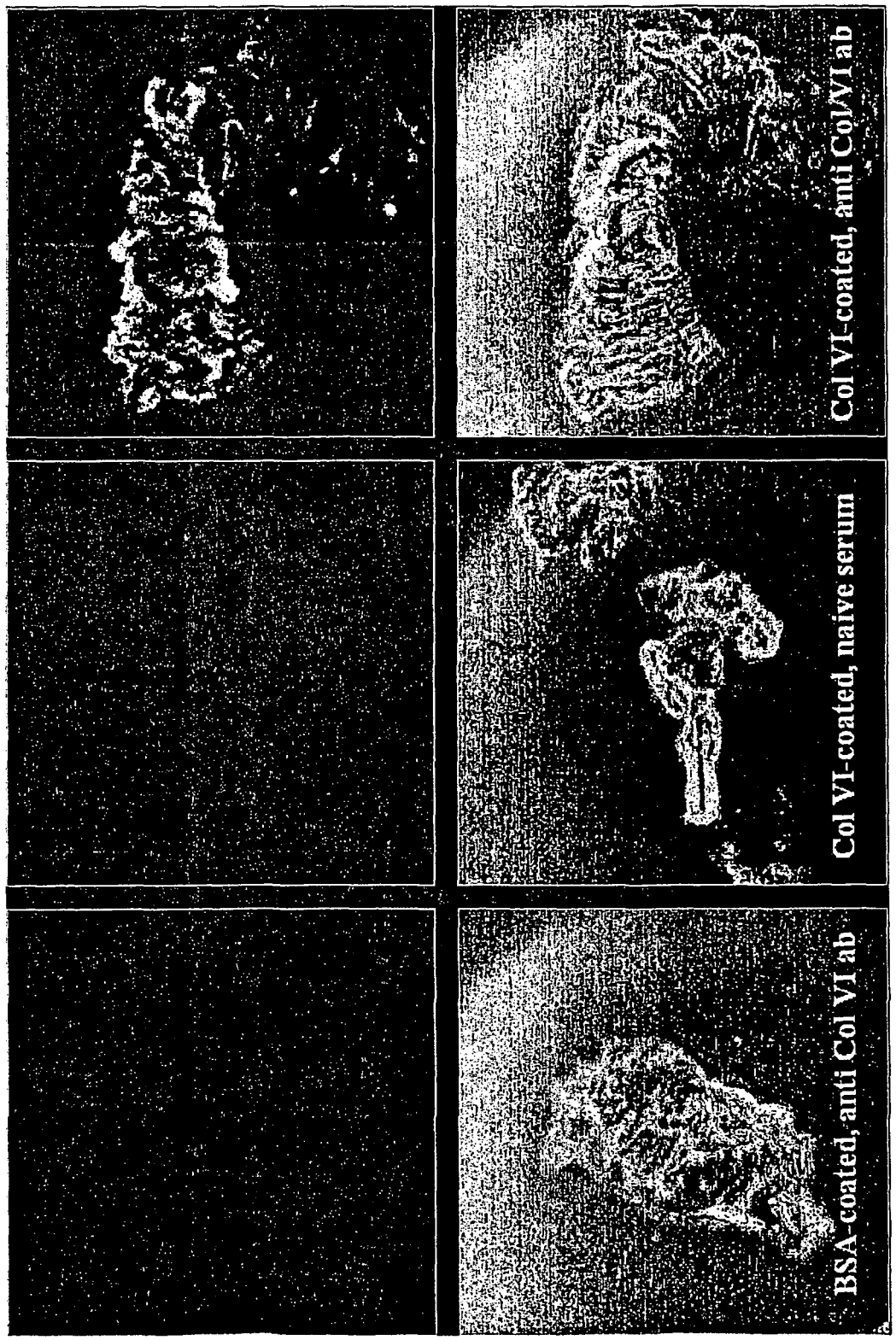
Fig. 4.8

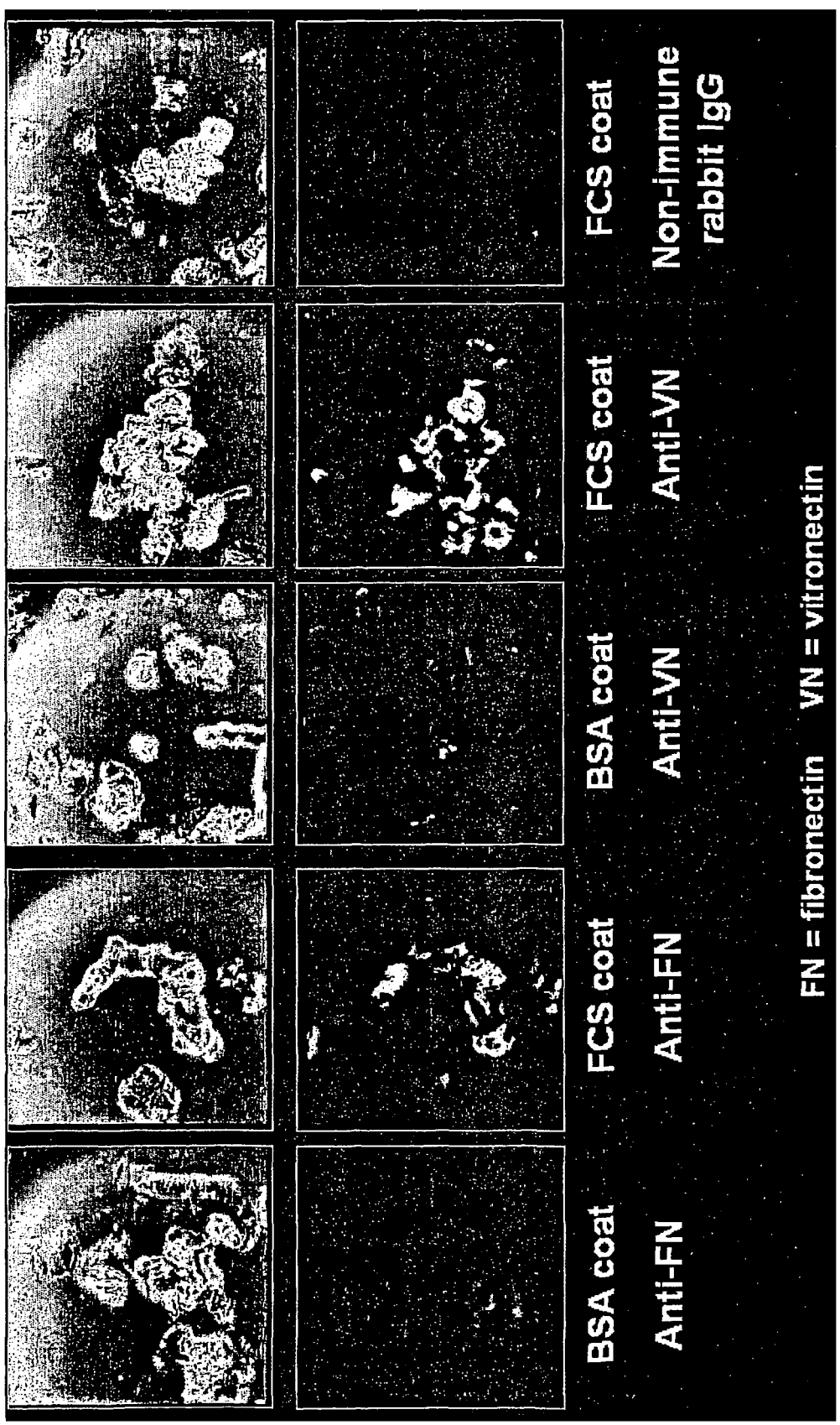
Fig. 4.9

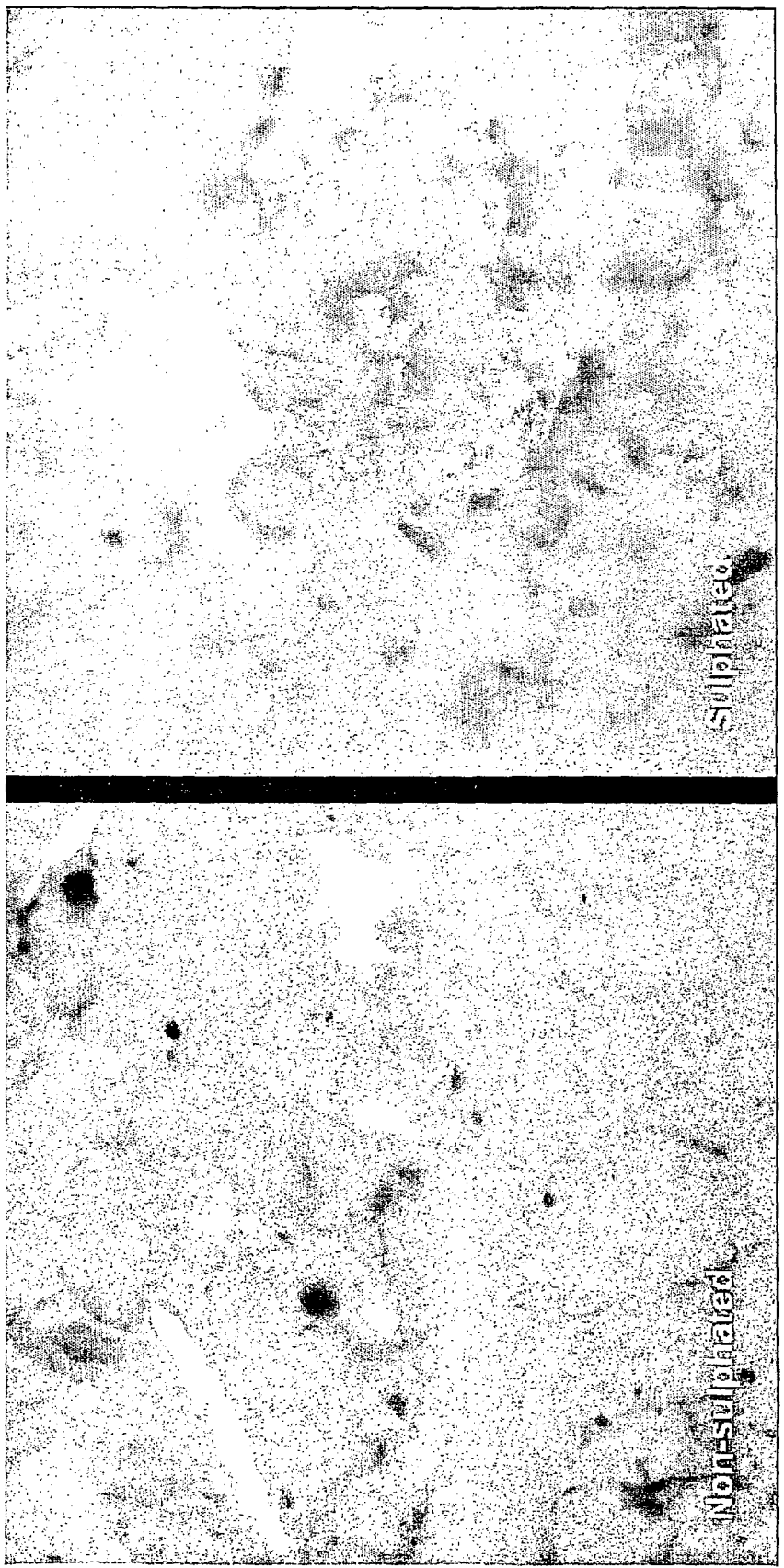
Fig. 4.10

TISSUE IMPLANT

The invention relates to an implant for the replacement of damaged cartilage and more particularly for the replacement of load-bearing cartilaginous tissue, such as the meniscus and articular cartilage. It also relates to a method of treatment comprising the step of surgically implanting an implant according to the invention and to a method of selectively concentrating chondroprogenitor cells present as a small proportion of a mixture of cells in a selected zone of the scaffold.

Popular current procedures for the treatment of articular cartilage defects include high tibial osteotomy (primarily performed in Europe) and muscle release to alter joint biomechanics and loading; lavage and debridement to remove osteophytes and fibrillated areas of cartilage and perforation and penetration of the subchondral bone to induce bleeding and clot formation. It has been established, however, that none of these techniques leads to successful regeneration of the tissue that duplicate the structure, composition, mechanical properties or durability of articular cartilage.

The most common technique is that of subchondral drilling which results in the creation of a fibrin clot and a fibrous tissue. In about 75% of patients there is a satisfactory result, but two years after the operation, only 12% of patients remain free of symptoms. Limitations of this approach are the difficulty in predicting the quality and duration of the clinical outcome and, in the long term, this procedure often leaves the patient in a worse condition. On the other hand, subchondral drilling and debridement are generally successful in alleviating symptoms and in postponing the requirement for total knee replacement by between one and three years.

Alternative allogenic tissue-engineered solutions to this technique involve only a single surgical procedure, but necessitate the production of implantable tissue-engineered grafts via a long and complex manufacturing process which is fraught with practical and regulatory difficulties.

A cartilage repair product which could predictably alleviate pain, restore function, achieve good fixation and which has a durability enabling it to last at least ten to fifteen years or more is seen as an important objective by many surgeons.

One currently available product which attempts to meet the above objectives comprises carbon fibre rods: the cartilage lesions are cleaned and excised down to the subchondral bone and the carbon fibre rods are inserted into holes made therein. Repair begins with the deposition of collagen around the top of the rods. These islands of growth soon enlarge to completely fill the defect, the rods providing anchorage for the repair tissue in the defect. A significant problem associated with this product is the production of carbon fibre wear debris found in the synovial cavity, which may give rise to problems of abrasion.

Another approach which has been considered is to use an areal implant comprising a knitted fabric, which provides structural stability, and a swellable hydrogel for containing and supporting cells seeded within it. This implant is placed in a cartilage lesion and is, intended to promote cartilage growth by means of the increased pressure derived from the swelling hydrogel.

Despite the advancements described above, there are currently no satisfactory treatments for focal, full-thickness lesions of articular cartilage: available methods are generally regarded as being insufficiently effective, excessively expensive or have other problems associated with them.

The approach of the present inventors has also been to consider, in detail, the structure of cartilage, particularly of articular cartilage. Articular cartilage forms a layer at the surface of joints. Whilst this tissue may, at first, appear to be homogenous in structure and composition, it actually comprises a number of zones. Three zones have been identified, being the superficial, middle (or intermediate), and deep zones of the tissue. The superficial zone comprises flattened cells orientated parallel with the cartilage surface. By comparison, the cells in the intermediate and deep zones tend to be more spherical and arranged either at random or in columns oriented perpendicular to the articular surface. These characteristic zone-specific cellular and structural properties are absent from the repair tissues, tissue-engineered constructs and products produced using current techniques.

While not wishing to be bound by any theory, it is considered now, for the first time, that the superficial zone cells are enriched in cartilage-forming chondroprogenitor cells. This is because (i) the cells in this zone are more metabolically and synthetically active than the cells of the deeper zones; (ii) they form colonies in vitro, (a widely recognised feature of highly proliferative precursor cells); (iii) they possess signalling systems that are characteristic of precursor cells and (iv) the kinetics of the uptake of metabolic labels is consistent with the existence of a pool of early chondroprogenitor cells. The superficial zone also comprises a number of extracellular matrix (ECM) components which are absent from deeper regions of the tissue. Whilst some of these components may have a purely structural or mechanical role within the tissue, other superficial zone ECM components may additionally serve to provide an appropriate biochemical environment for the chondroprogenitor cells, (a so-called 'stem cell niche'). In addition, it is considered that certain ECM components found in the intermediate and deep zones may contribute to the formation and maintenance of structure and composition of those zones. Whilst not wishing to be bound by any theory, it is believed for the first time, that the cells in the superficial zone play an important part in cartilage formation and repair.

An improved approach to cartilage repair would aim to restore at least some of the layered tissue structure and composition which has been identified. In particular, it has now been identified that an improved approach to cartilage repair should restore a layer of chondroprogenitor cells similar to that which is present in the superficial zone of healthy articular cartilage.

In addition, current tissue-engineered approaches to the repair of focal articular cartilage defects are unable to meet the conflicting requirements of mechanical resilience and lateral integration. If a cell-seeded implant has a sufficiently robust extracellular matrix that it can withstand mechanical loading, then its cells are trapped within the matrix, unable to migrate into the surrounding tissue and therefore unable to contribute to lateral integration. Conversely, if the extracellular matrix in a tissue engineered articular cartilage graft is sufficiently permeable to permit cell migration and lateral integration, it is too weak to withstand mechanical loading.

It is recognised in the literature that chondrocytes proliferate but de-differentiate if grown as a monolayer of flattened cells upon a rigid substrate whereas they retain their functional phenotype but do not divide if maintained in conditions that allow them to adopt a rounded morphology, (e.g. within alginate gels), especially in conditions of high cell density. Existing scaffolds do not provide the required combination of environmental stimuli to produce large numbers of functional chondrocytes from limited initial numbers of cells.

A first object of the present Invention is to provide a medicament for treating diseases or conditions characterised by cartilage defects.

A second object of the present invention to provide a tissue implant which can be flush-fitted into a cartilage defect, particularly a defect in articular cartilage, and which promotes rapid healing and tissue regeneration.

A further object of the present invention is to provide a tissue implant which can restore the cellular and structural properties of the superficial zone of cartilage, particularly articular cartilage.

A further object of the present invention is to provide a tissue implant which can restore the cellular and structural properties of cartilage, particularly articular cartilage, located below the superficial zone.

A further object of the present invention is to provide a tissue implant which can withstand mechanical loading, but is also sufficiently permeable to permit cell migration and lateral integration.

It is also an object of the present invention to provide chondroprogenic binding materials.

A further object still of the present invention is to provide an alternative scaffold suitable to carry cells e.g. chondroprogenic cells.

Cells

According to a first aspect of the invention there is provided an isolated population of superficial zone chondroprogenic cells.

By the term 'superficial zone chondroprogenic cells' we mean chondroprogenic cells found within the superficial zone of healthy articular cartilage. These chondroprogenic cells have a specific tissue location (i.e. within the superficial zone), different control systems to neighbouring chondrocytes, (e.g. the signalling receptor Notch is present) and a distinctive extracellular matrix that includes the fibronectin splice-variant Fibronectin-EDA.

Preferably the cells will be mammalian cells, suitably human.

The isolating of a population of superficial zone chondroprogenic cells may be by obtaining any enriched population of superficial zone chondroprogenic cells from superficial zone of cartilage of the joint of a mammalian e.g. a human.

These cells could then be grown in vitro before being administered to a patient. Administration of the live cells may be with, or without, a suitable carrier e.g. a scaffold on an implant.

Surprisingly the superficial zone chondroprogenic cells are able to correct cartilage defect in the body by simply being administered to the body.

It was previously the view in the technical field that these superficial zone chondroprogenic cells had no role to play in or cartilage repair.

It was previously believed that the superficial zone chondroprogenic cells being of a flat appearance had only mechanical function, involved in matrix function.

It is generally accepted that articular cartilage tissue does not contribute to the cellular source of healing of articular cartilage lesions (Mankin H J The reaction of articular cartilage to injury and osteoarthritis. Part I N Engl. J Med. 1974; 291: 1286, Mankin H J The reaction of articular cartilage to injury and osteoarthritis. Part II N Engl. J Med. 1974; 241: 1335, Operative Arthroscopy Editor-in-Chief John B McGinty).

It was commonly believed in the art that under normal circumstances, chondrocytes in mature articular cartilage rarely, if ever, divide, and the cell numerical density of cartilage, particularly in the superficial layer, declines with age. (Ref: Stockwell R A: The cell density of human articular and costal cartilage. J Anat 1967; 101: 753-763, Stockwell R A, Meachion G: The chondrocytes, in Freeman M A R (ed): Adult Articular Cartilage, ed 2, Tunbridge Wells, Pitman Medical, 1979, pp 69-144).

These age-related decreases in cell density and cell synthetic function may limit the ability of the cells to restore a damaged matrix. (American Academy of Orthopaedic Surgeons Symposium-Injury and Repair of the Musculoskeletal Soft Tissues; Chapter 9, Chondrocytes paragraph; pp 414 to 416).

In fact it was believed in the art that the procedure to repair cartilage was by the technique of making multiple small drill holes into subchondral bone. The repair tissue would grow from the drill holes and spread over the exposed bone. (Articular Cartilage and Knee Joint Function, Basic Science and Arthroscopy, Perforation or Abrasion of Subchondral Bone paragraph; pp 44, A symposium Organized by the arthroscopy Association of North America and sponsored by Bristol-Myers/Zimmer, edited by J Whit Ewing).

Surprisingly chondroprogenic cells e.g., superficial zone chondroprogenic cells, can promote differentiation of other chondroprogenic cells and can also promote chondrogenesis.

Surprisingly chondroprogenic cells, e.g. superficial zone chondroprogenic cells can promote cartilage repair and in particular can promote articular cartilage repair.

Live superficial zone chondroprogenic cells may therefore be used in a medicament or composition or implant to treat diseases or conditions characterised by cartilage defect.

According to one aspect of the invention there is provided a method for the treatment of diseases or clinical conditions characterised by cartilage deficiency, the method comprising administering live superficial zone chondroprogenic cells.

According to another aspect of the present invention there is provided an implant suitable for repair of a cartilage defect comprising a first surface suitable to be located at, or near, a bone-cartilage interface and a second surface suitable for locating contiguous with or near to an-exposed articular surface such that the implant further comprises superficial zone chondroprogenic cells.

Layered Structure

According to another aspect of the present invention there is provided an implant suitable for repair of a cartilage defect comprising a first surface suitable to be located at, or near, a bone-cartilage interface and a second surface suitable for locating contiguous with or near to an exposed articular surface such that the implant further comprises a higher concentration of immature chondroprogenic cells at or near to the articular surface than at the bone-cartilage interface.

The chondroprogenic cells near to, or at, the bone-cartilage interface tend to be more mature chondroprogenic cells than the cells near to, or at, the articular surface of the cartilage. The present invention in certain embodiments reflects this arrangement.

Suitably the immature cells are superficial zone chondroprogenic cells.

Having the immature chondroprogenic cells, e.g. the superficial zone chondroprogenic cells and the more mature chondroprogenic cells arranged in the same or similar structure as found in cartilage is beneficial to the cartilage growth and repair. The importance of having the immature chondroprogenic cells, e.g. the superficial zone chondroprogenic cells and the more mature chondroprogenic cells arranged in the same or similar structure as found in cartilage was not previously known.

As mentioned before, it was widely believed that these cells could not differentiate (or had limited capacity to differentiate) and had nothing to do with cartilage growth or repair. This was believed to be the case due to the cells flattened appearance and their distance from the cartilage-bone interface.

Suitably the implant of the present invention in which the distance between the first and second surfaces is $d_1$ comprises a greater concentration of immature chondroprogenic cells, e.g. superficial zone chondroprogenic cells, to a depth of $d_2$ from the second surface, than in the remaining depth of the implant, where $d_2/d_1<1$, but also in which $d_2/d_1<0.5$, <0.3 or <0.2.

A suitable biocompatible scaffold may be used within the implant to carry the chondroprogenic cells, e.g. superficial zone chondroprogenic cells. Any suitable material to act as a scaffold or carrier may be used e.g. sulphated Intrasite gel.

The implant may be in the form of a single layer, a multiple of layers, microbeads or any other suitable shape to enable the working of the invention.

The implant may also have a reinforcing component to aid strength of the implant. Preferably the implant will comprise bioresorbable material.

Also according to the present invention there is also provided a method of producing an implant comprising the steps: locating or positioning immature chondroprogenic cells, e.g. superficial zone chondroprogenic cells, in a higher concentration near to a second surface of the implant than to a first surface of an implant, in which the first surface of the implant is suitable to be located at, or near, a bone-cartilage interface and the second is suitable for locate contiguous with, or near, an exposed articular surface.

Also according to the present invention there is provided a method of promoting chondrogenesis, by positioning a cell near to, or in contact with or in communication with, an implant of the present invention. Suitably the cell for which chondrogenesis to be promoted, will be a chondroprogenic cell or a chondrocyte.

Similarly according to the present invention there is provided a method of promoting differentiation of chondroprogenic cells by positioning the chondroprogenic cell near to, or in contact with, or in communication with an implant of the present invention.

The communication means may be any means by which the superficial zone chondroprogenic cells can cause differentiation or chondrogenesis.

Binding Material

According to an alternative aspect of the invention, an implant for repair of a cartilage defect is presented, the implant having a first surface suitable to be located at or near a bone-cartilage interface and a second surface suitable for location contiguous with or near to an exposed articular surface, such that the distance between the first and second surfaces is $d_1$, wherein the implant comprises a biocompatible scaffold and a chondroprogenitor cell-binding material to a depth, $d_2$, from the second surface of the implant, where $d_2/d_1<1$.

According to a further aspect of the invention, an implant for repair of a cartilage defect is presented, the implant having a first surface suitable to be located at or near a bone-cartilage interface and a second surface suitable for location contiguous with or near to an exposed articular surface, such that the distance between the first and second surfaces is $d_1$, wherein the implant comprises a biocompatible scaffold and a substance capable of absorbing a chondroprogenitor-cell binding material to a depth, $d_2$, from the second surface of the implant, where $d_2/d_1<1$.

As stated in the introduction, an aim of the present invention in one embodiment is to restore at least some of the layered tissue structure and composition identified in natural cartilage, particularly articular cartilage. Importantly in some embodiments of the present invention it is desired to restore structure and composition of the superficial zone. By incorporating a chondroprogenitor cell-binding material or a substance capable of absorbing a chondroprogenitor-cell binding material into a region depending from the second surface (the surface suitable for location contiguous with or near to an exposed surface, i.e. the surface from which the superficial zone depends), chondroprogenitor cells may be attracted to and bound to this region of the implant, thereby helping to achieve the stated aim.

Reference herein to a material being 'biocompatible' means that there is essentially no clinically significant acute or chronic adverse response when the material is surgically introduced into a mammalian organism over and above that which would occur as a result of sham surgery alone.

Reference herein to a 'scaffold' is to a three dimensional, at least partially porous structure, the porosity being sufficient to allow cell infiltration, the exposed parts of the scaffold (both internal and external) allowing cell adhesion and growth such that cell proliferation and extracellular matrix (ECM) generation can occur and tissue can be laid down.

Reference herein to 'chondroprogenitor cells' means cells, such as mesenchymal stem cells, which are at or towards the start of the chondrocytic lineage and typically have a high capacity to proliferate.

Reference herein to the 'chondrocytic lineage' is to the pathway whereby mesenchymal stem cells mature ultimately to give rise to terminally differentiated post mitotic chondrocytes.

Reference herein to a 'chondroprogenitor cell-binding material' is to a material which preferentially binds cells at or towards the start of the chondrocytic lineage, such as mesenchymal stem cells, over cells towards the end of the lineage.

Reference herein to a 'substance capable of absorbing a chondroprogenitor-binding material' means a material which can physically adsorb (i.e. non-covalently bind), or chemically bind (i.e. via the action of a covalent cross-linker) a chondroprogenitor cell-binding material, as defined above, thereby forming a complex, itself having an enhanced affinity to bind chondroprogenitor cells.

The scaffold according to the present invention may comprise one layer or it may comprise a plurality of layers. The or each layer comprises a three dimensional, at least partially porous structure, as defined above. The or each layer may, for example, comprise a three dimensional woven or knitted fabric. (i.e. a spacer fabric), a fleece (i.e. non-woven) material, a sponge, a foam, microcarrier beads or a combination of these materials. If the scaffold comprises a plurality of layers, these layers may all comprise an identical material. Alternatively, each layer may comprise material which is different from some or all of the other layers.

In the event that the scaffold according to the invention comprises at least one layer of three-dimensional woven or knitted fabric, it is preferred to heat set the layer(s). This step causes the molecules in the fibres to re-align to the orientation imposed upon the fibres and causes the fabric to shrink somewhat. Both effects serve to render the fabric more stable. Heat setting is carried out a temperature and for a time known to the skilled man in this field and depends upon the material in question.

In a preferred form the scaffold according to the invention comprises two layers. Advantageously, one layer comprises a three-dimensional knitted structure and the other layer comprises a non-woven (felt) material affixed thereto. These two layers may be fixed to one another by a variety of methods, such as stitching, needling, heat bonding (by incorporating thermosetting fibres into one or both of the knitted and felt layers) or by means of an adhesive or polymer solution.

As used herein, the term 'microcarrier beads' means any particulate material capable of supporting cell adhesion or possessing a cell-binding surface layer. Such particulates may be in the size range 25-20001 µm and are preferably in the range 100-250 µm. Examples of materials from which such beads may be constructed are cross-linked proteins, polysaccharides, derivatised polysaccharides and synthetic biocompatible polymers, such as those listed below for manufacture of the scaffold. Commercially available microcarrier beads are supplied by Pharmacia and Sigma.

The scaffold layer or layers may comprise bioresorbable or non-bioresorbable materials.

Reference herein to a material being bioresorbable means that it breaks down over time due to chemical/biological action and the terms 'resorption' and 'resorb' are to be interpreted accordingly. Preferably, complete resorption occurs within about 5 years, more preferably within about 3 years. An advantage of using bioresorbable materials is that they break down allowing repair tissue completely to fill the defect site such that further surgery to remove them is not necessary.

If a single bioresorbable material is employed, then a preferred selection criterion for it is that it does not significantly resorb during the period of time that tissue is being laid down within it. Fulfilment of this condition ensures generation of an implant comprising living cells, which also essentially retains its shape and mechanical integrity. In numerical terms, it is preferred that there be less than a 5% loss of weight when the bioresorbable material is implanted in vivo for a 12 week period. More preferably, there is less than a 2% loss of weight during the same period. If, on the other hand, there are two or more bioresorbable materials, then it is preferred that at least one of the bioresorbable materials fulfils this criterion in order to provide structural integrity to the implant.

A wide range of bioresorbable materials is known, with differing in vivo resorption times. Not only does the resorption time vary according to the material, but the resorption time of a single material itself can also vary significantly with molecular weight and structural disposition. Finally, it can readily be appreciated that by blending and/or copolymerising different bioresorbable materials and/or by modifying the molecular weights or crystallinity of the components, it is possible precisely to tailor the resorption time of the bioresorbable material to the requirement at hand.

With the above in mind, the bioresorbable materials according to the invention may comprise bioresorbable polymers or copolymers comprising the following monomers or mixtures of polymers and/or copolymers formed thereby: hydroxy acids, particularly lactic acid, glycolic acid; caprolactone; hydroxybutyrate; dioxanone; orthoesters; orthocarbonates; aminocarbonates.

The bioresorbable materials according to the invention may also comprise natural materials such as collagen, cellulose, fibrin, hyaluronic acid, fibronectin, chitosan or mixtures of two or more of these materials. The bioresorbable materials may also comprise devitalised xenograft and/or devitalised allograft.

Bioresorbable ceramics may also be included within the scaffold. Bioresorbable ceramics which may be used according to the invention are mono-, di-, octa-, α-tri-, β-tri and tetra-calcium phosphate, hydroxyapatite, fluoroapatite, calcium sulphate, calcium fluoride, calcium oxide or mixtures of two or more of these materials.

Preferred bioresorbable materials according to the invention comprise poly(lactic acid), poly(glycolic acid), polydioxanone, polycaprolactone, polyhydroxybutyrate and poly (trimethylene carbonate) or mixtures thereof.

It is particularly preferred to use poly(lactic acid). This material has the advantage that it has good mechanical strength and does not resorb too quickly, thus allowing its mechanical properties to be retained for a sufficient time for tissue repair to occur at which point the repaired tissue can take over load-bearing functions: with reference to A. G. A. Coombes and M. C. Meikle, 'Resorbable Synthetic Polymers as Replacements for Bone Graft', Clinical Materials 17, (1994), pp 35-67 samples of poly(lactic acid) have been shown to lose only one or two percent of their weight over a 12 week trial.

Appropriate non-bioresorbable materials according to the invention include polyesters, particularly aromatic polyesters, such as polyalkylene terephthalates, like polyethylene terephthalate (PET) and polybutylene terephthalates; polyamides; polyalkenes such as polyethylene and polypropylene; poly(vinyl fluoride), polytetrafluoroethylene carbon fibres, silk (natural or synthetic), carbon fibre, glass and mixtures of these materials. In addition, non-resorbable ceramics may be employed. Examples of such materials are pure hydroxyapatite, zirconia and alumina. An advantage of non-bioresorbable materials is that they essentially retain their initial mechanical properties—i.e. properties such as strength do not reduce over time. They may therefore provide long-term mechanical support to the repair tissue.

In the advantageous case in which the scaffold according to the invention comprises two layers—a knitted layer affixed to a felt layer, as defined above, then it is particularly advantageous to manufacture the knitted layer so that it comprises poly(lactic acid) or PET and the felt layer so that it comprises poly(glycolic acid).

According to a preferred form of the first aspect of the invention, the scaffold may be reinforced by inclusion of a reinforcing component within the structure to assist in withstanding mechanical loading. If the scaffold comprises a plurality of layers, then from one to all of the layers may be reinforced. The reinforcing component may comprise a bioresorbable or non-bioresorbable polymer of the types listed above for manufacture of the scaffold. Preferably, the reinforcing component comprises a molten thermosetting polymer or a solution of a thermosetting polymer which is added to the scaffold in a fashion such that it connects adjacent strands within the scaffold, thereby improving its compressive modulus. More preferably, the reinforcing component comprises polycaprolactone.

One method of providing the above-mentioned reinforcement is to compress the fabric between two 'nip' rollers over which is supplied a pool of molten or dissolved reinforcing polymer. As the fabric is compressed and forced between the rollers a small quantity of reinforcing polymer is carried with it and this is drawn into the fabric when it re-expands on the other side of the rollers, thereby coating the fibres.

The implant according to the invention advantageously comprises at least one layer which has a compressive modulus of greater than or equal to 1 MPa. Preferably, the compressive modulus of the layer or layers is in the range 1-3 MPa and more preferably still, it is in the range 1-2 MPa. The compressive modulus of the layer or layers may be an inherent property or may result from a reinforcement step, such as described above.

Chondroprogenitor cell-binding materials which may be used according to the invention include fibronectin, type IV collagen, anti-notch antibody, anti-integrin $\beta_1$ antibody and combinations of these materials.

Fibronectin is an extracellular-matrix glycoprotein encoded by a single gene, but with significant protein heterogeneity introduced through alternative RNA splicing and post-translational modifications. Reference herein to 'fibronectin' includes fibronectin; binding splice-variants of fibronectin, such as FIBRONECTIN-EDA, or fibronectin extra-domain A (also called EIIIA or EDI), FIBRONECTIN-EDB (also called EDIIIB or EDII) and FIBRONECTIN-IIICS (also called V, or variable); the domains themselves, such as EDA, EDB; homologues of fibronectin or its component domains (greater than 75% of sequence equivalence), or modified variants of fibronectin or its domains, such as an EDA sequence coupled to a linker sequence and/or a biomaterial binding sequence, such as polyHIS.

In a preferred form of the first aspect of the invention, the chondroprogenitor-binding material comprises FIBRONECTIN-EDA, the EDA domain on its own and/or the EDA domain coupled to a linker that allows it to be attached to the surface of a biomaterial. Splice variants of fibronectin, such as FIBRONECTIN-EDA, are known to be concentrated in the superficial zone of natural articular cartilage. Binding the materials listed to the superficial region of the implant may increase the selectivity of chondroprogenitor cell attachment to the surface of the device.

Substances capable of absorbing a chondroprogenitor-cell binding material according to the invention are polyanions including heparin, sulphated Intrasite™ and tetrahydrofurfuryl. If these materials are comprised within the implant according to the invention, they may absorb naturally occurring chondroprogenitor cell-binding materials, such as those listed above, from the surrounding tissue, following implantation. Alternatively, chondroprogenitor cell-binding materials may be added to the implant before or after implantation.

As stated above, the implant according to the invention comprises a chondroprogenitor-cell binding material or a substance capable of absorbing a chondroprogenitor-cell binding material. This material or substance may be comprised within a layer coated on the second surface of the scaffold, or it may be comprised within the scaffold itself, or both.

As also stated, if the distance between the first and second surfaces of the implant is $d_1$, the implant comprises the chondroprogenitor-cell binding material or the substance capable of absorbing a chondroprogenitor-cell binding material to a depth, $d_2$, from second surface of the implant such that $d_2/d_1<1$. Preferably, $d_2/d_1<0.5$, more preferably, $d_2/d_1<0.3$ and most preferably, $d_2/d_1<0.2$.

The chondroprogenitor-cell binding material or the substance capable of absorbing a chondroprogenitor-cell binding material disposed within the implant may be present in a constant concentration, as a continuous concentration gradient, or as a concentration gradient comprising a series of discrete steps. If present as a either type of concentration gradient, the concentration may increase in the direction moving from the first surface to the second surface or moving from the second surface to the first surface, but it is preferred that the concentration increase in the direction moving from the first to the second surface, since the highest concentration and thus the greatest degree of binding advantageously occurs towards the second surface of the scaffold.

Typically, the thickness of the region comprising chondroprogenitor-cell binding material or the substance capable of absorbing a chondroprogenitor-cell binding material, i.e. the depth $d_2$ from the second surface, is in the range 0.05 mm-8 mm, or more preferably 0.2 mm-8 mm.

As stated in the introduction, it is considered that certain ECM components found in zones other than the superficial zone may contribute to the formation and maintenance of structure and composition of those zones. In a preferred form of the first aspect of the invention, the implant additionally comprises a further cell-binding material capable of binding cells found in zones other than the superficial zone of cartilage, particularly articular cartilage, such as type I collagen, type II collagen, type VI collagen or vitronectin. These materials are comprised within the implant to a depth, $d_3$, from the first surface of the implant, such that $d_3/d_1<0.8$. Preferably, $d_3/d_1<0.7$ and more preferably, $d_3/d_1<0.5$.

As will be evident from the preceding discussion, it is the intention that the implant according to the invention become populated with cells. This may be achieved by allowing a sterile implant to become populated with cells migrating from the surrounding host tissue into the implant. Such a migration-process may be assisted, for example by incorporating matrix degrading enzymes or chemotactic factors in and around the implant.

Alternatively, autologous or allogenic chondroprogenitor cells may be added to the implant. Suitable sources of chondroprogenitor cells include any source of undifferentiated mesenchymal cells, (e.g. bone marrow, purified or enriched populations of bone marrow stromal cells, pericytes, periosteum, perichondrium, adipose or cells derived from the cambrial layer of periosteum or perichodrium). These cells may be added either before or after implantation.

According to another aspect of the invention a method of treatment of a cartilage defect in a mammalian organism is presented, the method of treatment comprising the step of surgically implanting an implant as above defined.

According to another aspect of the invention, a method is presented of selectively concentrating chondroprogenitor cells present as a small proportion of a mixture of cells, comprising the step of attaching a chondroprogenitor cell-binding material to a support matrix and passing the mixture of cells therethrough or thereover or allowing it to rest thereupon, thus allowing the chondroprogenitor cells to adhere to said chondroprogenitor cell-binding material, followed by the step of washing to remove contaminant cells.

In the method according to a particular aspect of the invention, the mixture of cells comprising the chondroprogenitor cells may, for example, be derived from cartilagenous and non-cartilagenous sources of early mesenchymal precursor cells, such as Whartons jelly, bone marrow, the superficial zone of articular cartilage, periosteum or perichondrium.

The support matrix according to one embodiment of the invention may be a Petri dish or an affinity column and attachment may be physical or chemical. The last step may, for example, comprise a gentle washing with culture medium.

Reference is made to the figures of the application:

FIG. 1.1 shows immunolocalisation of N1 (Notch-1). N1 expression (green, 1.11) shown to be almost entirely confined to the upper 2-3 cell layers of the superficial zone of neonatal bovine articular cartilage cells that do not express N1 are counterstained (red, 1.10) by propidium iodide. Arrows 1.13 indicate the articular surface.

FIG. 1.3 shows immunolocalisation of Fibronectin-EDA. Fibronectin-EDA expression is cell associated and almost entirely confined to the superficial zone of articular cartilage (green, 1.31). Cells that do not express Fibronectin-EDA are counterstained (red, 1.32) by propidium iodide. Arrows (1.33) indicate the articular surface.

FIG. 1.4 shows minimal immunolocalisation of Fibronectin-EDA in the mid zone.

FIG. 1.5 shows the control of FIG. 1.4; Control section, note absence of green stain.

FIG. 1.6 shows N1 immunolocalisation.

FIG. 1.7 is a picture of Fibronectin-EDA immunolocalisation.

FIG. 1.8 shows co-localisation of N1 and Fibronectin-EDA in immature bovine cartilage. Overlay of N1 immunolocalisation (green, 1.81), fibronectin-EDA immunolocalisation (red, 1.82). Arrows illustrate the articular surface. This illustrates that the cells expressing N1 also express fibronectin-EDA.

FIG. 1.9 shows the graph that the colony forming efficiency of the 'fast-fibronectin binding' superficial zone was significantly higher than that observed amongst the other groups of chondrocytes, ($p<0.01$).

FIG. 1.10 is a photomicrograph of colonies formed by the 'fast-fibronectin binding' superficial zone cells.

FIG. 1.11 represents Notch labelling immediately after chondrocyte isolation. Analysis of differential N1 expression by chondrocytes using FACS analysis. Approximately 75% of surface zone, 10% of middle and 25% of deep zone cells were positive for N1 immediately after isolation from the tissue.

FIG. 1.12 shows the effect of N1 positive selection on colony forming efficiency at 6 days using magnetic bead separation of Notch positive cells. There were significantly ($p<0.001$) more colonies from N1 positive surface zone cells than from N1 positive middle and deep zone cells.

FIG. 1.13 is an analysis of differential integrin expression by superficial zone chondrocytes using FACS.

FIG. 1.14 is a graph of average cell diameter of superficial, mid and deep zone chondrocytes (means±SEM). Measurement of average cell size of superficial, mid and deep zone chondrocytes. There are a significant difference in diameters between both SZC (superficial zone chondrocytes) and MZC (middle zone chondrocytes) ($p<0.05$) and SZC and DZC (deep zone chondrocytes) ($p<0.005$).

FIGS. 1.15a, b, c are representative photographs of a SZC, MZC and DZC respectively viewed using phase contrast optics (magnification ×200).

FIG. 1.16 shows the histological investigation of pellet cultures. H+E staining of 'fast-binding' superficial zone chondrocyte pellets showed the presence of morphologically normal and viable cells throughout the specimens FIG. 1.16a (7 day; SZC; H+E; ×5obj) and FIG. 1.16b (7 day; SZC edge; H+E; ×20obj).

FIG. 1.17 shows histological investigation of pellet cultures. Picrosirius red showed collagen deposition especially in the territorial matrix surrounding the cells (21 day; ×20obj).

FIG. 1.18 shows histological investigation of pellet cultures. Safranin O staining for glycosaminoglycans showed intense dark orange staining of the extracellular matrix produced by the cells, indicating that the cells had secreted a proteoglycans-rich matrix (21 day; SZC; ×5obj).

FIG. 1.19 shows immunocytochemical investigation of pellet cultures. Immunochemistry showed that the cells were synthesising cartilage specific matrix components in pellet culture. The extracellular matrix in the pellet contained collagen type II (14 day; SZC; ×20obj).

FIG. 1.20 shows immunocytochemical investigation of pellet cultures. Absence of collagen type I, indicates that the cells had differentiated to form chondrocytes and that de-differentiation had not occurred (14 day; SZC; ×20obj).

FIG. 1.21 shows the presence of chondroitin 4 sulphate in the matrix of the pellet cultures.

FIG. 1.22 shows the presence of chondroitin 6 sulphate in the matrix of the pellet cultures.

FIG. 1.23 is a fluorescence image showing distribution of link binding protein in pellets cultures (10 day; ×126obj).

FIG. 1.24 shows pellet cultures of superficial, mid and deep zone chondrocytes transplanted onto partial thickness cartilage defects.

FIG. 1.25 shows in ovo chondroprogenitor cell tracings using CFDA SE labelled cells areas of the embryo containing developing cartilage, e.g. the otic cup.

FIG. 1.26 shows bovine MHC1 possitive cells localised with Cy3-conjugated secondary antibody in soft connective tissue of chick embryos at H&H stage 30-32 (magnification ×126).

FIG. 1.27 Toluidine blue stained chick embryos at H&H stage 30-32. Bovine ectopic cartilage in chick wing formed from injected surface zone chondrocytes.
  A. Metachromatic staining of disorganised ectopic cartilage.
  B. Surrounding fibrous tissue.

FIGS. 2.1 and 2.2 show possible forms and profiles of 'zoned' areas of the culture.

FIG. 2.3 represents bone marrow stromal cells adhered to cell-adhesion factor coated sulphated. Intrasite within 16 hours, and proliferated.

FIG. 2.4 shows calcein AM staining revealed a population of adherent cells upon the surface of the material after 4 days.

FIG. 2.5 represents the deposition of a collagenous matrix after 7 days in culture shown by picrosirius red.

FIG. 2.6 depicts immunochemistry showed type I collagen production in specimens of bone marrow stromal cells cultured on fibronectin coated sulphated Intrasite after 10 days.

FIG. 2.7 show no evidence of collagen II production was observed.

FIG. 2.8 depicts MTT staining showed viable cells throughout the aggregates, both upon the surface of the material particles and in the spaces between them.

FIGS. 2.9a-2.9b show that the cells have deposited a collagenous matrix within the aggregates as stained by picrosirius red and also shows immunocytochemically that the chondrocytes expressed the cartilage specific form of collagen, collagen type II.

FIG. 2.10 shows by immunocytochemistry that the chondrocytes secrete collagen VI into their pericellular matrix.

FIG. 2.11 by immunocytochemistry this shows that the chondrocytes were not producing collagen I, even after 27 days in culture.

FIG. 2.12 is a graph showing that the ovine chondrocytes had increased in number 14.4 fold over the incubation period with the most rapid occurring during the first 10 days.

FIG. 2.13 show an outline of the equipment used and method used to form a bilayered construct by sequentially centrifuging (I) bone marrow stromal cell-seeded, fibronectin coated sulphated Intrasite and (II) chondrocyte-seeded coated sulphated Intrasite into a scaffold to form a two layered, fibre re-enforced cell/biomaterial construct.

FIG. 2.14 shows a preferred orientation of the 'asymmetric collar 'relative to the direction of rotation of the centrifuge rotor and the radical axis of the roto.

FIG. 2.15 shows the deposition of a bilayer of dyed sulphated Intrasite.

FIG. 2.16 shows a bilayered construct consisting of (I) a layer of pico green stained bone marrow stromal cell-seeded, fibronectin coated sulphated Intrasite and (II) a layer of EtBrHD stained chondrocyte-seeded coated sulphated Intrasite.

FIG. 2.17 shows the quantification of green fluorescence in the two felts compared to the control. Immediately apparent is the greater amount of N1+ fluorescence in the upper felt that was coated with fibronectin and seeded with the mixed population of chondrocytes for 30 minutes prior to the seeding of the lower felt with the same cell population.

FIG. 2.18 shows the quantification of green fluorescence in the various zones. Immediately apparent is the greater amount of Notch 1+ fluorescence in the upper surface of the felts which had had the upper surface coated with fibronectin.

FIGS. 3.1a-3.1d illustrate implants according to the invention.

FIGS. 3.2a-3.2c illustrate the use of coated microbeads with different cell-binding properties and buoyant densities/sedimentation velocities to produce a multi-layered implant. Two types of microbeads (particulate materials) with differing sedimentation velocities are mixed with a suspension of chondrocytes (FIG. 3.2a), and allowed to aggregate (FIG. 3.2b). One of the microbead-types is coated with a material which preferentially binds chondroprogenitor cells, while the other microbead type preferentially binds another cell-type (such as more mature chondrocytes found lower down the chondrocytic lineage). After cell attachment, the cell-covered microbeads are allowed to sediment to form a multi-layered deposit (FIG. 3.2c). The deposit can then be bound together to form an implant using a binding agent which sets in situ (e.g. alginate gel).

FIGS. 3.3a-3.3c illustrate production of a multilayered implant using a scaffold material, which may be a 3D-knit, in combination with two or more types of microbeads with differing sedimentation velocities. As in FIG. 3.2, one of the types of microbeads is coated with a chondroprogenitor cell binding-material; the other type is coated with a material which preferentially binds another cell-type (such as more mature chondrocytes found lower down the chondrocytic lineage). As in FIG. 3.2, the microbeads are mixed with a suspension of chondrocytes, (FIG. 3.3a), allowed to interact with the cells in suspension, (FIG. 3.3b) and sedimented into the void spaces of a biomaterial scaffold to form a multi-layered implant (FIG. 3.3c).

FIGS. 3.4a-3.4c illustrate production of a multilayered implant using a combination with two or more types of microbeads with differing sizes and cell binding affinities and a biomaterial scaffold-material, which may be a 3D-knit, designed to serve as a graded filter. As in the previous figures, one of the microbead-types is coated with a chondroprogenitor-cell binding material; the other is coated with a material which preferentially bind another cell-type found lower down the chondrocytic lineage. The cell-binding particles and chondrocytes, (not shown), are mixed, (FIG. 3.4a) and the cells allowed to bind preferentially to one or other class of bead, (FIG. 3.4b). The cell-covered microbeads are then drawn into a graded-filter. Smaller microbeads, (coated with one type of cell) are generally drawn further into the filter than the other type of microbead, (carrying a different cell type), thereby producing a layered device.

FIG. 3.5 is a schematic illustration of an implant according to the invention.

FIG. 3.6 shows colony forming efficiency of superficial and DZC 4 days after initial adhesion to various ligands. (FN, fibronectin; C1, collagen I; CII, Collagen II; BSA, bovine serum albumin; CIV, collagen IV; LM, laminin; TN, tensacin). Combined means (±sem) of 3 experiments, n=4 dishes per ligand per experiment.

FIG. 3.7 shows the use of colony depletion assay to show enhanced colony forming superficial zone cell attachment to fibronectin coated sulphated Intrasite compared to PBS coated sulphated Intrasite. Results are the number of colonies formed in each of the 12 wells in 4 replicate multiwell plates.

FIG. 3.8 shows the use of colony depletion assay to compare colony forming, bone marrow stromal cell adhesion to sulphated Intrasite coated with either PBS, plasma fibronectin, cellular fibronectin, collagen IV, laminin or polylysine. Plasma fibronectin-coated sulphated Intrasite has the highest affinity for the colony forming cells but collagen IV coated Intrasite also shows a high level of colony forming cell binding.

Preferred embodiments of the invention will now be described in ore detail with reference to these figures:

FIG. 3.1 shows four possible embodiments of this type of device:

FIG. 3.1a shows an implant comprising a single layer scaffold, itself comprising a non-woven polymeric felt. A portion of the scaffold extending down from its upper (articular) surface (3.2) comprises a chondroprogenitor cell-binding material (e.g. fibronectin). The lower (bone-contacting) surface (3.1) does not comprise chondroprogenitor cell-binding material.

FIG. 3.1b shows an implant comprising a single layer scaffold, itself comprising a three-dimensional knitted fabric, the implant having an upper (articulating) surface (3.2) covered with a coating comprising chondroprogenitor cell-binding material (e.g. fibronectin). Again, the lower (bone-contacting) surface (3.1) does not comprise chondroprogenitor cell-binding material.

FIG. 3.1c shows an implant comprising a single layer scaffold, the scaffold itself comprising a three-dimensional knitted fabric with a chondroprogenitor cell-binding material (e.g. fibronectin) being located therein. There is a concentration gradient of chondroprogenitor cell-binding material with the concentration decreasing with distance from the upper (articular) surface (3.4), such that this surface has a greater affinity for chondroprogenitor cells than the deeper regions of the implant, particularly the lower surface (3.3).

FIG. 3.1d shows an implant comprising a two-layer scaffold, incorporating an upper (articular) layer of three-dimensional knitted fabric and a lower (bone-contacting) layer of highly conformable, non-woven material. A chondroprogenitor cell-binding material (e.g. fibronectin) is comprised within the device such that the upper (articular) surface (3.6) of the device has a higher affinity for chondroprogenitor cells than the deeper bone interface layer (3.5). Chondroprogenitor cell-binding material may extend down into the lower layer or may be confined to the upper layer, depending on the layer thicknesses.

FIG. 4.1 illustrates a synthetic implant according to an embodiment of the invention.

FIG. 4.2 illustrates insert means for insertion into bioreactors according to the invention.

FIG. 4.3 illustrates a bioreactor according to an embodiment of the invention during the phase of sell seeding and incubation of the particulates.

FIG. 4.4 illustrates a hybrid implant located within a bioreactor according to an embodiment of the invention immediately after centrifugation of cell-seeded particulates into the synthetic implant of FIG. 3.

FIG. 4.5 shows the microscopic appearance of the sulphated material.

FIG. 4.6 shows representative spectra for the modified and unmodified materials.

FIG. 4.7 illustrates plasma fibronectin, cellular fibronectin and fibronectin-EDA binding to sulphated Intrasite™.

FIG. 4.8 illustrate collagen VI binding to sulphated Intrasite™.

FIG. 4.9 illustrate fibronectin and vitronectin binding to sulphated Intrasite™ following absorption from FCS.

FIG. 4.10 shows seeding of cells on sulphated and non sulphated Intrasite™.

IMPLANT COMPRISING A SCAFFOLD COMPRISING MICROBEADS COATED WITH CHONDRONROGENITOR CELL BINDING MATERIAL

An implant according to the invention may comprise microbeads coated with chondroprogenitor cell-binding material. In such a case, the scaffold may also comprise uncoated-beads and the beads are then arranged so that the coated ones are located down a depth, $d_2$, from the second surface of the scaffold. Such an arrangement may be achieved by a number of methods, such as by giving one type of bead a different size or density from the other type.

Taking this concept a step further, it is possible to coat some beads with chondroprogenitor cell-binding material and other beads with a material which binds other cells, such as more mature chondrocytes (those lower down the chondrocytic lineage) typically found in the intermediate and deep zones of cartilage, particularly articular cartilage. In FIGS. 3.2a-3.2c, 3.3a-3.3c and 3.4a-3.4c, the two different cell-types are represented by the following symbols:

An example of a chondroprogenitor cell-binding material is fibronectin-EDA in this case, and an example of the binding material for the deeper zones is collagen VI. The fibronectin-EDA and the collagen VI are coated onto two different types of particulate biomaterial, such as microcarrier beads, with differing sizes, densities and/or sedimentation velocities. In FIGS. 3.2a-3.2c, 3.3a-3.3c and 3.4a-3.4c, the two different bead-types are represented by the following symbols: ● ●

The microcarrier beads are sedimented to form a multi-layered deposit, which may be aggregated with a binding agent, such as alginate or pluronic gel to produce an implant in which each of the two binding agents is essentially confined to its appropriate zone (see FIGS. 3.2a-3.2c). Alternatively the coated beads may be allowed to sediment onto a scaffold material and then used with or without subsequent application of a binding agent (see FIGS. 3.3a-3.3c). Alternatively again, if the two types of beads differ in size, they can be separated by entrapping them in a scaffold that serves as a graded filter (see FIGS. 3.4a-3.4c—cells not shown), whereby the smaller particles are drawn further into the filter than the larger ones (carrying a different cell type) thus producing a layered device.

With reference to FIG. 3.5, a schematic illustration of an implant (3.7) according to the invention is shown. This implant has a first, lower surface (3.8), suitable to be located at or near a bone-cartilage interface and a second, upper surface (3.9), suitable to be placed contiguous with or near to an exposed, articular surface. The distance between the first and second surfaces is $d_1$. To a depth, $d_2$, from the second surface (3.9), the implant comprises chondroprogenitor cell-binding material. To a depth, $d_3$, from the first surface (3.8), the implant comprises a further cell-binding material, such as collagen VI, capable of binding cells found in zones other than the superficial zones of cartilage.

According to yet another aspect of the invention there is provided an implant for the repair of a cartilage defect which comprises a mature chondrocyte cell-binding material. Suitably the mature chondrocyte cell-binding material is type I collagen, type II collagen, type VI collagen or vitronectin.

Example 1

Characteristics of Superficial Zone Chondroprocienitor Cells

Summary

Our examples demonstrate that a layer of chondroprogenitor cells exist within the superficial zone of healthy articular cartilage:

1. Immunocytochemical analysis of intact cartilage shows that the chondroprogenitor cells have a specific tissue location, (i.e. within the superficial zone), different control systems to neighbouring chondrocytes, (e.g. the signalling receptor N), and a distinctive extracellular matrix, (including the fibronectin splice-variant Fibronectin-EDA).
2. In vitro analysis shows the cells rapidly bind fibronectin, have a high colony forming efficiency, (the 'gold standard' test for progenitor cells), a distinct pattern of integrin expression and a smaller than average cell size. In vitro analysis also shows that the cells may be enriched using anti-Notch antibody-coated magnetic beads and that the Notch positive cells have enhanced colony forming activity.
3. Pellet culture of the cells indicates that the superficial zone progenitor cells can form cartilage, confirming that they are part of the chondrogenic family of cells.
4. Incubation of the progenitor cells in contact with wounded cartilage reduces cell death and matrix breakdown in the injured cartilage, indicating that the progenitor cells maybe able to promote cartilage wound repair.
5. If injected intravasculary, in ovo, the cells localise to developing cartilaginous tissues, suggesting that they are chondroprogenitor cells rather than a more undifferentiated mesenchymal precursors.

Cells with the above combination of properties are not observed in mid or deep zone cartilage. Superficial zone chondroprogenitors cells also differ from early mesenchymal cells obtained from marrow stroma, because stromal cell colonies are fibroblastic and form within 4 days whereas the superficial zone chondrocytes form rounded cell colonies over a longer time period, (typically 6 days).

Taken together these results indicate that superficial zone cells constitute a distinct precursor cell stage within the chondrocytic branch of the mesenchymal family of cell lineages. Whilst the detailed pattern of marker expression may differ between species, with aging and disease or during wound repair, the existence of this progenitor cell layer is likely to be a recurring feature of articular cartilage development, maintenance and repair.

Example 1.1

Immunocytochemical Evidence of Chondroprogenitor Cells within the Superficial Zone of Neonatal Bovine Articular Cartilage Methods Preparation of Frozen Cartilage Sections.

Strips of full thickness articular cartilage, (approx 30 mm×3 mm), were removed from 2-3 week old bovine metatarsophalangeal joints, embedded in OCT (Gurr) and frozen using a liquid nitrogen cooled iso-pentane slush. Sections, (7 µm), were cut from the specimen using a Leica Jung CM3000 cryostat and placed on poly-lysine coated slides (Sigma). Sections were fixed by immersion in acetone for 10 minutes at room temperature and air dried. Slides were stored at −20° C. until used.

Immunolocalisation of N1.

Sections were washed in PBS, (2×10 minutes; Oxoid) and blocked with 2.5% normal rabbit serum (Dako) in PBS for 20 minutes at room temperature. The blocking solution was wicked-off using a paper tissue and the sections incubated with polyclonal goat anti-human N1 (C-terminal) antibody, (20 µg/ml in PBS; Santa Cruz), or an equivalent concentration of non-immune goat IgG (Dako) for 1 hour at room temperature. Sections were washed with PBS, (3×10 minutes) and incubated with a 1:100 dilution in PBS of rabbit anti-goat-FITC conjugate for 45 minutes at room temperature followed by washing in PBS for 3×10 minutes. Sections were mounted with Vectashield (Vector) containing propidium iodide, coverslipped and viewed using a Leica DM-RE confocal microscope using an ArKr laser exciting at 488 nm and 568 nm.

Immunotocalisation of Fibronectin-EDA.

Frozen sections of neonatal bovine articular cartilage were digested with hyaluronidase (5 µg/ml, 37° C., 1 hour; Sigma) to expose the pericellular matrix, washed in PBS, (2×10 minutes) and blocked with 2.5% normal rabbit serum (DAKO) in PBS for 20 minutes. The blocking solution was wicked-off using a paper tissue and the sections incubated with mouse monoclonal anti-fibronectin-EDA antibody (50 µg/ml in PBS; Oxford Biotechnologies) or an equivalent concentration of non-immune mouse IgG 1 (Dako), overnight at 4° C. The specimens were washed three times with PBS, incubated with biotinylated rabbit anti-mouse secondary antibody (1:100 dilution in PBS; Dako), washed three times in PBS and treated with streptavidin-FITC conjugate, (1:100 dilution in PBS; 60 minutes; Amersham). The sections were washed three times in PBS and viewed by confocal microscopy.

Co-Localisation of N1 and Fibronectin-EDA in Immature Bovine Cartilage.

Sections were blocked and the two primary antibody incubations combined, (as described above). Detection was carried out using a rabbit anti-goat-FITC conjugated secondary antibody (Dako) for N1 and a biotinylated rabbit anti-mouse secondary antibody followed by a streptavidin-Texas Red conjugate (Amersham Pharmacia) for fibronectin-EDA.

Results

Immunolocalisation of NI.

N1 expression, (green), was shown to be almost entirely confined to the upper 2-3 cell layers of the superficial zone of neonatal bovine articular cartilage (FIGS. 1.1 and 1.2). Cells that do not expressed N1 are counterstained red by propidium iodide. Arrows indicate the articular surface.

Immunolocalisation of Fibronectin-EDA.

Results showed that fibronectin-EDA expression is cell associated and almost entirely confined to the superficial zone of the articular cartilage, (FIG. 1.3). Small amounts of fluorescence can be seen in the mid zone, (FIG. 1.4), although this was also seen on the control sections, (FIG. 1.5), and so maybe non-specific staining. Cells that do not expressed Fibronectin-EDA are counterstained red by propidium iodide. Arrows indicate the articular surface.

Co-Localisation of N1 and Fibronectin-EDA in Immature Bovine Cartilage.

FIGS. 1.6, 1.7 and 1.8 show N1 immunolocalisation, fibronectin-EDA immunolocalisation and an overlay of the two images respectively. Arrows illustrate the articular surface. The overlay illustrates that the cells expressing N1 also express fibronectin-EDA. Control images showed no fluorescence (images not shown).

Discussion

These results are consistent with the hypothesis that a population of Notch positive and fibronectin-EDA positive chondroprogenitor cells exists within the superficial zone of healthy articular cartilage. Notch and fibronectin-EDA have been previously recognised as markers for precursor cells in non cartilaginous tissues. The Notch receptor forms part of a signalling system that alters transcription factor expression within a cell, preventing it from differentiating. Fibronectin-EDA has been described as the 'onco-foetal' form of fibronectin because it is produced in situations where precursor cells or undifferentiated cells abound, (e.g. embryonic development, wound repair and tumour formation). It is possible that fibronectin-EDA may be a component of a 'stem-cell niche', a region of specialised extracellular matrix that supports early progenitor cells. The co-localisation experiment showed that the two markers were expressed simultaneously by cells within the superficial zone and that there was no discernable pattern of singly labelled cells. This is inconsistent with the hypothesis that Notch and fibronectin-EDA label two distinct or overlapping stages in chondrocyte differentiation and instead indicate that superficial zone chondroprogenitor cells are a largely homogeneous population of cells exist within the superficial zone.

Example 1.2

In Vitro Characterisation of Superficial Zone Chondrocytes

Methods

Isolation of Superficial, Intermediate and Deep Zone Cells from Bovine Articular Cartilage.

Superficial, mid and deep zone cartilage were dissected from neonatal bovine metatarsophalangeal joints and the chondrocytes released by sequential digestion in pronase (0.1% in DMEM/5% FCS; 3 hours; Merck, $4\times10^6$ units/g) and collagenase, (0.04% in DMEM/5% FCS; 16 hours with gentle shaking; Worthington, 237 U/mg). Tissue digests were strained, (70 µm cell strainer; Falcon), centrifuged, (1000 rpm; 5 min), washed with serum free DMEM, (10 ml), re-centrifuged and resuspended in serum free DMEM.

Production of Fibronectin-Coated Culture Plastic.

24 well culture plates and 35 mm Petri dishes were coated with bovine plasma fibronectin, (10 µgml$^{-1}$ in Dulbecco's PBS with 1 mM MgCl$_2$ and 1 mM CaCl$_2$; 16 h; 4° C.) or vehicle, and blocked with 1% BSA.

Cell Adhesion to Fibronectin and PBS-Coated Dishes.

Superficial, mid and deep zone articular chondrocytes, (4000 cells/Petri dish) were seeded onto fibronectin (FI-BRONECTIN, 10 µgml$^{-1}$) or PBS-coated 35 mm dishes for 20 minutes. The non-adherent cells were removed and placed onto fresh FIBRONECTIN or PBS coated-dishes for a further 40 minutes before the non-adherent cells were once again removed.

Colony Forming Efficiency of Surface, Middle and Deep Zone Chondrocytes Subjected to Differential Adhesion on Fibronectin for 20 and 40 Minutes.

Superficial, mid and deep zone articular chondrocytes (4000 cells/Petri dish) were seeded onto fibronectin (FI-BRONECTIN, 10 µgml$^{-1}$) or PBS coated dishes for 20 minutes and non-adherent cells removed and seeded onto similarly treated dishes for 40 minutes before removal of non-adherent cells. The number of colonies formed, (>4 cells), was assessed after 6 and 10 days in culture and expressed as the 'colony forming efficiency', (i.e. number of colonies/initial number of adherent cells).

Analysis of Differential Integrin and N1 Expression by Superficial Zone Chondrocytes Using Fluorescent Activated Cell Sorter (FACS) Analysis.

Petri dishes (35 mm) were coated with 10 µg ml$^{-1}$ bovine fibronectin (Sigma, UK) in PBS containing 1 mM MgCl$_2$ and 1 mM CaCl$_2$ (PBS+) overnight at 4° C. Dishes were blocked with 1% BSA in PBS+ before chondrocytes were added. Control dishes were treated with PBS+ overnight at 4° C. Chondrocytes were isolated from the surface, middle and deep zone articular cartilage of 7 day old calves as previously described. After isolation, chondrocytes (4,000 ml$^{-1}$) were seeded onto 35 mm plastic dishes at 37° C. for 20 minutes in DMEM containing 0.1% Gentamycin. After 20 minutes, media (and non-adherent cells) was removed and placed in a second dish for 40 minutes at 37° C. before this media (and non-adherent cells) was removed and placed in a third dish. After removal of media at 20 and 40 minutes, fresh DMEM containing gentamycin and 1% FCS was added to the remaining adherent cells which were maintained in culture for up to 10 days.

Immediately following sequential pronase/collagenase isolation and at various time points after differential adhesion, chondrocytes were removed from dishes non-enzymatically and resuspended at 1×10$^6$ cells ml$^{-1}$ in PBS. 2×10$^5$ cells were incubated for 3 hours with antibodies to α5 and β1 integrin subunits and N1 at room temperature. Cells were centrifuged at 2,500 rpm, supernatants removed and cells washed three times in PBS with centrifugation between each wash. Cells were then incubated with relevant FITC conjugated secondary antibodies for 1 hour at room temperature and washed three times in PBS as described above. Finally, labelled cells were resuspended in 200 µl PBS and subjected to single channel FACS analysis.

Measurement of Average Cell Size of Superficial, Mid and Deep Zone Chondrocytes.

Superficial (SZC), middle (MZC) and deep zone chondrocytes (DZC) were isolated from the articular cartilage of 1-3 week old bovine metatarsophalangeal joints using fine dissection and sequential pronase/collagenase digestion. Aliquots of the isolated cell suspensions were pipetted onto a haemocytometer and coverslipped. Cells were viewed using an inverted Olympus CK40 microscope and photographed at ×10 magnification ensuring sufficient cells were present in the image (n>120). Image analysis using Image-Pro plus software calibrated with a graticule was carried out to determine the average diameter of cells present in the image.

Results

Colony Formation by 'Fast-Fibronectin Binding', Superficial Zone Chondrocytes.

Initial cell-adhesion to fibronectin-coated tissue culture plastic, expressed as the percentage of cells added that were bound after 3-4 hours, is shown in table 1.

TABLE 1 1

Superficial, mid and deep zone chondrocyte adhesion to fibronectin and PBS coated tissue culture plastic.

| Adhesion Time | Surface. FIBRONECTIN | Surface. PBS | Mid. FIBRONECTIN | Mid. PBS | Deep. FIBRONECTIN | De p. PBS |
|---|---|---|---|---|---|---|
| 20 minutes | 9.05% +/− 0.44 * *** | 3.83% +/− 0.27 | 14.53% +/− 0.86 ** ^^ | 3.94% +/− 0.19 | 3.59% +/− 0.22 | 3.68% +/− 0.23 |
| 40 minutes | 4.89% +/− 0.43 | 4.12% +/− 0.34 | 10.85% +/− 0.51 | 4.2% +/− 0.19 | 3.95% +/− 0.30 | 4.21% +/− 0.36 |

*, $p < 0.001$ compared with 40 minutes;
**, $p < 0.01$ compared with 40 minutes;
***, $p < 0.001$ compared with PBS control;
^ $p < 0.01$ compared with surface FIBRONECTIN 20;
^^, $p < 0.001$ compared with deep FIBRONECTIN 20.

The number of colonies, (>4 cells), formed by the adherent cells was assessed after 6 and 10 days in culture and expressed as the 'colony forming efficiency', (i.e. number of colonies/initial number of adherent cells). The colony forming efficiency of the 'fast-fibronectin binding', superficial zone cells were significantly higher than that observed amongst the other groups of chondrocytes, (see FIG. 1.9. *=p<0.01). FIG. 1.10 shows a photomicrograph of colonies formed by the 'fast-fibronectin binding' superficial zone cells.

Analysis of Differential Notch-1 Expression by Chondrocytes Using FACS Analysis.

Chondrocytes were isolated from surface, middle and deep zone articular cartilage from 7 day old calves using sequential pronase/collagenase digestion overnight at 37° C., washed in PBS and subjected to FACS analysis using anti-N1 polyclonal antibody. Approximately 75% of surface zone, 10% of middle and 25% of deep zone cells were positive for N1 immediately after isolation from the tissue, (FIG. 1.11).

Magnetic Bead Separation of Notch Positive Cells.

N1 immunopositive SZC, MZC and DZC were isolated using anti-N1 antibody coated magnetic Dynabeads, cultured for 6 days and colony forming efficiency assessed. There were significantly ($p<0.001$) more colonies from N1 positive surface zone cells than from N1 positive middle and deep zone cells (FIG. 1.12).

Analysis of Differential Integrin Expression by SZC Using FACS.

After differential adhesion, SZC, MZC and DZC expressed $\alpha 5$ and $\beta 1$ subunits at all time points analysed regardless of substrate although differences in labelling intensity and the number of labelled cells were noted. Using flow cytometry immediately after isolation and 4 hours after differential adhesion, $\beta 1$ subunits were shown to be preferentially expressed by SZC (79% +ve) compared with MZC (5%) and DZC (2.5%). No difference in $\alpha 5$ subunit expression was detected in chondrocytes and levels of expression ranged from 88 to 67% from surface to deep. Following differential adhesion to fibronectin and culture for 72 hours, no difference in chondrocyte $\alpha 5$ and $\beta 1$ subunit expression was detected regardless of tissue depth. The overall expression of $\alpha 5$ and $\beta 1$ subunits was however decreased in chondrocytes from all tissue depths relative to expression 4 hours after differential adhesion, (FIG. 1.13).

TABLE 2

|  | Alpha 5<br>4 hours | Beta 1<br>4 hours | Alpha 5<br>72 hours | Beta 1<br>72 hours |
|---|---|---|---|---|
| Surface | 88.64 +/− 4.30 | 76.16 +/− 4.8 | 40.95 +/− 2.9 | 43.01 +/− 3.8 |
| Middle | 69.02 +/− 3.2 | 5.16 +/− 5.2 | 26.68 +/− 4.1 | 40 +/− 4.2 |
| Deep | 67.32 +/− 2.4 | 2.52 +/− 3.7 | 34.46 +/− 3.9 | 27.12 +/− |

Measurement of average cell size of SZC, MZC and DZC.

FIG. 1.14 illustrates the average cell diameter of superficial (n=124), middle (n=275) and deep zone (n=182) chondrocytes. There was a significant difference in diameters between both SZC and MZC ($p>0.05$) and SZC and DZC ($p>0.005$). This data demonstrates that cells from the superficial zone of immature bovine cartilage have, on average, a smaller diameter than mid and deep zone cells. FIGS. 1.15a, 1.15b and 1.15c are representative photographs of a superficial zone cell, middle zone cell and deep zone cell respectively viewed using phase contrast optics (magnification ×200).

Discussion

These results show that a population of colony forming chondrocytes exists within the superficial zone of articular cartilage. Colony formation in vitro is the definitive test for a progenitor cells because it proves that the cells have a high capacity for repeated cell division, (i.e. they are self-renewing). These results therefore show that there are progenitor cells within the superficial zone. The colony forming superficial zone cells were shown to have a high affinity for fibronectin, an observation that was presumed to be related to the expression of high levels of $\alpha_5 \beta_1$ integrin within the superficial zone. The difference in $\beta_1$ integrin expression between the superficial and mid/deep zones was particularly striking. FACS analysis confirmed that Notch expression was concentrated amongst superficial zone cells, whilst morphological analysis indicated that the superficial zone cells were smaller than other chondrocytes. Together these results show that the superficial zone cells are a distinct population of cells with different characteristics to other chondrocytes.

Importantly, the results show that anti-Notch antibodies could be used to selectively bind the Notch positive cells to the surface of a biomaterial, thereby concentrating the colony forming, progenitor cells on the surface of a particulate material. Likewise, anti-integrin $\beta_1$ antibody could be used to selectively bind chondroprogenitor cells to the surface of a biomaterial. The high affinity of the colony forming cells for fibronectin suggests that fibronectin could also be used to bind the colony forming chondroprogenitor cells to the surface of a biomaterial. Such selective affinity between cells and biomaterial could be applied in the formation of a cartilage implant in which chondroprogenitor cells were concentrated in the same anatomical position as occurs within normal cartilage.

Example 1.3

In Vitro Cartilage Formation by Pellet Cultures of SZC with a High Affinity for Fibronectin Methods Pellet Culture of 'Fast-Fibronectin Binding' SZC.

Pellet culture is an established method that allows chondrogenic cells to form cartilage in vitro (Nishimura et al, 1999).

Superficial zone and middle zone articular cartilage were obtained from 1-3 week old bovine metatarsophalangeal joints by fine dissection. Cartilage shavings were digested in pronase (0.1% in DMEM/5% FCS; 37° C. for 3 hours; Merck, 4×10 units/g), washed in PBS, and suspensions of superficial zone and middle zone cells isolated using collagenase, (0.04% in DMEM/5% FCS; 16 hours at 37° C. with gentle shaking; Worthington type II, 237 U/mg). The released cells were strained through a 70 μm cell strainer (Falcon), centrifuged, (1000 rpm; 5 minutes), washed in serum free DMEM, counted using a haemocytometer and diluted to 1×10⁶ cells/ml.

The wells of a 6 well plate were coated with bovine plasma fibronectin, (10 μg/ml in Dulbecco's PBS with 1 mM $MgCl_2$ and 1 mM $CaCl_2$; 16 hours at 4° C.; Sigma). The fibronectin solution was aspirated and the plates blocked with BSA (1% w/v; 1 hour).

SZC or MZC, (2×10⁶ cells in serum free DMEM; 2 ml) were seeded onto the fibronectin-coated wells and incubated at 37° C. for 20 minutes. The media was then gently swirled and discarded, and the adherent, 'fast-binding' cells incubated in DMEM/10% FCS at 37° C. in an atmosphere of 5% humidified $CO_2$ for 96 hours. The 'fast-binding' superficial and mid zone cells were trypsinised and aliquoted, (500 k cells), to sterile 2 ml round bottomed centrifuge tubes, (Epindorf), in 0.5 ml DMEM supplemented with pyruvate (Sigma); ITS, (1%; Sigma); ascorbate-2-phosphate, (100 μM; Sigma); dexamethasone. ($10^{-7}$M; Sigma), HEPES, (20 μg/ml; 1M; Sigma) and transforming growth factor $\beta 1$, (10 ng/ml; R+D systems). The tubes were centrifuged, (2500 rpm; 10 minutes), and incubated at 37° C. in a humidified atmosphere of 5% $CO_2$ for 7, 14 and 21 days with a media change every 2 days.

Histological Analysis.

At the end of the incubation period, the medium was removed and the samples fixed in 10% formal buffered saline, (0.5 ml; 24 hours), processed on the VIP processor, wax embedded, sectioned on a Leica microtome (5 µm). For histological analysis, specimens were dewaxed, rehydrated and stained with either Safranin O, (0.1%, 6 minutes), Picrosirius Red (0.1% in saturated alcoholic picric acid, 90 minutes), Toludine Blue, (0.5%; 15 seconds), or Haematoxylin and Eosin (Gills haematoxylin, 6 min and alcoholic eosin, 4 min). Specimens were mounted using Histomount and images captured using the Leica microscope and SPOT camera and related software.

Immunocytochemical Analysis.

The slides were dewaxed, rehydrated and subjected to Dako HMAR (heat mediated antigen retrieval system; Dako). For collagen type I detection, the slides were blocked in swine serum (2.5%, 20 min at room temperature; Dako), washed thoroughly in PBS and immersed in either rabbit polyclonal anti-collagen I antibody (10 µg/ml; Biogenesis) or an equivalent concentration of non-immune rabbit IgG immunoglobulin (Dako), overnight at 4° C. The slides were then washed in PBS, immersed in swine anti-rabbit biotinylated secondary antibody (1:100; room temperature for 30 min; Dako), washed in PBS, immersed in Strepavidin Texas Red (1:100, room temperature for 30 min; Amersham Pharmacia Biotech), washed in PBS, mounted using Vectormount for fluorescence and coverslipped.

For collagen type II detection, the slides were blocked in rabbit serum (2.5%, 20 min at room temperature; Dako), washed thoroughly in PBS and immersed in either mouse monoclonal collagen II primary antibody (1 µg/ml; Neomarkers) or an equivalent concentration of non-immune mouse IgG immunoglobulin (Dako) overnight at 4° C. The slides were then washed in PBS, immersed in rabbit anti-mouse biotinylated secondary antibody (1:100; room temperature for 30 min; Dako), washed thoroughly in PBS, immersed in Strepavidin FITC (1:100; room temperature for 30 min; Amersham Pharmacia Biotech), washed thoroughly in PBS, mounted using Vectormount for fluorescence and coverslipped.

For the detection of the glycosaminoglycan epitopes chondroitin 4 sulphate, chondroitin 6 sulphate and dermatan sulphate, the sections were wetted with PBS containing 0.1% Tween 20 (Sigma), digested with either (i) chondroitinase AC (0.25 u/ml), (ii) chondroitinase ABC (0.25 u/ml) or (iii) chondroitinase ABC (0.25 u/ml) for 1 hour at 37° C., washed with PBS/Tween 20 and incubated with the appropriate blocking serum for 30 minutes at room temperature. The blocking serum was then wicked off and the sections incubated in either (i) antibody 2B6, (1 in 500; recognizes chondroitin 4 sulphate GAG stubs after chondroitinase AC treatment; Caterson et al., 1985); (ii) antibody 2B6, (1 in 500; recognises dermatan sulphate GAG stubs after chondroitinase ABC treatment; Caterson et al., 1985), or (iii) antibody 3B3+, (1 in 500; recognises chondroitin 6 sulphate stubs after chondroitinase ABC treatment; Couchman et al., 1984). The slides were washed in PBS/Tween 20 and antibody binding detected using a relevant fluorescent conjugated antibody diluted with PBS containing 20% FCS for 1 hour at room temperature and then washed with PBS.

For the detection of Link protein, the sections were wetted with PBS containing 0.1% Tween 20 (Sigma), digested with chondroitinase AC (0.25 u/ml) plus chondroitinase ABC (0.25 u/ml) for 1 hour at 37° C., washed with PBS/Tween 20 and incubated in blocking serum for 30 minutes at room temperature. The blocking was serum wicked off and the sections incubated in either polyclonal anti-link protein antibody, (1 in 30) or an equivalent concentration of non-immune serum. The slides were washed in PBS/Tween 20 and antibody binding detected using a relevant fluorescent conjugated antibody diluted with PBS containing 20% FCS for 1 hour at room temperature and then washed with PBS.

The slides were viewed and images captured using the Leica microscope with the Spot camera and related software.

Results and Discussion

Histological Investigation.

H+E staining of 'fast-binding' superficial zone chondrocyte pellets showed the presence of morphologically normal and viable cells throughout the specimens (FIG. 1.16). Picrosirius red showed collagen deposition, especially in the territorial matrix surrounding the cells, (FIG. 1.17). Safranin O staining for glycosaminoglycans showed intense dark orange staining of the extracellular matrix produced by the cells, indicating that the cells had secreted a proteoglycan-rich matrix, (FIG. 1.18). This result was confirmed by the toluidine blue stained specimens, in which the matrix was stained purple/blue, again indicative of glycosaminoglycan production. Taken together these results indicate that pellet cultures of 'fast-binding' superficial zone cells secrete a matrix with the histological features of normal cartilage.

Immunocytochemical Investigation.

Immunocytochemistry showed that the cells were synthesising cartilage specific matrix components in pellet culture. The extracellular matrix in the pellets contained collagen type II (FIG. 1.19), but not collagen type I, (FIG. 1.20), indicating that the cells had differentiated to form chondrocytes and that de-differentiation had not occurred.

Immunostaining showed the presence of chondroitin 4 sulphate and chondroitin 6 sulphate in the matrix of the pellet cultures (FIGS. 1.21 and 1.22). Taken together with the results from the safranin O and toluidine blue histochemical staining, these data show that the cells are secreting significant quantities of cartilage-matrix-like proteoglycans. This is confirmed by the presence of link protein, (FIG. 1.23), a component of the major cartilage structural component aggrecan.

Overall these results indicate that fast fibronectin binding superficial zone cells grown in pellet culture produce the two major structural components of articular cartilage, collagen II and aggrecan. This indicates that fast fibronectin binding superficial zone cells are chondrogenic.

Taken together with the results from Examples 1.1 and 1.2, these results indicate that a population of chondrogenic, colony forming chondroprogenitor cells exist within the superficial zone of articular cartilage and that these cells will bind rapidly/selectively to a biomaterial coated with either (i) fibronectin and/or (ii) anti-N1 antibody and/or (iii) anti-integrin $\beta_1$ antibody. Such selective cell binding could be used to create a zoned implant in which the precursor cells and more mature chondrocytes are in their correct anatomical positions.

Generalising from these results, we predicted that any extracellular matrix component or antibody that will selectively bind either chondroprogenitor cells or other chondrogenic mesenchymal precursor cells could be attached to the surface of a biocompatible implant material and be used to (i) bind chondroprogenitor cells and (ii) localise them to selected regions of an implant designed for use in cartilage repair.

Example 14

Effect of Transplanting Chondrocytes Pellets onto Wounded Articular Cartilage

Method

Pellets of superficial zone chondrocytes with a high affinity for fibronectin and pellets of mid and deep zone chondrocytes were cultured for 7 days and implanted into bovine cartilage explants containing a partial depth wound. After a further 7 days, explants were incubated with ethidium homodimer, (90 min), and either (i) fixed with 10% NBFS, wax embedded, sectioned and stained with Safranin O or (ii) dewaxed and examined under fluorescence optics to assess cell death.

Results and Discussion

Control explants, (which received no pellet), and explants which received pellets from mid and deep zone cartilage exhibited a distinct loss of matrix from both the wound margin and the articular surface. Cell death was also evident along the wound margin and the articular surface in control samples and those receiving mid and deep zone pellets. In contrast, explants receiving a pellet derived from surface zone articular cartilage showed reduced loss of matrix from the wound margin and reduced cell death. It was concluded that N1 positive, colony forming superficial zone cells may play an important role in chondrocyte formation and repair.

Example 1.5

Chondroprogenitor Cells Injected into Chick Embryos: In Ovo Chondroprogenitor Cell Tracing Using CFDA SE Materials and Methods SZC and DZC were isolated from 7 day old bovine articular cartilage using sequential pronase/collagenase digestion and $5 \times 10^6$ cells subjected to differential adhesion to FIBRONECTIN in 60 mm dishes for 20 minutes. Cells then labelled with 20 µM CFDA-SE (molecular probes; www.probes.com) in PBS for 30 minutes at 37° C. in 5% $CO_2$. Cells were washed with Serum free DMEM/F12 for 30 minutes and then incubated in 10% FCS DMEM/F12 for 48 hours. Labelled cells were trypsinised, pooled and counted and resuspended at $1^{st}$ expt $1 \times 10^5$ cells 100 µl$^{-1}$ and $2^{nd}$ expt $2.5 \times 10^5$ cells 100 µl$^{-1}$ in DMEM/F12 containing no additives whatsoever. 100 µl cell suspension were injected into the extraembryonic vessels of windowed 4 day old chick embryos. After sealing the windows with sellotape embryos were incubated for up to 6 days. Embryos were killed by cervical dislocation 3 and 6 days after injection and either fixed in 10% NBFS and wax embedded or chilled by precipitate immersion in n-hexane at −70° C.

Sections were examined using fluorescent microscopy for the presence of labelled cells.

Results

Labelled cells were observed in areas of the embryo containing developing cartilage, e.g. the otic cup, (see FIG. 1.25). Lower levels of stained cells were observed in developing tendon. These results suggest that the superficial zone cells will bind to developing cartilage. More sensitive detection of the injected cells showed clusters of the cells and the formation of ectopic cartilaginous tissue within the developing embryos. These results suggest that superficial zone cells can form cartilaginous tissue in vivo, (FIGS. 1.26 and 1.27).

Example 2

Creation of Zoned Cultures

Our examples shown there to be a population of chondroprogenitor cells in the superficial zone of immature bovine articular cartilage. These cells have been identified on the basis of their high affinity to fibronectin and colony forming efficiency. The cells have also been shown to express N1 and Fibronectin-EDA Current tissue engineering approaches make no attempt to recreate the zonal architecture of native articular cartilage. These examples show some methods for how tissue engineered cartilage constructs with distinct zonal architectures can be produced. They show examples of where differential binding materials (e.g. fibronectin) are used to produce biomaterials with chondroprogenitor cells localised to specific regions Our examples further show that the layered structure of the present invention improves cartilage repair/growth over controls.

Example 2.1

Layered Structures—Range of Options

The 'zoned' area of the culture could take on many possible forms and profiles.

One of the ideas is to recreate the structure that cartilage has at the foetal or neonatal stage as it is know that such cartilage has greater potential to heal when compared to cartilage in mature subjects. The change in chondroprogenitor concentration at the boundary zone could be either be a single step change or it could be profiled. i.e. superficial zone enriched with chondroprogenitor cells and remainder filled with mixed, mature chondrocytes. FIG. 2.1.

However it is suspected that the chondroprogenitors are much more effective at integrating implanted tissue with the native cartilage and reducing cell death around the wound margin. Lack of integration is a major factor in implant failure. Hence have designed an implant with enriched zones of chondroprogenitors around the sides as well as on the outer surface. FIG. 2.2.

Overview of the Exemplification Options.

| OPTION | CHONDROPROGENITOR CELLS | MATURE CHONDROCYTES | CELL SELECTION | SCAFFOLD |
|---|---|---|---|---|
| 1 | BMSC | Cartilage | Tissue dissection | separate parts for each zone |
| 2 | SZCs | Cartilage | CBM | separate parts for each zone |
| 3 | SZCs | Cartilage | CBM | Single scaffold internally zoned |

BMSC: bone marrow stromal cells
SZC: superficial zone chondroprogenitors
CBM: chondroprogenitor binding material.

Example 2.2

Introduction

This embodiment combines a fibrous scaffold, two classes of coated-particulate biomaterials and cells harvested from an autologous osteochondral plug to form a layered, fibre-reinforced cartilage implant, (~1.5 cm diameter and 4 mm thick), in which (i) a layer of chondroprogenitor cells are concentrated near the articular surface of the device, (i.e. within the superficial zone) and (ii) a layer of more mature chondrocytes are concentrated closer to the sub-chondral bone, (i.e. in the mid and deep zones; see FIG. 2.16). The method produces a construct with a volume 18.4 fold greater than that of the original harvested tissue.

Bone Marrow Stromal Cell Isolation
Method

Neonatal bovine metatarsophalangeal joints were opened aseptically and a 3.5 mm diameter×5 mm deep osteochondral plug extracted manually from the articular surface using an Acufex cylindrical chisel. Bone marrow stromal cells were obtained from the osseous portion of the osteochondral plug. The bone was separated from the cartilage with a scalpel, fragmented into 0.08% collagenase, (Worthington type II), in DMEM/5% FCS (3 ml), agitated vigorously and incubated at 37° C. for 90 minutes to release a bone marrow cell suspension. The bone fragments were then re-agitated, the supernatant collected and combined with 3 PBS washings of the bone fragments. The pooled, collected marrow cells were centrifuged, (1000 rpm; 5 min), washed in PBS, re-centrifuged, (1000 rpm; 5 min) and the cell pellets re-suspended in DMEM/10% FCS (5 ml). The released cells were incubated in the well of a 6 well plate at 37° C. in a humidified atmosphere of 5% $CO_2$ until the adherent cells became confluent, (typically 6 days). The adherent fibroblastic cells were washed with PBS to remove the non-adherent haematopoietic cells and debris and the fibroblastic cells harvested using trypsin.

The harvested, ('first passage'), bone marrow stromal cells obtained from a single osteochondral plug were used to seed 4.125 mg of cell-adhesion factor coated-sulphated Intrasite, sufficient to produce one layer of a bilayered construct.

Results

The freshly plated marrow cell isolates consisted of large numbers of red blood cells, non-adherent haematopoietic cells, debris and occasional adherent fibroblastic and macrophage-like cells. When cultured on tissue culture plastic the adherent fibroblastic cells proliferated rapidly, thereby increasing the number of available chondroprogenitor cells. A typical culture derived from a 3.5 mm osteochondral plug produced a confluent 10 $cm^2$ monolayer of bone marrow stromal cells after ~6 days. (Generally 500,000-750,000 harvested cells).

Isolation of Neonatal Bovine Chondrocytes
Method

Neonatal bovine metatarsophalangeal joints were opened aseptically and a 3.5 mm diameter×5 mm deep osteochondral plug extracted manually from the articular surface using an Acufex cylindrical chisel. Chondrocytes were obtained from the upper, cartilaginous portion of the plug. The cartilage was cut from the bone, sliced and transferred to a bijou containing collagenase, (0.1%; 3 ml; Worthington class II), in DMEM supplemented with penicillin, streptomycin, non-essential amino acids, L-glutamine, (Sigma, as above) and 5% foetal calf serum, (Sigma; DMEM/5% FCS). The tissue was digested for 16 hours at 37° C. in a humidified atmosphere of 5% $CO_2$ with gentle mixing to release a suspension of chondrocytes. The released cells were filtered through a 70 μm nylon mesh, (Falcon), diluted to 10 ml with DMEM/10% FCS, centrifuged, (1000 rpm; 5 min), the supernatant discarded and the washing step repeated.

The chondrocytes obtained from the cartilage of a single osteochondral plug were used to seed 4.125 mg of cell-adhesion factor coated-sulphated Intrasite, sufficient to produce one layer of a bilayered construct.

Results 3.5 mm diameter cartilage plugs released 668±85×$10^3$ chondrocytes. (Typically 500-900×$10^3$ cells per explant).

Preparation and Coating of Sulphated Intrasite with Plasma Fibronectin or Mixtures of Cell Attachment Molecules Adsorbed from FCS Sulphated Intrasite gel (4.125 mg per layer of construct; 6.5 mg/ml in PBS) was prepared and sterilised as described in Example 4. Serum free DMEM was prepared by mixing DMEM, (500 ml), penicillin and streptomycin (Sigma; 5 ml); non essential amino acids, (Sigma 5 ml) and L-glutamine, (Sigma; 5 ml).

Autoclaved sulphated Intrasite was diluted to 40 ml with PBS, centrifuged, (2500 rpm; 5 min), 30 ml supernatant removed and 30 ml serum-free DMEM added. The tubes were centrifuged, (2500 rpm; 5 min) and the supernatant removed to leave the biomaterial in 2.5 ml of liquid. Cell attachment factors, (e.g. plasma fibronectin; 60 μg/ml), PBS vehicle or foetal calf serum (10%) was added and the tubes mixed vigorously for 2 hours at 4° C.

Bone Marrow Stromal Cell Attachment and Growth Upon Plasma Fibronectin Coated Sulphated Intrasite
Method Ascorbate 2 phosphate (25 μg/ml final; Sigma) was dissolved in DMEM, (Sigma), filter sterilised, (0.2 μm; Sartorius) and added to DMEM supplemented with, penicillin, streptomycin, non-essential amino acids, L-glutamine and 10% foetal calf serum (DMEM/10% FCS/ASCP).

The trypsinised bone marrow stromal cells obtained from a 3.5 mm diameter osteochondral plug were added to plasma fibronectin-coated sulphated Intrasite gel, (4.125 mg), in DMEM/10% FCS/ASCP (20 ml). The cultures were mixed occasionally for the first 2 hours to produce more even seeding and then incubated at 37° C. in a humidified atmosphere of 5% $CO_2$ for 10 days.

The viability of bone marrow stromal cells growing upon fibronectin coated sulphated Intrasite was assessed by adding MTT (1 mg/ml; Sigma) to the culture media for 2.5 hours, washing the samples in PBS and viewing the cells by phase contrast microscopy. Additionally, cell viability was determined by adding calcein AM, (0.6 μl/ml; 1 mg ml; 90 min; Molecular Probes), washing the cells in PBS and viewing the specimens using a Leica confocal microscope.

The deposition of a collagenous matrix was assessed using the histological stain picro sirius red. Samples of the cell seeded biomaterial, (200 μl) were fixed with phosphate buffered formalin, washed with PBS, (2×3 ml) and stained with picrosirius red, (1 ml, 30 min; 0.1 g sirius red in 100 ml saturated aqueous picric acid; Sigma). Samples were washed repeatedly for 16 hours in PBS to remove non specifically bound stain and viewed by microscopy.

Collagen type I and collagen type II production was determined by immunocytochemistry. Bone marrow stromal cell seeded, fibronectin coated sulphated Intrasite was incubated in 20 ml DMEM/10% FCS/ASCP for 10 days, washed 3 times in PBS, (10 ml; centrifuged 2500 rpm; 5 min) and fixed in methanol, (−20° C.; 10 min). The samples were washed twice with PBS, (10 ml; centrifuged 2500 rpm; 5 min), blocked with BSA, (3% w/v in PBS; 5 ml; 1 hour at 37° C.) and washed 3 times in PBS. The specimens were then incubated with anti collagen antibodies or equivalent concentrations and volumes of non immune immunoglobulins for 1 hour at 37° C., (i.e. either rabbit anti type I collagen antibody, (20 µl diluted 1 in 10 with PBS; 200 µl; Biogenesis); non immune rabbit serum control, (diluted 1 in 2000 with PBS; 200 µl; Dako); mouse anti type II collagen antibody, (diluted 1 in 200; 500 µl; New Markers) or non immune mouse serum, (diluted 1 in 100; 500 µl; Dako). The specimens were then washed 3 times in PBS. Anti collagen type I antibodies were visualised by incubating the specimens and their controls with swine anti-rabbit immunoglobulin FITC, (10 µl in 1 ml PBS; Dako), plus 'Dead cell stain', (2 µl; Molecular Probes), for 1 hour at 37° C.

Anti collagen type II antibodies were visualised by incubating the specimens or their controls with biotinylated rabbit anti-mouse immunoglobulin, (1 in 100 in PBS; Dako), for 30 minutes at 37° C., washing 3 times in PBS and incubating in streptavidin FITC, (diluted 1 in 100 in PBS; Amersham) plus 'Dead cell stain', (2 µl; Molecular Probes), for 30 minutes at 37° C.

Samples were washed 3 times in PBS and viewed using a Leica microscope and Spot camera.

Results

Bone marrow stromal cells adhered to cell-adhesion factor coated sulphated Intrasite within 16 hours, (FIG. 2.3) and proliferated, to first cover the surface of the particulate biomaterial and then to aggregate it into macroscopic clusters of cells, biomaterial and extracellular matrix components. Calcien AM staining revealed a population of adherent cells upon the surface of the material after 4 days, (FIG. 2.4), whilst picro sirius red showed the deposition of a collagenous matrix after 7 days in culture, (FIG. 2.5).

Immunocytochemistry showed type I collagen production in specimens of bone marrow stromal cells cultured on fibronectin coated sulphated Intrasite after 10 days, (FIG. 2.6). No evidence of collagen II production was observed, (FIG. 2.7).

Neonatal Bovine Chondrocyte Attachment and Growth Upon Sulphated Intrasite Coated with Cell Adhesion Factors Adsorbed from Foetal Calf Serum.

Method

Ascorbate 2 phosphate (25 µg/ml final; Sigma) was dissolved in DMEM, (Sigma), filter sterilised, (0.2 µm; Sartorius) and added to DMEM supplemented with, penicillin, streptomycin, non-essential amino acids, L-glutamine and 10% foetal calf serum (DMEM/10% FCS/ASCP).

Sulphated Intrasite gel, (4.125 mg), was coated with cell attachment factors adsorbed from foetal calf serum. Bovine neonatal chondrocytes were obtained from the cartilaginous portion of a 3.5 mm diameter osteochondral plug. The cells and coated gel were combined in DMEM/10% FCS/ASCP (20 ml) and incubated at 37° C. in a humidified atmosphere of 5% $CO_2$ for up to 27 days. The cultures were mixed occasionally for the first 2 hours to produce more even seeding.

Cell viability was confirmed by incubating the cell seeded material with MTT (1 mg/ml; Sigma), for 2 hours, and fixing the samples with phosphate buffered formalin, (2 ml; 15 min). The tubes were washed with PBS, (2×5 min; 10 ml; centrifuged 2500 rpm; 5 min) and Safranin O, (0.1% aqueous 1 ml) added for 2.5 hours. The samples were washed three times with PBS and stored for 16 hours in PBS at 4° C. to allow non-specifically bound dye to elute. The samples were washed twice in PBS, transferred to microscope slides and viewed using the Leica microscope. Images were grabbed using the Spot camera.

The deposition of a collagenous matrix was assessed using the histological stain picro sirius red. Samples of the cell seeded biomaterial, (200 µl) were fixed with phosphate buffered formalin, washed with PBS, (2×3 ml) and stained with picrosirius red, (1 ml, 30 min; 0.1 g sirius red in 100 ml saturated aqueous picric acid; Sigma). Samples were washed repeatedly for 16 hours in PBS to remove non specifically bound stain and viewed by microscopy.

Collagen types I, II and VI production were assessed by immunocytochemistry.

Collagen type II production was assessed by washing chondrocyte seeded, coated sulphated Intrasite three times in PBS, fixing the samples in methanol, (−20° C.; 10 min), and washing the specimens three times in PBS. BSA, (3% w/v in PBS; 10 ml) was then added to the tubes for 1 hour at 37° C. The gels were washed three times in PBS and treated with either mouse anti bovine type II collagen antibody, (1 in 200 dilution in PBS; 500 µl; Neomarkers) or an equivalent concentration of non immune mouse immunoglobulins, (1 in 100 dilution; 500 µl; Dako) for 1 hour at 37° C. The tubes were washed three times in PBS and biotinylated rabbit anti mouse immunoglobulins added, (1 in 100 dilution in PBS; 500 µl; Dako). The tubes were washed in PBS three times and streptavidin FITC (1 in 100 in PBS; 500 µl; Amersham), plus 'dead cell stain', (2 µl; Molecular probes) added for 30 minutes. Samples were washed three times with PBS and viewed using the Leica microscope and spot camera.

Collagen type VI production was demonstrated by washing chondrocyte seeded, coated sulphated Intrasite three times with PBS and blocking by dispersing the material into BSA, (3% w/v in PBS; 10 ml; 1 hour; Sigma). The material was washed three times in PBS, the supernatant removed and the samples incubated in either rabbit anti human collagen VI (1 in 50 dilution in PBS; Abcam) or an equivalent concentration of non immune rabbit IgG (1 in 1000 in PBS; Dako) for 1 hour at 37° C. The samples were washed three times with PBS and incubated in FITC-labelled swine anti-rabbit immunoglobulin, (1 in 100 dilution; 1 hour; 37° C.; Dako). The samples were washed three times in PBS and viewed by confocal microscopy.

Collagen type I production was assessed by washing chondrocyte seeded, coated sulphated Intrasite three times in PBS, fixing the samples in methanol, (−20° C.; 10 min), and washing the specimens three times in PBS. BSA, (3% w/v in PBS; 10 ml) was then added to the tubes for 1 hour at 37° C. The gels were washed three times in PBS and treated with either rabbit anti bovine type I collagen antibody, (diluted 1 in 10 with PBS; 200 µl; Biogenesis) or an equivalent concentration of non-immune rabbit immunoglobulin, (diluted 1 in 2000 with PBS; 200 µl; Dako) for 1 hour at 37° C. The tubes were washed three times in PBS and incubated in FITC labelled swine anti rabbit immunoglobulin, (1 in 100 dilution in PBS; Dako) plus EtBrHD, (2 µl; Molecular probes) for 1 hour at 37° C. The samples were washed three times in PBS and viewed using a Leica microscope and Spot camera.

Results

Chondrocytes adhered to the coated sulphated Intrasite particles and proliferated upon them to form aggregates of cells, biomaterial and extracellular matrix components. Macroscopically, the aggregates formed by the chondrocytes were larger than those formed by the stromal cells, suggesting that they were synthesising more matrix. MTT staining showed viable cells throughout the aggregates, both upon the surface of the material particles and in the spaces between them (FIG. 2.8). Picro sirius red showed that the cells had deposited a collagenous matrix within the aggregates (FIG. 2.9a). The cells within the aggregates had a rounded morphology, consistent with the retention of chondrocytic phenotype.

Immunocytochemistry revealed that the chondrocytes expressed the cartilage specific form of collagen, collagen type I, (FIG. 2.9b). This finding confirmed that the cells growing upon the coated biomaterial had retained their chondrocytic phenotype in culture. Immunocytochemistry also revealed that the chondrocytes were secreting collagen VI into their pericellular matrix, (FIG. 2.10). This molecule is an important component of a mature chondrocytes immediate surroundings and is thought to link the cell to the matrix.

Importantly, immunocytochemistry showed that the chondrocytes were not producing collagen I, even after 27 days in culture, (FIG. 2.11). This finding indicated that the chondrocytes were not de-differentiating during either the early stages of culture (when the cells were proliferating rapidly) or at later time points.

Quantification of Ovine Chondrocyte Growth Rates Upon FCS Pre-Treated Sulphated Intrasite and FCS Pre-Treated DxS Sulphated Intrasite gel (100 mg) or Dextran sulphate beads (100 mg; DxS; Sigma) were rehydrated with PBS (15.38 ml) and sterilised by autoclaving, (121° C.; 15 min). Ovine articular chondrocytes were isolated from fresh cartilage using collagenase, (0.2% Worthington's type II in DMEM/10% FCS).

The sterile gel/bead suspensions were swirled, aliquoted (10 ml) to Falcon 50 ml centrifuge tubes and diluted to 40 ml with PBS. The tubes were centrifuged, (2500 rpm, 5 min) and 30 ml supernatant discarded. The PBS washing step was repeated and 15 ml foetal calf serum, (a source of polyanion-binding, cell-attachment glycoproteins, e.g. fibronectin and vitronectin) added to the gels/beads and the tubes incubated for 2 hours. The serum pre-treated suspensions were then diluted to 40 ml with DMEM/10% FCS, centrifuged, (2500 rpm, 5 min), washed with a further aliquot of DMEM/10% FCS (30 ml), re-centrifuged and 30 ml supernatant removed.

Freshly isolated ovine chondrocytes, ($2.5 \times 10^6$ cells in 10 ml DMEM/10% FCS), were added to the serum pre-treated sulphated Intrasite gel, serum pre-treated DxS beads or Falcon tubes containing DMEM/FCS alone (10 ml) and the cultures incubated at 37° C. for 2 hours with occasional mixing. The cell-seeded particles were then aliquoted (2 ml) to groups of 10 Falcon tubes and 23 ml of DMEM/10% FCS containing ascorbate 2 phosphate (25 µg/ml) added to each tube. The cultures were capped with filter-tops and incubated on a modified Spirarack at 37° C. in a humidified atmosphere of 5% $CO_2$ for 3, 10 and 16 days.

At the end of the incubation period MTT (5 mg/ml in PBS; 400 µl) was added the tubes and to a standard curve of ovine chondrocytes and the cultures incubated for 90 minutes. The cultures were then centrifuged, (3000 rpm; 5 min), washed three times with PBS, and the supernatant removed to leave a final volume of 400 µl. Acid isopropanol, (isopropanol containing 4% 1M HCl; 1.6 ml) was added to each tube and the cultures mixed for 2 hours. Triplicate 200 µl aliquots were then collected from each tube, transferred to the wells of a 96 well plate and the absorbance read at 570 nm against a reference of 655 nm.

Results

Data showed that the ovine chondrocytes had increased in number 14.4 fold over the incubation period with the most rapid growth occurring during the first 10 days, (see FIG. 2.12). Lower rates of growth were observed in the cultures growing on serum pre-treated DxS beads or amongst chondrocytes growing in suspension culture.

Culture Equipment and Out Line Method for Bilayer Construction

The bilayered construct is formed by sequentially centrifuging (i) bone marrow stromal cell seeded, fibronectin coated sulphated Intrasite and (ii) chondrocyte seeded coated sulphated Intrasite into a scaffold to form a two layered, fibre re-enforced cell/biomaterial construct. The equipment used and outline of the method is shown in FIG. 2.13.

The tube shown in FIG. 2.13, panel (1) contains of a void-filling agar plug (2.1), which supports the scaffold during centrifugation; a mechanically robust scaffold (2.2) into which the cell seeded particulates are centrifuged to form the layered construct; an 'asymmetric collar', (2.3) which holds the scaffold in the correct position within the tube; and a quantity of culture medium (2.4) and a cap with a 0·2 µm filter to allow gas exchange (2.5). Panel 2 shows the introduction of the bone marrow stromal cell seeded, fibronectin coated sulphated Intrasite (2.6) into the culture medium. Centrifugation of the tube sediments the bone marrow stromal cell seeded, fibronectin coated sulphated Intrasite into a compact layer near the articular surface of the construct (panel 3, (2.7)). The subsequent addition of the chondrocyte-seeded, FCS coated sulphated Intrasite (2.8) is shown in panel (3). Re-centrifugation of the tube sediments the chondrocyte-seeded, FCS-coated, sulphated Intrasite (2.9) onto the layer of bone marrow stromal cell seeded, fibronectin coated sulphated Intrasite (2.7) to form a bilayer of cellular material within the scaffold, (panel 4 (2.9)). The resulting construct is removed from the tube with its collar, detached from the collar and inverted prior to implantation in a cartilage defect site. The key features of the construct are shown in an enlarged view in panel 5, namely, the articular face of the scaffold/construct; 5(2.10); the superficial zone enriched with chondroprogenitor cells, 5(2.11); the mid and deep zones populated with mature chondrocytes, 5(2.12) and the bone-facing surface of the device, 5(2.13).

Panel 6 shows the implantation of the device into a sharp-debrided, focal articular cartilage defect (6(2.14)). Panel 6(2.5) indicates the articular surface of the joint; 6(2.7) the articular cartilage; 6(2.16) the upper surface of the subchondral bone plate.

For experimental purposes the scaffold may be replaced with a 'basket' consisting of a plastic ring bonded to a 70 µm nylon mesh. This collects the sedimented cells/material pellet and maybe used as a control.

The 'asymmetric collar' is designed to hold the scaffold in the correct position within the tube and to funnel the cell-seeded material into the scaffold during centrifugation. It should be noted that much of the cell-seeded biomaterial sediments rapidly during centrifugation, (i.e. whilst the rotor is accelerating). As a consequence, the cell/material pellet is deposited away from the mid-line of the tube. The correct orientation of the 'asymmetric collar' relative to the direction of rotation of the centrifuge rotor and the radial axis of the rotor is shown in FIG. 2.14.

Demonstration of Bilayer Formation Using Two Samples of Dyed Sulphated Intrasite Gel Method Agarose, (4% w/v in PBS; Sigma) was melted by microwaving, aliquoted (5 ml) to the base of Falcon tubes and allowed to set at 4° C. A 'basket' was fitted into an 'asymmetric collar', placed upon the agar plug, and orientated as shown in FIG. 2.16 and the apparatus placed in a 60°

C. water bath. sulphated Intrasite (24.75 mg in 3.8 ml PBS) was dyed with either Safranin O, (0.1% aqueous; 1 ml) or toluidine blue, (0.01% in PBS) at 4° C. for 30 minutes. The dyed gel was then diluted with PBS (25 ml) and washed three times with PBS. The supernatant was then removed, the dyed material diluted to 6 ml with PBS and placed in a 60° C. water bath. Agarose, (1.5% in PBS), was melted by microwaving and brought to 60° C. in a water bath. Melted agarose, (22.5 ml; 1.5%; 60° C.), was added to the tube containing the asymmetric collar and 1 ml of Safranin O stained sulphated Intrasite gel carefully pipetted onto the molten agar. The tube was then capped, orientated within the centrifuge rotor and centrifuged at 2500 rpm for 5 minutes to sediment the Safranin O dyed material. The tube was then returned to the water bath and 1 ml of toluidine blue stained sulphated Intrasite carefully pipetted onto the molten agar. The tube was then re-orientated within the rotor and re-centrifuged, (2500 rpm; 5 min), to sediment the blue stained gel onto the orange stained gel. The contents of the tube were then allowed to set at 4° C. for 16 hours. The plug of agarose and sedimented, dyed-sulphated Intrasite was dissected from the basket, bisected and viewed using a dissecting microscope.

Results

FIG. 2.15 shows the deposition of a bilayer of dyed sulphated Intrasite using this apparatus and method. The orange, Safranin O dyed material forms the upper layer in the figure whilst the toluidine blue stained sulphated Intrasite forms the lower layer. The agarose plug, (which binds the particles together in this experiment), is visible in the lower portion of the photomicrograph.

Demonstration of Bilayer Formation Using Two Samples of Cell-Seeded Sulphated Intrasite Gel Method Samples of the two cell-seeded biomaterials, (i.e. (i) bone marrow stromal cell seeded, fibronectin-coated, sulphated Intrasite and (ii) chondrocyte-seeded, FCS-coated sulphated Intrasite), were centrifuged, (2500 rpm; 5 min), and the samples washed with PBS, (10 ml; 2500 rpm; 5 min). The specimens were fixed in methanol, (−20° C.; 10 ml; 10 min; Fisher), washed three times in PBS, (10 ml; 2500 rpm; 5 min), and 9 ml supernatant was removed from the tubes. The bone marrow stromal cell-seeded, fibronectin-coated sulphated Intrasite was stained with the green nuclear dye pico green, (10 μl; 30 minutes; 4° C.; Dark; Molecular Probes). The chondrocyte-seeded, FCS-coated sulphated Intrasite was stained with the red nuclear dye, EtBrHD, (5 μl; 30 min; 4° C.; Molecular Probes). The samples were washed three times with PBS, (2500 rpm; 5 min), the supernatant removed and the samples placed in a 60° C. water bath.

Agarose, (4% w/v in PBS; Sigma) was melted by microwaving, aliquoted (5 ml) to the base of Falcon tubes and allowed to set at 4° C. A 'basket' was fitted into an 'asymmetric collar', placed upon the agar plug, orientated as shown in FIG. 2.14 and the apparatus placed in a 60° C. water bath. Melted agarose, (20 ml; 1.5%; 60° C.), was added to the tube containing the asymmetric collar and the pico green stained bone marrow stromal cell/biomaterial aggregates pipetted onto the gel. The tube was then capped, orientated within the centrifuge rotor and centrifuged, (2500 rpm; 5 min) to sediment the stromal cell-seeded material into the 'basket'. The EtBrHD stained chondrocyte/biomaterial aggregates were then pipetted onto the agarose and the tube re-centrifuged (2500 rpm; 5 min). The contents of the tube were then allowed to set at 4° C. for 16 hours. The plug of agarose and sedimented, dyed, cell-seeded sulphated Intrasite was dissected from the basket, bisected and viewed using a Leica microscope. Images were grabbed using a Spot camera.

Results

FIG. 2.16 shows that the method and apparatus produced a clearly defined, well consolidated, bilayered construct consisting of (i) a layer of pico green stained bone marrow stromal cell seeded, fibronectin coated sulphated Intrasite and (ii) a layer of EtBrHD stained chondrocyte seeded coated sulphated Intrasite.

Production of a Viable Bilayered Construct

Samples of the two cell-seeded biomaterials, (i.e. (i) bone marrow stromal cell seeded, fibronectin coated sulphated Intrasite and (ii) chondrocyte seeded, FCS coated sulphated Intrasite), were centrifuged, (2500 rpm; 5 min), and the supernatant removed to leave the seeded biomaterial in approximately 1 ml of medium.

Agarose, (4% w/v in DMEM; Sigma) was melted by microwaving, aliquoted (5 ml) to the base of Falcon tubes and allowed to set at 4° C. A 'basket' was fitted into an 'asymmetric collar', sterilised by immersion in 60% acetone in PBS, placed upon the agar plug and orientated as shown FIG. 2.14. DMEM/10% FCS, (20 ml) was added to the tube and the bone marrow stromal cell-seeded, fibronectin-coated sulphated Intrasite carefully pipetted into the tube. The apparatus was then orientated within the centrifuge rotor and centrifuged, (2500 rpm; 5 min) to sediment the first layer of material. Chondrocyte-seeded, FCS-coated sulphated Intrasite was then carefully pipetted into the tube without disturbing the existing layer and the tube re-centrifuged, (2500 rpm; 5 min). The 'collar and basket' were then extracted from the Falcon tube, the 'basket' containing the sedimented cells removed from the 'collar' and the cell/material aggregate carefully transferred to the well of a 6 well plate containing 5 ml of DMEM/10% FCS and the culture incubated at 37° C. in a humidified atmosphere of 5% $CO_2$.

Ex Vivo Evaluation of Example 2.2

Method

Pairs of full-thickness articular cartilage strips, (5 mm×~40 mm), were dissected from the metacarpophalangeal joints of neonatal calf hooves and transected with a scalpel to give two groups of 3 explants, (each 5 mm×10 mm). A cylindrical, full-thickness defect was cut in two of the cartilage explants from each group using a biopsy punch, (3.5 mm diameter; Stiefel), and the injured toroidal explants and the uninjured explant transferred to the wells of a 6 well plate containing DMEM/10% FCS (8 ml).

Samples of (i) bone marrow stromal cell seeded, fibronectin coated sulphated Intrasite and (ii) chondrocyte-seeded, FCS coated sulphated Intrasite were centrifuged, (2500 rpm; 5 min), and the supernatant removed to leave the seeded biomaterial in approximately 1 ml of medium.

Agarose, (4% w/v in DMEM; Sigma) was melted by microwaving, aliquoted (5 ml) to the base of Falcon tubes and allowed to set at 4° C. A 3 mm diameter polycaprolactone re-enforced, 3D knitted scaffold, (Culzean), was fitted into an 'asymmetric collar', sterilised by immersion in 60% acetone in PBS, placed upon the agar plug and orientated as shown in FIG. 2.14. DMEM/10% FCS, (20 ml) was added to the tube and the bone marrow stromal cell-seeded, fibronectin-coated sulphated Intrasite carefully pipetted into the tube. The apparatus was then orientated within the centrifuge rotor and centrifuged, (2500 rpm; 5 min) to sediment the first layer of material into the superficial zone of the scaffold. Chondrocyte-seeded, FCS-coated sulphated Intrasite was then carefully pipetted into the tube without disturbing the stromal cell layer and the tube re-centrifuged, (2500 rpm; 5 min). The 'collar and scaffold' were then extracted from the Falcon tube, the cell-seeded scaffold removed from the 'collar', inverted and inserted into the 3 mm diameter defect in a cartilage explant.

Groups of three explants from a single cartilage strip, (i.e. one unwounded, one with an empty defect and one with a defect containing a bilayered cell-seeded construct), were transferred to three wells of a 6 well plate containing 8 ml of DMEM/10% FCS supplemented with ascorbate 2 phosphate (25 µg/ml) and the cultures incubated at 37° C. in a humidified atmosphere of 5% $CO_2$ for 0-14 days.

At the end of the incubation period, samples were analysed using (i) live/dead stain, (Molecular Probes), to determine the distribution of viable and non viable cells within the specimens, (ii) histology to visualise the general morphology, cellularity and matrix composition of the sample and (iii) immunocytochemistry to determine which cells were expressing type II collagen (i.e. phenotypically normal chondrocytes) or type I collagen, (fibroblasts, progenitor cells and de-differentiated chondrocytes).

For viability measurements the samples were bisected, stained with a combination of calcein AM, (0.6 µl/ml; 90 min; Molecular Probes) plus EtBrHD, (10 µl; 90 min), the samples washed in PBS, (3×15 min), placed upon their cut surfaces and optic sections 100 µm into the specimen viewed by confocal microscopy.

For histology, the medium was removed and the samples fixed in 10% formal buffered saline, (0.5 ml; 24 hours), processed on the VIP processor, wax embedded, sectioned on a Leica microtome (51 µm). For histological analysis, specimens were dewaxed, rehydrated and stained with either Safranin O, (0.1%, 6 min), Picrosirius Red (0.1% in saturated alcoholic picric acid, 90 min), Toludine Blue, (0.5%; 15 sec), or Haematoxylin and Eosin (Gills haematoxylin, 6 min and alcoholic eosin, 4 min). Specimens were mounted using Histomount and images captured using the Leica microscope and SPOT camera and related software.

For immunocytochemical analysis, the slides were dewaxed, rehydrated and subjected to Dako HMAR (heat mediated antigen retrieval system; Dako). For collagen type I detection, the slides were blocked in swine serum (2.5%, 20 min at room temperature; Dako), washed thoroughly in PBS and immersed in either rabbit polyclonal anti-collagen I antibody (10 µg/ml; Biogenesis) or an equivalent concentration of non-immune rabbit IgG immunoglobulin (Dako), overnight at 4° C. The slides were then washed in PBS, immersed in swine anti-rabbit biotinylated secondary antibody (1:100; room temperature for 30 min; Dako), washed in PBS, immersed in Strepavidin Texas Red (1:100, room temperature for 30 min; Amersham Pharmacia Biotech), washed in PBS, mounted using Vectormount for fluorescence and coverslipped.

For collagen type II detection, the slides were blocked in rabbit serum (2.5%, 20 min at room temperature; Dako), washed thoroughly in PBS and immersed in either mouse monoclonal collagen II primary antibody (1 µg/ml; Neomarkers) or an equivalent concentration of non-immune mouse IgG immunoglobulin (Dako) overnight at 4° C. The slides were then washed in PBS, immersed in rabbit anti-mouse biotinylated secondary antibody (1:100; room temperature for 30 min; Dako), washed thoroughly in PBS, immersed in Strepavidin FITC (1:100; room temperature for 30 minutes; Amersham Pharmacia Biotech), washed thoroughly in PBS, mounted using Vectormount for fluorescence and coverslipped.

Results and Discussion.

Explants without defects showed viable cells throughout the tissue except for a scattering of dead cells at the mineralised base of the explant and a limited number of dead cells along the superficial surface. The matrix showed intense metachromatic staining with Safranin O and toluidine blue, (indicative of the presence of a glycosaminoglycan-rich matrix), red staining with picrosirius red, (indicative of the presence of collagen) and a morphologically normal cartilaginous appearance with H+E.

Samples with empty defects showed a clearly defined, broad band of cell death along the margin of the wound. H+E staining showed morphologically necrotic cells with shrunken nuclei in this zone, whilst Safranin O and picrosirius red showed a loss of matrix staining near the wound edge. In a minority of specimens, cells were observed migrating from the mineralised tissue at the base of the defect over the cut surface of the cartilage, after about 6 days in culture. These migrating cells could be similar to those that fill cartilage defects following abrasion arthroplasty, surgical microfracture or drilling of the subchondral bone plate.

Samples containing implants showed collagen II production by the chondrocytes in the mid/deep zones of the implant and the surrounding cartilage, together with limited amounts of collagen I staining within the superficial zone of the device. The matrix in the implant stained for both collagen and glycosaminoglycans with the histological dyes, but to a much lower level than was observed in the surrounding cartilage tissue. Morphological data showed that viable cells were growing upon the wound margin, although it was not possible to categorically state whether these cells had arisen from the base of the explant or the implants in these experiments. It also appeared that the zone of cell death was diminished and the extent of matrix loss reduced. Overall the results were consistent with the hypothesis that the layered, scaffold re-enforced implant produced using these methods could be implanted into a focal, full thickness cartilage wound and used to promote cartilage repair.

Example 2.3

Introduction

The objective of this example is to show how the fast binding rate of superficial zone chondroprogenitors to selected materials can be used to produce a zoned implant. One of the implant's zones being enriched with chondroprogenitors whilst the remainder is depleted. In this example a fibrous scaffold, coated with fibronectin, is seeded with a mixed population of cells (i.e. superficial, middle and deep zone) for a limited time such that a high proportion of the fast binding superficial zone chondroprogenitor cells will attach but the majority of mature chondrocytes will fail to attach during the time allowed. The cells which do not attach in that time (i.e. the more mature cells) will be seeded onto a second felt and allowed to adhere. The two scaffolds are then brought together to form a bilayered culture. The first felt being enriched with superficial zone chondroprogenitors. Identification of the superficial zone chondroprogenitors is by immuno-staining for N1.

Experimental

Coating of Needle-Felts 0.5 mm thickness, 10 mm diameter PET needle-felts with a density of 62 mg/cc (Batch No. ET216/200/4/1) were coated with 10 µg/ml plasma fibronectin in Dulbecco's PBS with 1 mM $MgCl_2$ and 1 mM $CaCl_2$ overnight at 4° C. In addition, 10 mm diameter PET needle-felts (Batch No. PS0324/04), 2 mm thick, with a density of 45 mg/cc were coated overnight at 4° C. with D-MEM containing 10% FCS. 0.5 mm needle-felts were blocked with 1% BSA for 1 hour at 37° C. prior to cell seeding.

Cell Isolation

Mixed populations of superficial, middle and deep zone chondrocytes were isolated from the articular cartilage of 2-3 week old bovine metatarsophalangeal joints. The portions of cartilage were then placed directly into Dulbecco's Modified Eagle Medium (DMEM) containing 5% foetal calf serum (FCS) and 0.1% pronase (Merck, $4\times10^6$ units/g) and incubated at 37° C. for 3 hours. Cartilage was then washed once with PBS and incubated in DMEM containing 5% FCS and 0.04% collagenase (Worthington, 237 U/mg) and incubated overnight at 37° C. with gentle shaking.

Tissue digests were then strained through a 70 µm cell strainer (Falcon) to remove debris. The resultant filtrate was then centrifuged at 1000 rpm for 5 minutes to pellet cells. Cell pellet was then resuspended in serum-free DMEM, centrifuged at 1000 rpm for 5 minutes and resuspended in serum-free DMEM. Cell number was then counted and cells resuspended to the desired concentration.

Cell Seeding 0.5 mm and 2 mm needle felts were coated with plasma fibronectin and FCS respectively and blocked as described above. A mixed population of chondrocytes was isolated and resuspended to a concentration of $4\times10^6$ cells/ml. 0.5 mm f Its were seeded with 1 ml of this suspension for 30 minutes with constant agitation on an orbital shaker at 37° C. After this time, the felt was removed and washed 3× with serum-free media to remove non-adherent cells and the felt was transferred to DMEM containing 10% FCS for 5 hours. Washes were pooled, added to the original seeding cell suspension, pelleted by centrifugation, resuspended in DMEM containing 10% FCS and seeded onto the 2 mm felts as described above, overnight at 37° C. After the seeding periods, both felts were washed twice with PBS, fixed in −20° C. methanol for 10 minutes and transferred to PBS containing 0.02% sodium azide. Felts were stored in this solution at 4° C. until used for immunostaining.

2 mm felts coated overnight with FCS at 4° C. were seeded, without the preceding 0.5 mm felt, with a mixed population of chondrocytes as a control for Example 2.3.

Notch1 Immunostaining

For immunostaining, felts were washed 3×5 mins with PBS and blocked with 2.5% normal rabbit serum for 1 hour at room-temperature. Felts were then washed 3×5 mins with PBS, incubated with 10 µg/ml goat anti-notch1 antibody overnight at 4° C. Felts were then washed 3×5 mins with PBS and incubated with a 1:100 dilution of biotinylated rabbit anti-goat secondary antibody in PBS for 1 hour at room temperature. Felts were washed again for 3×5 mins with PBS and incubated with a 1:100 dilution of Streptavidin-FITC in PBS for 1 hour at room temperature. Felts were then washed 3×5 mins with PBS then viewed using the Leica DM-IRBE inverted confocal microscope using an ArKr laser exciting at 488 nm. Optical sections were taken at 10 µm intervals from the surface of the felt to a depth of 400 µm. Using the Leica TCS-NT software Maximum Projection function the images were stacked displaying the maximum grey scale value along the z-axis. Images were quantified using Image Pro-plus that calculated the area of green fluorescence (N1 stain) on the image. As the size of the image in the x- and y-axis is known (1000 µm×1000 µm), together with the depth of the optical sections (z-axis; 400 µm) is known, then the amount of green fluorescence per $mm^3$ can be calculated.

Results

FIG. 2.17 shows the quantification of green fluorescence in the two felts compared to the control. Immediately apparent is the greater amount of N1+ fluorescence in the upper felt that was coated with fibronectin and seeded with the mixed population of chondrocytes for minutes prior to the seeding of the lower felt with the same cell population.

TABLE 2.3

Area of N1 fluorescence in upper and lower needle felts.

| Upper felt | Lower felt | Control |
| --- | --- | --- |
| 0.8876 ± 0.382248 | 0.018998 ± 0.012973 | 0.035932 ± 0.038209 |

Conclusion

This study has demonstrated the use of a fibronectin coated felt as a chondroprogenitor binding material which would then be layered onto a second felt that contains the more mature chondrocytes. Thus creating a zonally seeded implant.

Example 2.4

Introduction

The objective of this example is to demonstrate how the fast binding rate of superficial zone chondroprogenitors to selected materials can be used to produce a zoned implant. One of the implant's zones being enriched with chondroprogenitors whilst the remainder is depleted. In this example the zones are created within a single scaffold. A selected zone of a fibrous scaffold is coated with fibronectin and then seeded with a mixed population of cells (i.e. superficial, middle and deep zone) for a limited time such that a high proportion of the fast binding superficial zone chondroprogenitor cells will attach to the fibronectin coated zone but the majority of mature chondrocytes will fail to attach during the time allowed. The cells which do not attach in that time (i.e. the more mature cells) are collected and reintroduced to the scaffold along with binding materials and allowed to adhere throughout the scaffold. Identification of the superficial zone chondroprogenitors is by immuno-staining for Notch1.

Experimental

Coating of Needle-Felts

The upper surface of 10 mm diameter PET needle-felts, 2 mm thick, with a density of 45 mg/cc were coated with plasma fibronectin (Sigma) at a concentration of 10 µg/ml in Dulbecco's PBS with 1 mM $MgCl_2$ and 1 mM $CaCl_2$ (Sigma). Felts were coated overnight at 4° C. Controls were coated overnight in Dulbecco's PBS with 1 mM $MgCl_2$ and 1 mM $CaCl_2$ alone. Felts were blocked with 1% BSA for 1 hour at 37° C. prior to cell seeding.

Cell Isolation

Mixed populations of superficial, middle and deep zone chondrocytes were isolated from the articular cartilage of 2-3 week old bovine metatarsophalangeal joints. The portions of cartilage were then placed directly into Dulbecco's Modified Eagle Medium (DMEM) containing 5% foetal calf serum (FCS) and 0.1% pronase (Merck, $4\times10^6$ units/g) and incubated at 37° C. for 3 hours. Cartilage was then washed once with PBS and incubated in DMEM containing 5% FCS and 0.04% collagenase (Worthington, 237 U/mg) and incubated overnight at 37° C. with gentle shaking.

Tissue digests were then strained through a 70 μm cell strainer (Falcon) to remove debris. The resultant filtrate was then centrifuged at 1000 rpm for 5 minutes to pellet cells. Cell pellet was then resuspended in serum-free DMEM, centrifuged at 1000 rpm for 5 minutes and resuspended in serum-free DMEM. Cell number was then counted and cells resuspended to the desired concentration.

Needle felts were coated with 10 μg/ml plasma fibronectin and blocked with 1% BSA for 1 hour at 37° C. A mixed population of chondrocytes was isolated and resuspended to a concentration of $4 \times 10^6$ cells/ml. Felts were seeded with 1 ml of this suspension for 30 minutes with constant agitation on an orbital shaker at 37° C. The cell-seeded felt was then washed 2×10 min with serum-free media to remove non-adherent cells and the washes were pooled, pelleted by centrifugation and resuspended in 1 ml DMEM containing 10% FCS. Seeded felts were then transferred to DMEM containing 10% FCS. Pooled non-adherent cells and seeded felts were incubated at 37° C. overnight.

Pooled cells were then seeded back into the corresponding felt. The felt was then incubated in the cell suspension for approximately 7 hours with constant agitation on an orbital shaker at 37° C. After this time, felts were washed twice with PBS, fixed in −20° C. methanol for 10 minutes and transferred to PBS containing 0.02% sodium azide. Felts were stored in this solution at 4° C. until used for immunostaining.

N1 Immunostaining

For immunostaining, felts were washed 3×5 min with PBS and blocked with 2.5% normal rabbit serum for 1 hour at room temperature. Felts were then washed 3×5 min with PBS, incubated with 10 μg/ml goat anti-notch1 antibody (Santa Cruz) overnight at 4° C. Felts were then washed 3×5 min with PBS and incubated with a 1:100 dilution of biotinylated rabbit anti-goat secondary antibody in PBS for 1 hour at room temperature. Felts were washed again for 3×5 min with PBS and incubated with a 1:100 dilution of Streptavidin-FITC in PBS for 1 hour at room temperature. Felts were then washed 3×5 min with PBS then viewed using the Leica DM-IRBE inverted confocal microscope using an ArKr laser exciting at 488 nm. Optical sections were taken at 10 μm intervals from the surface of the felt to a depth of 400 μm. Using the Leica TCS-NT software Maximum Projection function the images were stacked displaying the maximum grey scale value along the z-axis. Images were taken of the surface of coated felts, the underside of coated felts (i.e. non-coated region) and the upper and lower surfaces of non-coated felts.

Images were quantified using Image Pro-plus that calculated the area of green fluorescence (N1 stain) on the image. As the size of the image in the x- and y-axis is known (1000 μm×1000 μm), together with the depth of the optical sections (z-axis; 400 μm) is known, then the amount of green fluorescence per mm$^3$ can be calculated.

Results

TABLE 2.4

Area of NI fluorescence in upper and lower surfaces of coated and uncoated felts.

| Upper surface of coated felt | Lower surface of coated felt | Upper surface of non-coated felt | Lower surface of non-coated felt |
|---|---|---|---|
| 10380 ± 1557 | 1456 ± 517 | 1716 ± 1155 | 1744 ± 513 |

FIG. 2.18 shows the quantification of green fluorescence in the various zones. Immediately apparent is the greater amount of N1+ fluorescence in the upper surface of the felts which had had the upper surface coated with fibronectin.

Conclusion

This study has demonstrated the use of fibronectin as a chondroprogenitor binding material to produce zonally seeded biomaterials i.e. a biomaterial with chondroprogenitors on the upper surface and more mature cells in the lower regions.

Ex Vivo Evaluation of Example 2.4

Introduction

Example 2.4 uses the fast binding rate of superficial zone chondroprogenitors to selected materials to produce a zoned implant. One of the implant's zones being enriched with chondroprogenitors whilst the remainder is depleted. A selected zone of a fibrous scaffold is coated with fibronectin and then seeded with a mixed population of cells (i.e. superficial, middle and deep zone) for a limited time such that a high proportion of the fast binding superficial zone chondroprogenitor cells attach to the fibronectin coated zone whereas the majority of mature chondrocytes will fail to attach during the time allowed. The cells which do not attach in that time (i.e. the more mature cells) are collected and reintroduced to the scaffold along with binding materials and allowed to adhere throughout the scaffold.

Method.

The upper surface of PET needle-felts, (3.5 mm diameter×3 mm thick; 45 mg/cc), were coated with either plasma fibronectin (10 μg/ml in Dulbecco's PBS; Sigma) or PBS, for 16 hours at 4° C. and the felts were blocked for 1 hour at 37° C. with 1% BSA.

Explants of full thickness articular cartilage from 2-3 week old bovine metatarsophalangeal joints were placed directly into Dulbecco's Modified Eagle Medium (DMEM) containing 5% foetal calf serum (FCS) and 0.1% pronase (Merck, $4 \times 10^6$ units/g) and incubated at 37° C. for 3 hours. Cartilage was then washed once with PBS and incubated in DMEM containing 5% FCS and 0.04% collagenase (Worthington, 237 U/mg) and incubated overnight at 37° C. with gentle shaking. The tissue digests were strained through a 70 μm cell strainer (Falcon) to remove tissue debris and the resultant filtrate centrifuged, (1000 rpm; 5 min) to pellet the cells. The cell pellet was resuspended in serum-free DMEM, centrifuged, (1000 rpm; 5 min) and resuspended in serum-free DMEM.

A mixed chondrocyte suspension, (750,000 cells/ml; 1 ml), was seeded onto the felts for 30 minutes with constant agitation on an orbital shaker at 37° C. The cell-seeded felts were then washed with serum-free media (2×10 min) to remove non-adherent cells and the washes pooled, pelleted by centrifugation, (1000 rpm; 5 min), and resuspended in DMEM/10% FCS (1 ml). Seeded felts were then incubated in DMEM containing 10% FCS for 16 hours at 37° C. The pooled non adherent cells were then seeded back onto the felts and the cultures incubated for 16 hours with constant agitation on an orbital shaker at 37° C. The seeded felts were then be transferred to fresh D-MEM containing 10% FCS and cultured for 7 days.

Strips of cartilage (approx 30 mm×5 mm) were obtained from 2-3 week old bovine metatarsophalangeal joints, cut into pieces (~5 mm×5 mm square) and defects created by cutting full thickness holes, 3.5 mm in diameter from the centre of the cartilage explants using a 3.5 mm diameter Acufex cylindrical chisel. Five experimental groups were produced by filling the defects with:

[1] Zonally cell-seeded constructs.
[2] Control cell-seeded constructs (i.e. non-fibronectin coated).
[3] Non cell-seeded construct.
[4] Replacement of the disc that was originally cut out.
[5] Defect left unfilled Experimental groups were then be cultured for 7 days after which they were incubated with ethidium homodimer, (90 min), and either (i) fixed with 10% NBFS, wax embedded, sectioned and stained with conventional histological stains e.g. H & E and Safranin O or (ii) dewaxed and examined under fluorescence optics to assess cell death.

Results

Unfilled defects showed a band of dead cells and reduced matrix quality at the wound margins. The amount of cell death was reduced in samples where the plug of cartilage was replaced into the defect site, especially in regions of close apposition between the two cut cartilage surfaces. Unseeded constructs remained empty for the 7 day incubation period, except for a small number of migrating cells which may have arisen from the base of the cartilage explant. Most of the migrating cells remained attached to the cut cartilage surface. Control and zonally seeded constructs showed viable cells throughout the implant and increased numbers of cells upon the cartilage wound margin. These results suggest that the zonally seeded constructs could be used as implants to promote cartilage repair Example 3.1

Example of the First and Second Aspects of the Invention

Implant Manufacture

An implant according to the invention comprises a scaffold made according to the following procedure: a three-dimensional, knitted PET fabric (2 mm thick, with a cruciform spacer fabric architecture and a macroporous bone-facing surface comprising pores of 1-2 mm diameter, made by Culzean Fabrics) was heat set at 121° C. for 15 mins and reinforced with polycaprolactone (PCL) by drawing the fabric through a pool of molten PCL using a pair of motor-driven 'nip rollers'. Pairs of adjacent spacer fabric fibres within the three-dimensional knitted fabric cross to form broad based 'X's that are readily bridged by the PCL, thereby maximising the strength of the re-inforced fabric. Likewise, the close packed fibres of the upper and lower surfaces of the 3D knit are frequently bridged by PCL to form strong, thermosettable surfaces that are sufficiently robust to hold a suture.

The material was allowed to re-expand and cool to produce a scaffold layer with a compressive modulus of 1.8 MPa and a void fraction of greater than 75%.

Onto one surface of the three-dimensional, reinforced 3D-knitted fabric is bonded a conformable, non-woven PGA needle felt of thickness 1 mm, with a very low compressive modulus (~0.02 MPa) and a void fraction of greater than 90%. Bonding was achieved using heat and a polymer solution. The second (upper, articular) surface of the re-enforced, knitted fabric is coated with a chondroprogenitor cell-binding material, fibronectin in this case, to a depth of 20% of the thickness of the three-dimensional knitted fabric (13.3% of the thickness of the combined implant). The lower region of the knitted fabric and the non-woven PGA felt is uncoated with the chondroprogenitor cell-binding material.

Implant Preparation/Cell-Seeding

The scaffold may be heated gently to soften the polycaprolactone, (40-60° C.), and moulded to the contour of the implant site. The resulting scaffold is sufficiently robust to withstand functional loading whilst retaining a sufficiently porous structure to allow cell-migration within the defect site.

Articular chondrocytes comprising autologous cells extracted from a patient's biopsy/mosaicplasty explant and a source of chondroprogenitor cells, (marrow stromal fibroblasts), are seeded onto 50-250 µm diameter microcarrier beads, and allowed to proliferate in vitro. The resulting cell-covered biomaterial particles are introduced by sedimentation into the void spaces of the knitted fabric prior to implantation into the defect site (to give $\geq 1 \times 10^6$ cells/cm$^2$ implant area). The particulate carrier material allows the chondrocytes to be expanded in culture and introduced into the body of the device without the need for a trypsinisation and re-attachment step.

Implantation

The base of the implant site is mechanically debrided to expose and abrade the subchondral bone, whilst the periphery of the defect is cut back to healthy cartilage using sharp instruments. The device is then press-fitted into the defect site and secured in position with sutures and/or bioresorbable pegs. Mesenchymal cells from the abraded subchondral bone migrate into the non-woven felt and contribute to implant fixation in the weeks after implantation.

Example 3.2

Use of Chondroprogenitor Binding Material to Purify Chondroprogenitor Cells

Fibronectin was coated onto 35 mm Petri dishes (10 µg/ml; Sigma). Chondrocytes were prepared by digesting superficial zone cartilage in pronase and collagenase and suspending the released cells in serum-free medium DMEM (4000 superficial cells/ml; Sigma). The isolated cells were added to the fibronectin coated dishes for 40 mins. The coated Petri dishes were then washed with serum free medium DMEM to remove the non-adherent cells, which were transferred to fresh culture dishes. Colony forming efficiency, (the percentage of the cells capable of dividing to form a colony over a 10 day incubation period), was found to be much higher amongst the fibronectin adherent cells than the non-adherent cells ($p=<0.001$). Flow cytometry indicated that the adherent cells expressed high levels of integrin $\beta_1$, a cell surface marker known to participate in cell binding to fibronectin.

Example 3

Identification of Materials Which Selectively Bind Chondroprogenitor Cells or Move Mature Chondrocytes Materials that preferentially bind either chondroprogenitor cells or more mature chondrocytes were identified by, (i) comparing the adhesion rates of SZC, MZC and DZC to candidate cell-binding materials coated onto tissue culture plastic, (ii) measuring differences in colony forming efficiency amongst superficial zone cells grown upon coated-culture plastic and (iii) demonstrating the ability of 'binding-material'-coated, particulate biomaterials, (e.g. fibronectin-coated, sulphated Intrasite) to bind colony forming SZC and colony forming bone marrow stromal cells.

Methods
Cell Isolation

Chondrocytes from the surface, mid and deep zones of neonatal bovine articular cartilage were isolated from the metacarpophalangeal joint by careful dissection followed by sequential pronase/collagenase digestion (3.17 IU ml$^{-1}$ pronase 3 h at 37° C.; 0.12 IU ml$^{-1}$ collagenase type I 16 h at 37° C. in DMEM/F12 containing 5% FCS, 50 µg ml$^{-1}$ Gentamycin, 100 µg ml$^{-1}$ ascorbate). Cells were centrifuged, resuspended in DMEM/F12, counted using a haemocytometer and resuspended in serum free media.

Serum-free MG-63 conditioned medium (40 ml; collected from 80% confluent cells over 48 hours), was circulated through an anti-FN-EDA, (Oxford Biotech.), antibody-coated immuno-affinity column at a flow rate of 10 mlh$^{-1}$ for 16 hours at 4° C. The A280 nm of the eluant was measured every 10 minutes using a Perkin-Elmer Lambda 2 spectrophotometer until the absorbance reached zero. FN-EDA was then eluted from the column with elution buffer (20 mM CAPS, 150 mM NaCl, 10 mM EDTA, pH11), and fractions collected every 10 minutes until the absorbance returned to zero.

FN-EDA containing fractions were pooled and dialysed overnight at 4° C. using 10,000 MWCO dialysis membranes (Pierce), against 4 L of dialysis buffer (10 mM CAPS, 150 mM NaCl, 1 mM $CaCl_2$, pH11). FN-EDA was removed from the dialysis membranes and protein concentration determined by Micro-BCA assay. Pooled fractions of eluted FN-EDA, unbound FN-EDA and unfractionated MG-63 media were tested by ELISA. SDS-PAGE was also carried out by running 1 µg of purified FN-EDA alongside 1 µg of plasma and cellular fibronectin on a 4-12% bis-acrylamide gel (NOVEX). Both tests confirmed a high purity of FN-EDA.

Evaluation of Superficial, Mid and Deep Zone Chondrocytes Adhesion to Candidate Cell-Binding Materials Coated onto Tissue Culture Plastic Multiwell plates were coated with candidate materials, (10 µg/ml) or control substances, (10% FCS, positive control; 10% BSA negative control), overnight at 4° C. The plates were blocked with BSA, (1%; 37° C. for 1 hour), and suspensions of superficial, mid or deep zone neonatal bovine chondrocytes (0.5 ml; 1000 cells per ml) added.

The cultures were incubated for 20 minutes, 150 minutes, 1 day or 4 days at 37° C. in a humidified atmosphere of 5% $CO_2$, washed with PBS and then incubated in DMEM/10% FCS for 1.5 hours to stabilise cell adhesion. The plates were then washed in PBS, fixed with methanol, (−20° C.; 30 min), rinsed with distilled water and air-dried. (The fixed plates maybe stored at 4° C. for a month prior to testing).

For analysis, the cells were washed with PBS, stained with Ethidium Homodimer, (1 in 1000 dilution; 37° C.; Molecular Probes) and counting using a fluorescent microscope. Results were expressed as the percentage of bound cells and ranked to identify materials that preferentially bound particular cell populations.

Chondroprogenitor Adhesion Assays: Differential Adhesion and Colony Forming Efficiency The wells of 24 well plates were coated with extracellular matrix components, (fibronectin, acid soluble type I collagen, acid soluble type II collagen, acid soluble type IV collagen, laminin or tenascin; 27 nM in PBS containing 1 mM $CaCl_2$ and 1 mM $MgCl_2$; 'PBS+'), for 16 hours at 4° C. The plates were washed in PBS+, seeded with SZC or DZC, (700 cells ml$^{-1}$; DMEM/F12, 1 ml), and incubated for 20 minutes at 37° C. in a humidified atmosphere of 5% $CO_2$.

The total number of adherent cells/well was counted using phase contrast microscopy after 4 hours. The number of colonies (defined as a cluster of 4 or more chondrocytes) per dish were counted using phase contrast microscopy after 4 days and the colony forming efficiency (CFE) was calculated as follows:

$$CFE = \frac{\text{Number of colonies at 4 days}}{\text{Initial number of adherent cells}}$$

The experiments were repeated to compare the activity of plasma fibronectin (Sigma) with cellular fibronectin (Sigma) or affinity purified fibronectin-EDA.

Adhesion of Colony Forming SZC and Colony Forming Bone Marrow Stromal Cells to Adhesion Factor-Coated, Sulphated Intrasite: 'the Colony Depletion Assay'

A minority of BMSC and SZC form colonies of >16 cells when cultured on tissue culture plastic in DMEM/10% FCS for 4 and 6 days respectively. We regard these colony-forming cells as progenitor cells. Sulphated Intrasite was coated with plasma fibronectin, cellular fibronectin, collagen IV, polylysine, laminin (all 60 µg/ml) or PBS in 2.5 ml DMEM for 2 h at 4° C. The coated biomaterial was incubated with bone marrow stromal cells or SZC suspensions (125 k cells/ml in serum free medium) for 3 h at 37° C., the suspension diluted 1000 fold and aliquoted, (4 ml) to the wells of 12 well plates. Foetal calf serum (0.4 ml) was then added to each of the wells and the cultures incubated for a further 16-24 hours. The wells were then washed with PBS, and the cultures incubated for a further 4-6 days in DMEM/10% FCS (2 ml). Colonies, (discrete clusters of >16 cells), were visualised by phase contrast microscopy and counted blind. Results were expressed as a 'colony depletion score', defined as the number of colonies formed by cell suspensions exposed to adhesion factor pre-treated sulphated Intrasite divided by the number of colonies per well formed by cells exposed to PBS pretreated sulphated Intrasite. A colony depletion score of <=0.5 was defined as the preferential value for colony forming cell-binding, whilst a value of <=0.8 was defined as a threshold value for acceptable colony forming cell binding.

Results

Evaluation of Superficial, Mid and Deep Zone Chondrocytes Adhesion to Candidate Cell-Binding Materials Coated onto Tissue Culture Plastic Data showed that superficial zone cells bound to fibronectin-coated culture plastic to a greater extent than mid or deep zone cells during the initial 20 minute incubation period, (table 3.1). Collagen VI and peanut agglutinin also preferentially bound superficial zone cells at this early time point, but the magnitude of cell-adhesion was minimal (table 3.1).

In contrast, collagen type I, collagen type II, collagen type VI and vitronectin bound mid and deep zone cells to a higher extent than superficial zone cells after a 150 minute incubation, (table 3.2).

Chondroprogenitor Adhesion Assays: Differential Adhesion and Colony Forming Efficiency The colony forming efficiency of SZC that adhered to fibronectin within 20 minutes was significantly higher ($p<0.05$) than that observed in any of the other treatment groups (FIG. 3.6). There were no other statistically significant differences ($p>0.05$ in all cases).

No significant differences were observed between the efficacy of plasma fibronectin, cellular fibronectin and fibronectin-EDA on either (i) the initial adhesion of SZC or MZC, (ii) the colony forming efficiency of the cells nor (iii) the size of colonies formed.

Adhesion of Colony Forming Superficial Zone Cells and Colony Forming Bone Marrow Stromal Cells to Adhesion Factor-Coated, Sulphated Intrasite: 'The Colony Depletion Assay"

In these experiments, cells that do not attach to the coated sulphated Intrasite particles attach to the culture plastic and may subsequently form colonies. Cells that do bind to the sulphated Intrasite particles are removed during the washing step. Colony forming cell adhesion to coated sulphated Intrasite is therefore reflected by a decrease in the number of colonies formed on the culture plastic. Microscopic examination of the diluted suspensions of cells and particles after the initial 3 hour incubation revealed a sparse distribution of particles, (some with adherent cells), together with unattached cells. Addition of foetal calf serum to these cultures for 16-24 hours allowed the cells that had not attached to the biomaterial particles to adhere to the tissue culture plastic. The subsequent washing step removed the particles and any cells that had adhered to them, leaving only those cells that had adhered to the culture plastic. Results showed that there were 46.8±3.76 colonies per well when superficial zone chondrocytes were incubated with PBS pre-treated sulphated Intrasite compared to 21.0±1.39 colonies per well when the superficial zone cells were exposed to plasma fibronectin-coated sulphated Intrasite, (i.e. a colony depletion score of 0.45; p<0.001; see FIG. 3.7). Likewise bone marrow stromal cells incubated with adhesion factor coated sulphated Intrasite gave colony depletion scores of plasma fibronectin, 0.49; collagen IV, 0.67; cellular fibronectin, 0.8; polylysine, 0.88 and laminin 1.26, (see FIG. 3.8).

Discussion

Our previous results showed that a population of N1 positive, fibronectin-EDA secreting, strongly integrin $\beta_1$ positive, colony forming chondroprogenitor cells exist within the superficial zone of neonatal articular cartilage. It was hypothesised that (i) the specific features of these progenitor cells could be used to develop biomaterials that would selectively bind either chondroprogenitor cells or more mature chondrocytes and (ii) that such biomaterials could be seeded with cells and agglomerated to form a zonal implant in which chondroprogenitor cells form a layer near the articular surface whilst more mature chondrocytes are bound in the deeper zones of the implant.

These results show that (i) SZC bind rapidly to fibronectin covered surfaces, (ii) the 'rapid fibronectin-binding' SZC have a high colony forming efficiency when grown on fibronectin-coated surfaces and that (iii) the particulate biomaterial, 'fibronectin-coated sulphated Intrasite' will bind colony forming cells from both superficial zone cartilage and bone marrow stroma. This suggests that fibronectin-coated sulphated Intrasite is a suitable material for use in the superficial zone of the proposed layered, tissue engineered cartilage implant. Different forms of fibronectin, (e.g. plasma fibronectin, cellular fibronectin and fibronectin-EDA), give broadly similar results in these assay systems, suggesting that they could all be used for this purpose.

Our results also show that collagen IV does not selectively bind SZC nor support the adhesion and proliferation of colony forming superficial zone cells. Collagen IV does however adsorb onto particulate, polyanionic biomaterials to give a material with a surface that will bind colony forming cells from bone marrow stroma. Since the colony forming cells in bone marrow stroma are early mesenchymal cells that can form bone, cartilage, fat and fibrous tissues, it is possible that collagen IV binds a more primitive population of mesenchymal precursors than the colony forming cells which commonly occur in the superficial zone of neonatal articular cartilage.

In contrast, collagen type I, collagen type II, collagen type VI and vitronectin all bound mid and deep zone cells to a higher extent than superficial zone cells after a 150 minute incubation. These extracellular matrix components may therefore be utilised to bind more mature chondrocytes to particulate biomaterials. Such cell-seeded materials could be used to form the mid and/or deep zones of a layered, tissue engineered cartilage implant.

TABLE 3.1

Percentage of SZC, MZC and DZC adhering to fibronectin, collagen VI and peanut agglutinin-coated tissue culture plastic after a 20 minute incubation.

| Binding material | SZC | MZC | DZC |
|---|---|---|---|
| Fibronectin | 23.2 | 13.8 | 13.6 |
| Collagen IV | 4.8 | 2 | 2 |
| Peanut agglutinin | 3.6 | 2 | 2 |

TABLE 3.2

Percentage of SZC, MZC and DZC adhering to collagen type I, collagen type II, collagen type VI and vitronectin-coated tissue culture plastic after a 150 minute incubation.

| Binding material | SZC | MZC | DZC |
|---|---|---|---|
| Collagen type I | 13.2 | 21 | 20.4 |
| Collagen type II | 8.8 | 17.2 | 23 |
| Collagen type VI | 7.8 | 17.8 | 22 |
| Vitronectin | 11.2 | 19.2 | 21.4 |

Cell Separation Methods

Homogeneous populations of cells, for instance chondroprogenitor cells e.g. superficial zone chondroprogenitor cells may be separated by other methods. Homogeneous populations of cells may be enriched or isolated from heterogeneous cell mixtures using a range of techniques based upon, (i) the cells' buoyant density or sedimentation rate, (Ficol gradients or counter current elutriation); (ii) antibody binding to specific cell-surface epitopes, (via fluorescent cell sorting, attachment to magnetic beads or complement mediated cell lysis); (iii) differential adhesion to particular substrates; (iv) selective culture media or culture conditions which favour the growth of one cell type rather than another, (v) other physical properties of the cells, e.g. their size, granularity or electrical capacitance.

These techniques may also be used to produce an implant according to the present invention.

Sulphated Intrasite

In a separate aspect of the present invention the invention relates to a synthetic implant for the replacement of damaged cartilage and more particularly for the replacement of load-bearing cartilaginous tissue, such as the meniscus and articular cartilage. The invention also relates to a method of seeding a scaffold means with cells; to a bioreactor suitable for use in that method; to a method of seeding scaffold means specifically using the bioreactor and to a hybrid implant comprising a scaffold means and cell-coated particulates dispersed within it. Finally, the invention also relates to a method of treatment comprising the step of surgically implanting a synthetic implant or a hybrid implant according to the invention.

Popular current procedures for the treatment of articular cartilage defects include high tibial osteotomy (primarily performed in Europe) and muscle release to alter joint biomechanics and loading; lavage and debridement to remove osteophytes and fibrillated areas of cartilage and perforation and penetration of the subchondral bone to induce bleeding and clot formation. It has been established, however, that none of these techniques leads to successful regeneration of the tissue that duplicate the structure, composition, mechanical properties or durability of articular cartilage.

The most common technique is that of subchondral drilling which results in the creation of a fibrin clot and a fibrous tissue. In about 75% of patients there is a satisfactory initial result, but two years after the operation, only 12% of patients remain free of symptoms. Limitations of this approach are the difficulty in predicting the quality and duration of the clinical outcome and, in the long term, this procedure often leaves the patient in a worse condition. On the other hand, subchondral drilling and debridement are generally successful in alleviating symptoms and in postponing the requirement for total knee replacement by between one and three years.

A synthetic cartilage repair product which could predictably alleviate pain, restore function, achieve good fixation and which has a durability enabling it to last longer, for example at least ten to fifteen years or more is seen as an important objective by many surgeons.

One currently available product which attempts to meet the above objectives consists of carbon fibre rods: the cartilage lesions or other defects are cleaned and excised down to the subchondral bone and the carbon fibre rods are inserted into holes made therein. Repair begins with the deposition of collagen in islands around the top of the rods. These islands of growth soon enlarge to completely fill the defects, the rods providing anchorage for the repair tissue in the defect. A significant problem associated with this product is carbon fibre wear debris found in the synovial cavity, which may give rise to problems of abrasion.

Another approach, which has been considered, is to use an implant constructed of a knitted fabric, which provides structural stability, and containing a swellable hydrogel for supporting cells seeded within it. This implant is placed in a cartilage lesion and to promote cartilage growth by means of the increased pressure derived from the swelling hydrogel. A problem associated with the use of implants of this type has been poor integration between the implant and the tissue beneath it, particularly the subchondral bone.

Tissue-engineered approaches to producing devices for cartilage repair employ combinations of cells and biomaterials, which biomaterials may be in the form of synthetic repair products, as described above. The device produced may comprise autologous cells or tissue (derived from the patient's own cells), or allogenic cells or tissue (using cells derived from donated tissues). The autologous approach minimises the risk of disease transmission that accompanies the use of donated tissue, but has the disadvantage that two operations are needed—one to harvest the tissue used in the device, the other to surgically introduce the device once it has been produced. Tissue-engineered approaches using allogenic cells avoid the problems associated with the use of autogenic cells and aim to produce an off-the-shelf cartilage implant which could be used to repair cartilage defects with a single operative procedure. This approach is not without problems either—difficulties encountered include regulatory and ethical ones associated with obtaining donor tissues as well as screening the donor material to prevent the transmission of pathogenic bacteria, viruses or prions.

In addition to the problems specific to the use of allogenic or autogenic cells, the step of culturing cells to engineer a mechanically competent matrix creates problems with nutrient diffusion into the centre of the construct. At first, cell replication increases cell numbers evenly throughout the construct. As the cell numbers increase and extracellular matrix deposition commences, the cells at the periphery of the construct consume a greater proportion of the nutrients diffusing into the device, thereby starving the cells in the centre of the construct and preventing their growth. Eventually the cells in the centre of the construct die, resulting in a construct with a thin viable surface but a necrotic, liquefied core. A method of manufacturing a device for cartilage repair, which avoids this effect, would be a significant improvement over existing techniques.

Current synthetic cartilage repair products and tissue-engineered devices for use in cartilage repair are also unable to meet the conflicting requirements of mechanical resilience and lateral integration. If a cell-seeded implant or a synthetic implant into which cells have migrated has a sufficiently robust structure that it can withstand mechanical loading, then, traditionally, its cells have become trapped within the matrix, unable to migrate into the surrounding tissue and therefore unable to contribute to lateral integration. Conversely, if the implant is sufficiently permeable to permit cell migration and lateral integration, it has traditionally been too weak to withstand mechanical loading. It would therefore be desirable to provide implants that are mechanically robust but which also permit cell mobility within the implant.

It is an object of the present invention to provide a synthetic cartilage repair product which avoids the problems associated with prior art products of this type. In particular it is an object to provide a synthetic cartilage repair product which exhibits improved integration with the tissue with which it is in contact, particularly the subchondral bone.

It is another object of the present invention to provide a synthetic cartilage repair product which is mechanically robust but which also permits cells to move within the implant.

It is another aspect still of the present invention to provide a method for culturing a tissue-engineered cartilage implant, which avoids the problem of inadequate nutrient diffusion to cells at the interior of the implant.

Further objects of the present invention will become apparent from a reading of the following description.

In one aspect, the invention comprises a synthetic implant for repair of a cartilage defect, the implant having a first surface suitable for location at or near a bone-cartilage interface and a second surface suitable for location contiguous with or near to an exposed articular surface, wherein the implant comprises:
  (a) a biocompatible scaffold and, linked thereto or comprised therewithin,
  (b) a conformable zone extending from the first surface towards the second surface.

Reference herein to a material being 'biocompatible' means that there is essentially no clinically significant acute or chronic adverse response when the material is surgically introduced into a mammalian organism over and above that which would occur as a result of sham surgery alone.

The term 'scaffold' should be taken to include a three dimensional, at least partially porous structure, the porosity intended to allow cell infiltration, the exposed parts of the implant (both internal and external) allowing cell adhesion and growth such that cell proliferation and extracellular matrix (ECM) generation can occur and tissue can be laid down.

Reference herein to the term 'conformable zone' is to a zone which deforms on implantation to fill the gaps between it and any material with which it is in contact (tissue such as subchondral bone or cartilage) and should be taken to include a zone having a compressive modulus of less than 1.0 MPa.

An advantage of the conformable zone is that it may be have a much lower compressive modulus than the tissue it is intended to be placed in contact with on implantation and thus may avoid problems of abrasion of the tissue surrounding the implant site. The conformable zone deforms on implantation to fill the gaps between the first surface of the synthetic implant and the tissue with which it is in contact (subchondral bone or cartilage, in general). This allows bone forming cells to migrate into the underside of the synthetic implant and deposit new bone, thereby binding the synthetic implant into the defect site.

In a preferred form of the one aspect of the invention, the compressive modulus of the synthetic implant increases in a direction moving from the first to the second surface. The increase according to the invention may be continual or there may be one or more discrete increases and, in the former case, the gradient of the increase may be constant, or it may itself increase or decrease.

For the reasons given above, the compressive modulus of the conformable zone may be less than 1.0 MPa. Preferably the conformable zone has a compressive modulus of 0.5 MPa or less. More preferably, the compressive modulus of the conformable zone is 0.1 MPa or less. Most preferably, the compressive modulus of the conformable zone is 0.05 MPa or less. If the compressive modulus within the zone is non-constant, then the compressive modulus of the entire zone must nevertheless fulfil the respective criterion.

In another preferred form of the one aspect of the invention, the synthetic implant comprises an articular zone extending from the second surface towards the first surface, wherein the articular zone has a compressive modulus of 1.0 MPa or more. This rigid articular zone protects cells within it from severe mechanical conditions that may be present at the implant site, such as a joint, while allowing cell migration into the articular zone and extracellular matrix (ECM) deposition. On the other hand, the articular layer will typically have a lower compressive modulus than the surrounding tissue, such as cartilage and bone, which typically has a compressive modulus above 5 MPa. As a result, if a surgeon puts the implant in incorrectly and needs to manipulate it into the correct position in situ, it is the implant that will deform during this operation and not the surrounding tissue, thus minimising problems caused by tissue deformation and abrasion.

Preferably, the articular zone has a compressive modulus of 1.8 MPa or more. More preferably, the articular zone has a compressive modulus of 3.0 MPa or more. If the compressive modulus within the zone is non-constant, then the compressive modulus of the entire zone must nevertheless fulfil the respective criterion.

As stated, the synthetic implant comprises a scaffold, as defined above. The scaffold according to the invention may be separate and distinct from the conformable zone and/or the articular zone. Alternatively, if one or both of the conformable zone and the articular zone comprises a three dimensional, at least partially porous structure, as defined above in relation to the term 'scaffold', then the scaffold itself may incorporate the conformable zone and/or the articular zone.

The scaffold according to the invention may, for example, comprise a three dimensional woven or knitted fabric (i.e. a spacer fabric), a fleece (i.e. non-woven) material, a sponge, a foam, particulates or any combination of these materials.

The term 'particulate' should be taken to include materials in the size range 10-2000 µm and preferably in the range 100-600 µm capable of supporting cell adhesion. Particulates according to the invention may comprise cross-linked proteins, polysaccharides, derivatised polysaccharides and synthetic biocompatible polymers, such as those listed below for manufacture of the scaffold. Commercially available particulates may be obtained from Pharmacia (CYTOPORE™, and CYTODEX™) and Sigma (CYTODEX™ again).

The scaffold may comprise one or more layers. If the scaffold comprises a plurality of layers, these layers may all comprise an identical material. Alternatively, each layer may comprise material which is different from some or all of the other layers.

In the event that the scaffold according to the invention comprises at least one layer of three-dimensional woven or knitted fabric, it is preferred to heat set the layer(s). This step causes the molecules in the fibres to re-align to the orientation imposed upon the fibres and causes the fabric to shrink somewhat. Both effects serve to render the fabric more stable. Heat setting is carried out a temperature and for a time known to the skilled man in this field and depends upon the material in question.

The scaffold layer or layers may comprise bioresorbable or non-bioresorbable materials.

Reference herein to a material being bioresorbable means that it breaks down over time due to chemical/biological action and the terms 'resorption' and 'resorb' are to be interpreted accordingly. Preferably, complete resorption occurs within about 5 years, more preferably within about 3 years. An advantage of using bioresorbable materials is that they break down allowing repair tissue completely to fill the defect site such that further surgery to remove them is not necessary.

If a single bioresorbable material is employed, then a preferred selection criterion for it is that it does not significantly resorb during the period of time that tissue is being laid down within it after implantation. Fulfilment of this condition ensures that the implant essentially retains its shape and mechanical integrity until ingrown biological tissue can take over these functions. In numerical terms, it is preferred that there be less than a 5% loss of weight when the bioresorbable material is implanted in vivo for a 12 week period. More preferably, there is less than a 2% loss of weight during the same period. If, on the other hand, the scaffold comprises two or more bioresorbable materials, then it is preferred that at least one of the bioresorbable materials fulfils this criterion in order to provide structural integrity to the implant.

A wide range of bioresorbable materials is known, with differing in vivo resorption times. Not only does the resorption time vary according to the material, but the resorption time of a single material itself can also vary significantly with molecular weight and structural disposition. Finally, it can readily be appreciated that by blending and/or copolymerising different bioresorbable materials and/or by modifying the molecular weights or crystallinity of the components, it is possible precisely to tailor the resorption time of the bioresorbable material to the requirement at hand.

With the above in mind, the bioresorbable materials according to the invention may comprise bioresorbable polymers or copolymers comprising the following monomers or mixtures of polymers and/or copolymers formed thereby: hydroxy acids, particularly lactic acid, glycolic acid; caprolactone; hydroxybutyrate; dioxanone; orthoesters; orthocarbonates; aminocarbonates.

The bioresorbable materials according to the invention may also comprise natural materials such as collagen, cellulose, fibrin, hyaluronic acid, fibronectin, chitosan or mixtures of two or more of these materials. The bioresorbable materials may also comprise devitalised xenograft and/or devitalised allograft.

Bioresorbable ceramics may also be included within the scaffold. Bioresorbable ceramics which may be used according to the invention are mono-, di-, octa-, $\alpha$-tri-, $\beta$-tri and tetra-calcium phosphate, hydroxyapatite, fluoroapatite, calcium sulphate, calcium fluoride, calcium oxide or mixtures of two or more of these materials.

Preferred bioresorbable materials according to the invention comprise poly(lactic acid), poly(glycolic acid), polydioxanone, polycaprolactone, polyhydroxybutyrate and poly(trimethylene carbonate) or mixtures thereof.

It is particularly preferred to use poly(lactic acid). This material has the advantage that it has good mechanical strength and does not resorb too quickly, thus allowing its mechanical properties to be retained for a sufficient time for tissue repair to occur at which point the repaired tissue can take over load-bearing functions: with reference to A. G. A. Coombes and M. C. Meikle, 'Resorbable Synthetic Polymers as Replacements for Bone Graft', Clinical Materials 17, (1994), pp 35-67 samples of poly(lactic acid) have been shown to lose only one or two percent of their weight over a 12 week trial.

Appropriate non-bioresorbable materials according to the invention include polyesters, particularly aromatic polyesters, such as polyalkylene terephthalates, like polyethylene terephthalate (PET) and polybutylene terephthalates; polyamides; polyalkenes such as polyethylene and polypropylene; poly(vinyl fluoride), polytetrafluoroethylene carbon fibres, silk (natural or synthetic), carbon fibre, glass and mixtures of these materials. In addition, non-resorbable ceramics may be employed. Examples of such materials are pure hydroxyapatite, zirconia and alumina. An advantage of non-bioresorbable materials is that they essentially retain their initial mechanical properties—i.e. properties such as strength do not reduce over time. They may therefore provide long-term mechanical support to the repair tissue.

The conformable zone may comprise a fleece (i.e. non-woven) material, a sponge, a foam, particulates, a gel or a combination of these materials and may comprise bioresorbable or non-bioresorbable material. Any of the bioresorbable or non-bioresorbable materials listed in relation to the scaffold may be used, providing that the compressive modulus condition is fulfilled. If the conformable layer comprises a gel, it may be a positively charged, negatively charged or neutral gel, provided that it functions to allow tissue ingrowth. The conformable zone comprises at least one stratum and may comprise a plurality of strata. If the conformable zone comprises a plurality of strata, these may all comprise an identical material. Alternatively, each stratum may comprise material which is different from some or all of the other strata.

The articular zone may comprise a three dimensional woven or knitted fabric (i.e. a spacer fabric), a fleece (i.e. non-woven) material, a sponge, a foam, particulates or a combination of these materials and may comprise bioresorbable or non-bioresorbable material. Any of the bioresorbable or non-bioresorbable materials listed in relation to the scaffold may be used, providing that the compressive modulus condition is fulfilled. The articular zone comprises at least one stratum and may comprise a plurality of strata. If the articular zone comprises a plurality of strata, these may all comprise an identical material. Alternatively, each stratum may comprise material which is different from some or all of the other strata.

The compressive modulus of the articular zone may be an inherent property of the type and structure of the material comprised within it. Alternatively, the articular zone may be reinforced. Reinforcement may be achieved by inclusion of a reinforcing component within the structure to assist in withstanding mechanical loading.

If present, the reinforcing component may comprise a bioresorbable or non-bioresorbable polymer of the types listed above for manufacture of the scaffold. Preferably, the reinforcing component comprises a molten thermosetting polymer or a solution of a thermosetting polymer which is added so as to form strengthening bridges within the articular zone. More preferably still, the polymer is one which thermosets at just above body temperature, that is below 60 C. If the articular zone comprises a fabric material (such as a woven, non-woven or knitted material) the molten reinforcing material connects adjacent strands therewithin, thereby increasing its compressive modulus. Most preferably, the reinforcing component comprises polycaprolactone, because this material has a melting temperature slightly above body temperature, is biocompatible, bioresorbable and renders the implant mouldable.

In the case in which the articular zone comprises a fabric material, one method of providing the above-mentioned reinforcement is to compress the fabric between two 'nip' rollers over which is supplied a pool of molten or dissolved reinforcing polymer. As the fabric is compressed and forced between the rollers a small quantity of reinforcing polymer is carried with it and this is drawn into the fabric when it re-expands on the other side of the rollers, thereby coating the fibres.

In a particularly preferred form of one aspect of the invention, the synthetic implant comprises a scaffold which itself comprises both the conformable zone and the articular zone. Advantageously, the articular zone extends from the second surface towards the first surface to meet the conformable zone, which extends from the first surface towards the second surface. Preferably, the articular zone comprises a three-dimensional, knitted structure comprising poly(lactic acid) [bioresorbable] and/or PET [non-bioresorbable] fibres, which has been reinforced by addition of a molten polycaprolactone reinforcing component. The conformable zone advantageously comprises a felt (non-woven) comprising poly(glycolic acid) and/or PET fibres.

According to a preferred form of one aspect of the invention, the synthetic implant may comprise certain additional components to improve its acceptance by the tissue into which it is to be implanted and its integration into that tissue.

One class of additional component which may advantageously be added to the implant is bioactive materials. Bioactive components which may be incorporated to any part of the implant according to the invention comprises growth factors, for example the Transforming Growth Factor $\beta$ superfamily including TGF$\beta$s, Bone Morphogenetic Proteins BMPs (e.g. BMP2, BMP4), Cartilage Derived Morphogenic Proteins CDMPs (e.g. CDMP-1, CDMP-2) and Growth Differentiation Factors (e.g. GDF5); platelet-derived cell growth factor (PD-ECGF), Platelet Derived Growth Factors (PDGF); Epidermal Growth Factor family, e.g. EGF, Transforming Growth Factor AlphaTGFα; Platelet Derived Growth Factors, e.g. PDGF-A, PDGF-B, PDGF-BB; Fibroblast Growth Factors, e.g. BFGF; Hepatocyte Growth Factors (HGF); Insulin-like Growth Factors, e.g. IGF-1, IGF-II; Growth Hormones (GH); Interleukins (e.g. IL-1, IL-11); Connective Tissue Growth Factors (CTGF); Parathyroid Hormone Related Proteins (PTHrp) and mixtures of at least two of these materials.

In addition to the above, angiogenic factors (angiogenin) and vascular endothelial growth factor (VEGF) can advantageously be added to the conformable zone of the implant.

Synthetic implants according to the invention may be seeded with cells prior to implantation. Alternatively, they may be implanted without cells and cells may be injected at any time after implantation or they may be implanted without any cells so that cell population and attachment occurs by cellular ingrowth only.

Cells with which the implant according to the invention may be seeded are chondrocytes; cells that can differentiate into chondrocytes; such as chondroprogenitor cells and mesenchymal stem cells and cells that can induce other cells to differentiate into chondrocytes. Suitable sources of primitive mesenchymal precursor cells include perichondrium, periosteum, bone marrow and Wharton's Jelly.

If the implant according to the invention is seeded with cells, perforations are preferably provided in the implant extending from the first surface through the conformable layer towards (but not extending to) the second surface of the implant. The perforations may be up to 2.5 mm in diameter, are preferably 0.6 to 2.5 mm in diameter and more preferably 1.6 to 2.2 mm in diameter. The perforations advantageously cover from 5 to 35% of the area of the first surface of the implant and preferably 16-30% of that surface. The presence of such perforations with parameters in the ranges defined facilitates efficient cell seeding.

According to another aspect of the invention, a method of seeding scaffold means with cells is presented, the method comprising the steps of bringing the cells into contact with particulates such that cells adhere to the surface of the particulates, then introducing cell-coated particulates into the scaffold means.

Reference herein to 'scaffold means' is to any device comprising a scaffold, as defined hereinabove. Synthetic implants according to one aspect of the invention are expressly included within the scope of the term 'scaffold means'.

The particulates may inherently be able to bind cells or may be coated with a material capable of binding cells or both. Suitable cell-binding materials with which the particulates may be coated include collagen I, II and IV, fibronectin and fibronectin splice variants, gelatin, laminin, vitronectin, polycationic polymers and polyanionic polymers.

Preferably, the cells are incubated on the particulates in a nutrient solution prior to introduction into the scaffold means to cause them to grow and generate extracellular matrix. More preferably, incubation is carried out for a period of up to 6 weeks. Most preferably, incubation is for a period of between 1 and 3 weeks.

The cell-coated particulates may be introduced into the scaffold means by sedimentation but, in general, a stronger force is required than gravity alone. Advantageously, the cell-coated particulates are forced into the scaffold means by application of a pumping pressure or by centrifugation. Preferably, the cell-coated particulates are introduced into the scaffold means by centrifugation.

An advantage of the present seeding method is that it avoids the problems associated with prior art methods, that is of insufficient nutrient diffusion into the centre of the construct during the phase of in vitro cell growth—see introduction. This is because according to the present method cell growth may take place on the particulates which are distributed in a volume of medium prior to their introduction into the scaffold means. Once in vivo, the implant is provided with nutrients by the blood vessels in the subchondral bone aided by the cyclical compressive stresses on the tissue which draw nutrients in and out of it.

According to another aspect of the invention, a bioreactor is provided which is suitable for use in the method according to the previously mentioned embodiments of the invention. The bioreactor according to one embodiment of the invention comprises an incubation chamber suitable for incubating cell-seeded particulates and a scaffold support chamber suitable for supporting scaffold means, of diameter $d_1$, wherein either (a) the diameter of the incubation chamber, $d_2$, diminishes as it approaches the scaffold support chamber so that it meets the scaffold support chamber at a point where $d_2=d_1$, or (b) the incubation chamber and the scaffold support chamber are connected by funnel means which has diameter, $d_2$, at the end contiguous with the incubation chamber, diminishing to diameter, $d_1$, at the end contiguous with the scaffold support chamber.

The incubation chamber according to one embodiment of the invention may, for example, be spherical, conical or tubular. Advantageously, it is tubular.

The incubation chamber may be larger, the same size as or smaller than the scaffold support chamber, but is preferably smaller than the scaffold support chamber.

In an advantageous alternative of the invention, the funnel means and scaffold support chamber may be integrally comprised within insert means, suitable for insertion into the bioreactor. Advantageously, according to this alternative, the bioreactor comprises a tube.

According to yet another aspect of the invention, a method of seeding scaffold means with cell-seeded particulates using a bioreactor according to one embodiment of the invention is provided. The method according to one embodiment of the invention comprises the following steps:

disposing scaffold means within the scaffold support chamber of the bioreactor;

introducing cell-seeded particulates into the incubation chamber of the bioreactor;

agitating the bioreactor under appropriate conditions, such as temperature, humidity, pH and nutrients, for an appropriate period of time to effect sufficient incubation;

centrifuging the bioreactor to aggregate the cell-seeded particulates within the scaffold means;

removing the scaffold means comprising the cell-seeded particulates from the scaffold support chamber of the bioreactor.

As discussed above, the phrase 'for an appropriate period of time to effect sufficient incubation' means that the cells are incubated in a nutrient solution to cause them to grow and generate extracellular matrix. Preferably, this incubation is carried out for a period of up to 6 weeks. More preferably, the incubation is for a period of between 1 and 3 weeks.

According to another embodiment of the invention, a hybrid implant is presented, comprising scaffold means and cell-coated particulates.

Also according to the invention, a method of treatment of a cartilage defect in a mammalian organism is presented, the method comprising surgically implanting a synthetic implant or a hybrid implant into the defect.

Reference is made to the figures of the application, which are intended to be non-limiting:

Working Example 4.1

Preparation of a Synthetic Implant

To form the articular zone, a three-dimensional, knitted, PET fabric was produced on a double bed raschel warp knitting loom according to the pattern given in Table 4.1:

TABLE 4.1

PET Monofilament spacer with multi filament surfaces. Knitted on a double bed raschel warp knitting machine, 6 guide bars at 24 gauge.

| Bar: | Yarn: | Pattern Chain: | Description: |
|---|---|---|---|
| 1 | 2/44/27 PET | 22/20/44/46 | Lay-in over 4 needles |
| 2 | 2/44/27 PET | 00/02/22/20 | Chain stitch |
| 3 | 0.09 mm Dia PET Monofilament | 10 8/64/20/46 | V-Shape, 3 needles wide |
| 4 | 0.09 mm Dia PET Monofilament | 20/46/10 8/64 | V-Shape, 3 needles wide |
| 5 | 2/44/27 PET | 02/22/20/00 | Chain stitch |
| 6 | 2/44/27 PET | 20/44/46/22 | Lay-in over 4 needles |

The fabric was 3 mm thick with a cruciform spacer fibre architecture. The fabric was washed in purified water at 60° C. followed by a further wash in high purity propan-2-ol then dried and heat set in an autoclave at 121° C. for 15 minutes. It was then reinforced by melt impregnation with polycaprolactone (PCL), CAPA 686 manufactured by Solvay using a pair of internally heated nip rollers. The nip gap and pressure were adjusted to control the uniformity and weight of the coating. A coating weight of 0.80 gram PCL per gram of fabric was attained. The monofilament spacer fibres within the three-dimensional knitted fabric cross one another to form overlapping 'X's'. Where they crossover each other they are bonded by the PCL, thereby increasing the integrity and compressive modulus of the impregnated fabric. Likewise, the multifilament fibres of the upper and lower surfaces of the 3D knit are readily impregnated by the PCL to form strong, thermosettable surfaces that are sufficiently robust to hold a suture. At this coating weight the monofilament spacer fibres were securely bonded whilst there remained some porosity in the knitted surfaces of the fabric.

On leaving the coating nip, a non-woven needle felt of thickness 0.75 mm with a modulus of 0.02 MPa and a void fraction of greater than 75% was bonded by the molten CAPA onto one surface of the 3D-knitted fabric to form the conformable zone.

The material was allowed to re-expand and cool to produce an articular zone (3D-knit) with a compressive modulus of 1.8 MPa and a void fraction of greater than 75%. The composite was then allowed to cool and stiffen.

The reinforced fabric was cut into 8 mm disc-shaped synthetic implants using a die cutter in a hydraulic press. The first surface of these implants was perforated using a fine tipped, heated probe to create permanent openings (7×1.8 mm diameter) therethrough and into the reinforced 3D-knitted fabric, hence providing an access route to the centre of the fabric. The openings did not extend through the second surface of the implant.

FIG. 4.1 illustrates a synthetic implant according to the invention comprising a first surface (4.1), a second surface (4.2), a conformable zone (4.3) comprising non-woven felt, an articular zone (4.4), comprising a 3D knit and openings (4.5) into the conformable zone providing access to the interior of the implant.

Particulate Synthesis

Partially cross-linked, sulphated carboxymethylcellulose (CMC) particulates were prepared as follows. All glassware, metal ware and partially crosslinked CMC powder (Akzo X181™) were dried in an oven (110° C.; overnight). Akzo X181™ powder (4 g), and dimethylformamide (DMF, 20 ml) were placed in a flask, and sulphur trioxide-DMF complex (18.4 g), added under an inert atmosphere. The mixture was stirred mechanically under a dry, inert atmosphere for approximately 4 hours at 50° C. After cooling, the reaction was quenched by adding of sufficient sodium bicarbonate to neutralise the excess sulphur trioxide-DMF complex (approx 20 g in minimum water). The reaction mixture was transferred to dialysis tubing and dialysed against distilled water for approximately 48 hours. The solid contents of the tubing were then collected by filtration over Buchner apparatus and washed with water. The product was dried (under reduced pressure at 45° C.) to give oval particulates with a median length of 150 μm (shortest length 25 μm; longest 500 μm).

Culture Equipment

Tube A: a 50 ml conical bottomed centrifuge tube with a 0.45 μm filter cartridge (Eppendorf 0030099176™) and a screw cap bearing a 0.21 μm filter (Fisher FDP 954 050X™). Freeze dried collagenase, (24 mg; 276 U/ml) is supplied as a powder inside the tube on top of the 4.5 mm filter.

Tube B: a standard 50 ml conical bottomed centrifuge tube, (e.g. Falcon 352074™).

Bioreactor: a tube is employed being either a 15 ml Fisherbrand conical bottomed centrifuge tube, (Fisherbrand 05-539-5™), with a screw cap bearing a 0.2 μm filter, (Falcon 3107™) or alternatively a 50 ml conical bottomed centrifuge tube, (Falcon 352074™), and a screw cap bearing a 0.2 μm filter, (Fisher FDP 954 050X™).

The base of the bioreactor is filled with a molten 4% agarose solution, (Sigma A-9045™) in DMEM, (Sigma D6429™). 2 ml agarose solution was used with the 15 ml tubes and 5 ml with the 50 ml tubes. The agar is allowed to cool and set to form a plug with the tubes held vertically. This plug is an optional feature which has the advantage of providing material with which to exchange nutrients and waste products—a function which a flat container bottom cannot perform.

Insert means, comprising both funnel means and a scaffold support chamber, turned from high density polyethylene are inserted into the bioreactor. FIG. 4.2 illustrates insert means which may be employed with the 15 ml tubular bioreactor, in which, for example: a=13.5 mm; b=7.5 mm; c=4 mm; d=3 mm (the dimensions of the insert means used in larger tubes may be scaled accordingly).

A synthetic implant manufactured as described above was inserted (with conformable, non-woven layer uppermost) into the scaffold support chamber of the insert means and the scaffold/insert means assembly slid into the bioreactor such that it rested upon the agarose layer. The particulate filler material, (partially cross-linked, sulphated CMC; 350 mg per ml of scaffold internal volume; 70 mg for the 8 mm diameter scaffolds used with the smaller tubes), was added to the incubation chamber (above the insert) and the bioreactor was capped.

Cell Isolation

DMEM (12 ml) was added to Tube A to reconstitute the collagenase. Autologous human serum, (4.8 ml) and DMEM, (2.2 ml) was added to the bioreactor to rehydrate the particulates and allow them to absorb cell attachment factors from the serum.

A 4 mm cartilage biopsy was obtained from a non-load bearing portion of the joint, sliced with a scalpel and added to Tube A. The tube was then incubated for 16-24 hours at 37° C. in a humidified atmosphere of 5% $CO_2$ (the 0.2 µm filter in the lid permits gas exchange whilst ensuring sterility). The 4.5 µm filter cartridge with the cells and a portion of the collagenase was then transferred to Tube B and centrifuged, (1000 rpm; 5 min), to separate the isolated cells from the collagenase solution.

The isolated cells were resuspended in DMEM, (1 ml) and transferred to the bioreactor.

The bioreactor was placed upon a slowly rotating mixer and incubated at 37° C. in a humidified atmosphere of 5% $CO_2$ for 7-10 days. FIG. 4.3 illustrates this phase of the method: the bioreactor (4.6) comprises insert means (4.7), within which is located a scaffold (4.8) held in the scaffold support chamber. Above the insert is the incubation chamber comprising cells suspended in DMEM (not shown) and particulates (4.9) to which the cells are to adhere. Note: the agar plug (4.10) is shown below the synthetic implant.

At the end of the culture period, the bioreactor was centrifuged, (500 rpm; 5 min), aggregating the cell-covered particulate material into the void spaces of the synthetic implant to generate a hybrid implant (4.11), shown in FIG. 4.4.

Implantation

The base of the implant site was mechanically debrided to expose, abrade and recess the subchondral bone, whilst the cartilaginous periphery of the defect is cut back to healthy cartilage using sharp instruments. The medium was then aspirated from the bioreactor, the insert means and hybrid implant lifted out, the hybrid implant removed from the insert means and inverted. A periosteal flap was harvested from the tibia and sutured onto the robust upper surface of the articular zone (reinforced 3D knit) to provide a source of chondroprogenitor cells and a more lubricious articular surface. The hybrid implant was then press fitted into the defect site, flush with the surrounding cartilage. It was secured in position with sutures and bioresorbable pegs.

Example 4.2

Sulphated Intrasite

Synthesis and Sterilisation of Sulphated Intrasite Gel (SX-CMC Gel)

Methods

Intrasite powder (2 g; oven dried, 110° C.; 16 hours; Smith and Nephew), dimethylformamide (DMF, 10 ml; Aldrich) and sulphur trioxide-pyridine complex (9.2 g; Aldrich), were stirred mechanically for 4 hours at 50° C. The reaction mixture was cooled and sodium bicarbonate (approx 10 g in minimum water) added to neutralise the excess sulphur trioxide-pyridine complex. The products were dialysed against distilled water, (2-7 days), freeze-dried and stored at 4° C. The material was resuspended in PBS, (100 mg; 6.5 mg/ml), and sterilised by autoclaving at 121° C. for 15 mins.

Results

The reaction typically yielded 1 g sulphated material. Macroscopically the freeze-dried sulphated Intrasite was a flocculent, somewhat fibrous white material. It rehydrated readily in PBS to form a translucent suspension. The particles sedimented under gravity to produce a layer of gel and a clear supernatant. The microscopic appearance of the material is shown in FIG. 4.5.

Analysis of Sulphated Intrasite

Methods.

The chemical nature of the modified polymer was investigated by Raman spectroscopy, (Renishaw Raman microscope) or infrared spectroscopy, (Perkin-Elmer 1750 or Mattson Galaxy FTIRs) and the resulting spectra compared against published reference spectra. Sulphur content was determined by elemental analysis at an accredited laboratory, (Butterworth). The particle size distribution was determined using a Coulter Particle size analyser.

Alcian Blue (critical electrolyte concentration stain) was used to visualise the derivatised polymer. Alcian blue, (0.05 g in 0.2M acetate buffer pH 5.8 plus $MgCl_2$ at 0.06M, 0.3M, 0.5M, 0.7M or 0.9M) was incubated with the polymer for 16 hours at room temperature, the samples washed in PBS and viewed both macroscopically and by phase contrast microscopy.

Results

FIG. 4.6 shows representative spectra for the modified and unmodified materials. Sulphation was confirmed by the appearance of a distinct peak at 1280 µm and by binding of alcian blue to the modified material in the presence of 0.9M $MgCl_2$ compared to <0.3 M for the unmodified material. Particle size analysis suggested that 80% of the material consisted of particles between 162 and 923 µm diameter, although this figure may have been artificially increased by particle clumping. Alcian blue CEC showed that whereas the unmodified Intrasite bound alcian blue at $MgCl_2$ concentrations below 0.3M, (consistent with a weakly anionic material), the sulphated Intrasite bound alcian blue at all $MgCl_2$ concentrations used including 0.9M. This finding indicates that the modified material is very strongly anionic, consistent with successful sulphation.

Routine Analysis of Sulphated Intrasite

Method

The polyanionic nature of the autoclaved sulphated Intrasite was routinely confirmed by diluting 100 µl material with PBS, (900 µl) and adding the histological dye Safranin O (0.1%; 20 µl; 30 mins). The mixture was diluted to 20 ml with PBS, centrifuged, (2500 rpm; 5 min), the supernatant discarded and the dyed material resuspended in 20 ml PBS.

Results

Polyanionic sulphated Intrasite stained dark orange. Unmodified or expired material stained pale pink.

Adsorption of Cell Attachment Proteins to Sulphated Intrasite

Method

The adsorption of cell attachment proteins onto sulphated Intrasite particles was confirmed by immunocytochemistry. sulphated Intrasite, (1 ml; 6.5 mg/ml in PBS), was washed three times in PBS, (10 ml; centrifuged 2500 rpm; 5 min), and incubated (16 hours; 4° C.; with constant agitation), in either (i) 60 µg/ml solutions of purified/recombinant cell adhesion factors, (plasma fibronectin, (Sigma), cellular fibronectin, (Sigma), fibronectin-EDA, (affinity purified), collagen VI (Chemicon International), (all in 2 ml in PBS)), or (ii) 60% foetal calf serum in PBS, (Helena Biosciences). BSA (60 µg/ml in 2 ml PBS; Sigma) was used as a control.

The concentration of fibronectin in serum is approximately 100 µg/ml. Consequently a 60% dilution gives approximately 60 µg/ml fibronectin.

The coated material was washed three times with PBS and blocked by incubating in BSA (3% w/v in PBS; 1 hour; room temperature Sigma). Gels were then washed three times and incubated with primary antibody raised against the relevant binding material in 1 ml PBS for 1 hour at 37° C. The antibodies used were mouse anti-fibronectin-EDA antibody, (50 μg/ml; Oxford Biotechnologies), rabbit anti-fibronectin antibody (50 μg/ml; Dako), rabbit anti-vitronectin antibody (50 μg/ml; Biogenesis), and Rabbit anti-Collagen VI antibody (20 μg/ml; Abcam). Non-immune rabbit IgG fraction (50 μg/ml; Dako) was used as a control.

Samples were then washed three times in PBS. To visualise the rabbit antibody labelled samples, specimens were incubated with FITC conjugated swine anti-rabbit secondary antibody (1:100 dilution in PBS; 1 hour at 37° C.; Dako). For detection of mouse anti-fibronectin-EDA antibodies a biotinylated rabbit anti-mouse secondary antibody was used (Dako), followed by washing, (three times in PBS) and detection using a streptavidin-FITC conjugate (Amersham Pharmacia Biotech), at a 1:100 dilution in PBS for 1 hour at 37° C. Gel was then washed 3× with PBS. Small aliquots were then transferred onto glass slides, coverslipped and viewed using the Leica DM-RE confocal microscope using an ArKr laser exciting at 488 nm.

Results

All the cell adhesion factors tested could be demonstrated to bind to the sulphated Intrasite gel. FIG. 4.7 illustrates plasma fibronectin, cellular fibronectin and fibronectin-EDA binding to sulphated Intrasite. FIG. 4.8 illustrates collagen VI binding. FIG. 4.9 illustrates fibronectin and vitronectin binding following absorption from FCS. No staining occurred in control gel coated with BSA and gels incubated with non-immune rabbit IgG.

Cell Attachment to Sulphated Intrasite and Unmodified Intrasite

Method

Serum-ee DMEM was prepared by mixing DMEM, (500 ml), penicillin and streptomycin (Sigma; 5 ml); non essential amino acids, (Sigma 5 ml) and L-glutamine, (Sigma; 5 ml).

Sulphated and unmodified Intrasite was re-suspended in PBS, (6.5 mg/ml) and sterilised by autoclaving at 121° C. for 15 mins. The autoclaved material was washed three times with PBS, (centrifuged 2500 rpm; 5 min), and resuspended in either PBS or 60% foetal calf serum (in PBS; Helena Biosciences) for 2 hours at 4° C.

The samples were then washed twice in PBS and resuspended in serum-free DMEM.

A confluent T175 flask of bone marrow stromal cells was rinsed in PBS and trypsinised, (Sigma). Suspended bone marrow stromal cells, (750 k cells), PBS or FCS pre-treated sulphated Intrasite or untreated Intrasite were mixed in 20 ml of serum-free DMEM and the cultures incubated at 37° C. in a humidified atmosphere of 5% $CO_2$ for 1 hour to 14 days. To visualise any viable adherent cells, the cultures were treated with calcein AM (0.6 μl/ml; 1 mg/ml; 90 mins; Molecular Probes) and viewed using a Leica confocal microscope.

Results

Very few cells adhered to unmodified Intrasite gel, irrespective of whether it had been pre-treated with PBS or foetal calf serum (60%). Similarly, few cells adhered to sulphated Intrasite that had been pre-treated with PBS alone. In contrast, cells adhered readily to 60% FCS pre-treated sulphated Intrasite and spread upon its surface. FIG. 4.10 compares cell attachment to FCS pre-treated, unmodified Intrasite with cell attachment to FCS pre-treated sulphated Intrasite.

Conclusion

It was concluded that cell adhesion factors absorbed from serum onto the surface of the sulphated Intrasite could support cell attachment to this biomaterial.

Attachment of Antibodies to Sulphated Intrasite Using of p-toluenesulphonylchloride (Formerly Known as 'p-tosyl chloride')

Different cell types are characterized by specific sets of cell surface molecules, (e.g. signal receptors, enzymes, structural components or surface bound signal molecules). Specific antibodies raised against these surface markers may be used to selectively bind one cell type and isolate it from a mixed population. The following methods describe how anti-Notch-1 antibody or anti-integrin $β_1$, (antibodies that recognize epitopes expressed by superficial zone chondroprogenitor cells), maybe bound to sulphated Intrasite to create a chondroprogenitor cell binding material. The method is not specific to these antibodies and could be used to attach different antibodies to the particulate biomaterial.

Sulphated Intrasite™ was suspended in dry pyridine, (35% w/w), mixed with a slight molar excess of tosyl chloride, (10% w/w) and stirred for 16 hours at 8° C. under an inert atmosphere. The activated gel was collected by filtration, washed thoroughly and a homogeneous suspension prepared by vortexing the material for 1-2 minutes. Anti-Notch-1 antibody, (5 μg; Santa Cruz) or anti-$β_1$ integrin, was added and the suspension vortexed for 1-2 minutes. The suspension was incubated for 10 minutes at 37° C. with slow tilt rotation before BSA, (0.50/w/v final concentration) was added to terminate the reaction. The reaction mixture was then returned to the rotator and incubated for a further 16-24 hours at 37° C.

Wash the antibody derivatised sulphated Intrasite™ was washed twice in acetate buffer, (0.1M; pH 4.0; 5 minutes at 4° C.) and once in PBS containing 0.1% BSA for 4 hours at 37° C. The material was washed in acetate buffer, (5 minutes; 4° C.), and stored at 4° C.

Use of Alternative Polyanionic, Polysaccharide Materials to Bind Cell Attachment Factors and Support Cell Adhesion Heparin sepharose beads (Pharmacia) consist of a cross-linked polysaccharide material, 'Sepharose', (that does not bind cells or proteins), covalently linked to a biodegradable polyanionic material, heparin. Such beads are widely used in biochemistry to purify proteins from mixtures of biological molecules. They are not generally used in cell culture. It was hypothesised that heparin sepharose beads would not bind cells directly, but that they would bind cell adhesion factors and, once coated with cell adhesion factors, would support cell attachment.

Method

Heparin sepharose beads, (200 mg; Pharmacia) were rehydrated with PBS, (40 ml; 15 min at 37° C.), washed twice with PBS and sterilised by autoclaving at 110° C. for 30 minutes. The heparin sepharose beads, (10 mg) were pre-treated with either 20 mg/ml BSA, 80 mg/ml BSA, 10% FCS, 40% FCS or PBS alone (20 ml total volume). The beads were allowed to sediment for 15 minutes, 15 ml supernatant removed and replaced with $400 \times 10^3$ bone marrow stromal cells in serum-free DMEM (15 ml). The cultures were mixed and incubated at 37° C. for 30 minutes to 3 hours. Samples (100 μl) were transferred to the wells of a non-tissue culture treated 96 well plate (Greiner) and viewed with an inverted phase contrast microscope.

The experiment was repeated using collagen IV, (2.5 and 10 μg/ml) and foetal calf serum (40%) to coat the heparin sepharose beads (25 mg). Quadruplicate samples of the cell seeded, coated beads were viewed by phase contrast microscopy after a 6 hour incubation at 37° C. in a humidified atmosphere of 5% $CO_2$ and the number of adherent cells per bead counted.

In addition, samples of bone marrow stromal cell seeded, FCS pre-treated heparin sepharose beads were pre-pared as above and cultured in DMEM/10% FCS for 1-22 days and viewed by phase contrast microscopy.

Results and Discussion

Little or no cell adhesion was observed with any of the BSA or FCS pre-treated samples of heparin Sepharose beads after 30 minutes. After 3 hours however, cell adhesion and cell spreading had occurred on the 40% FCS treated heparin sepharose beads but not upon either of the BSA treated samples, the 10% FCS pre-treated samples or the samples pre-treated with PBS alone. Some cell clumping was observed amongst the unattached cells, indicating that although they had not adhered to the BSA coated beads, the 10% FCS coated beads or the beads exposed to PBS alone, they were able to adhere to each other.

Counting the number of cells attached to PBS, collagen IV and FCS pre-treated heparin sepharose beads showed that the number of bound cells per bead was (mean±SEM): PBS pre-treated 0.51±0.09 cells per bead; Collagen IV (2.5 µg/ml) pre-treated 3.45±0.19 cells per bead ($p<0.001$); Collagen IV (10 µg/ml) pre-treated 3.23±0.22 cells per bead ($p<0.001$); and 40% FCS pre-treated 3.17±0.42 cells per bead ($p<0.001$). It was concluded that heparin sepharose beads could absorb collagen IV or cell adhesion molecules present in FCS and, thereafter, support cell adhesion. This was not a non-specific property of proteins because BSA could not coat the beads nor support cell adhesion.

If samples of cells and FCS pre-treated heparin sepharose beads were cultured for 6-10 days they formed macroscopic aggregates of cells, beads and extracellular matrix components. If the cell-seeded aggregates were cultured for longer periods, (i.e. 14-22 days), it was observed that the cell/material aggregates shrank and expelled the beads to leave small cell clusters. Histological staining with Safranin O showed that this occurred when the heparin coating degraded, presumably because this exposed the non-cell adherent sepharose and released the cell attachment factors, thereby terminating cell attachment to the beads. It was decided that whilst this observation suggested a route to a 'switchable' cell-binding material, it was not an ideal property for a cartilage implant. It was concluded that a slowly degrading or non-biodegradable polysaccharide material with covalently linked anionic functional groups would be preferable to heparin sepharose.

Dextran beaded sulphated beads (Sigma) are a spherical, cross-linked polysaccharide particulate materials with covalently bound anionic groups. The material was coated with cell adhesion factors and its ability to support cell attachment and growth assessed.

Dextran sulphate beads, (667 mg; Sigma), were rehydrated in 26.7 ml PBS for 30 minutes, autoclaved, (121° C.; 15 minutes) and allowed to cool. The sterile material was washed three times with PBS and then incubated in either 60% FCS, (in 66.7 ml total) or PBS, (66.7 ml) for 2 hours at 37° C. on the Denley mixer. The beads were allowed to settle and washed three times in serum free DMEM to produce ~17 ml of 40 mg/ml 60% FCS pre-treated dextran sulphate beads.

60% FCS pre-treated dextran sulphate beads, (30 mg) or PBS pre-treated dextran sulphate beads (30 mg) were mixed with bone marrow stromal cells, (200 k cells), in DMEM supplemented with Hams F-12 (10%), FCS (10%), and ascorbate 2 phosphate, (50 µg/ml; 5 ml). Cultures were incubated at 37° C. for 0-22 days.

Results

Bone marrow stromal cells adhered readily to the surfaces of 60% FCS pre-treated dextran sulphate beads but did not attach to the surfaces of PBS pre-treated dextran sulphate beads.

The invention claimed is:

1. An implant, artificial or semi-artificial at implantation, for implantation at an articular cartilage and osteochondral defect site in a human comprising:
a manufactured biocompatible scaffold, the scaffold comprising at least a first surface and a second surface;
the first surface shaped to press-fit into the defect site to create an interface between the first surface and a bone-cartilage region of the defect site;
the second surface shaped to press-fit into the defect site to create an interface between the second surface and an articular cartilage region of the defect site;
a distance $d_1$ between the first and second surfaces; and
depth $d_2$ from the second surface, wherein $d_2$ comprises a greater concentration of articular chondroprogenitor cells than the concentration of these cells in the remaining depth of the implant and wherein $d_2/d_1<1$.

2. The implant of claim 1, in which $d_2/d_1<0.5$.

3. The implant of claim 1, in which $d_2/d_1<0.3$.

4. The implant of claim 1, in which $d2/di<0.2$.

5. The implant of claim 1, further comprising a chondroprogenitor binding material.

6. The implant of claim 5, wherein the chondroprogenitor binding material is selected from the group consisting of fibronectin, anti-Notch antibody, and anti-integrin 131 antibody.

7. The implant of claim 6, wherein the chondroprogenitor binding material is fibronectin selected from the group consisting of plasma fibronectin, cellular fibronectin, and fibronectin-EDA.

8. The implant of claim 1, wherein the implant comprises a plurality of layers.

9. The implant of claim 1, further comprising bioresorbable materials.

10. The implant of claim 1, further comprising non-bioresorbable materials.

11. The implant of claim 1, further comprising a reinforcing component.

12. The implant of claim 1, wherein the scaffold is a poly-anionic particulate.

13. The implant of claim 12, wherein the poly-anionic particulate is sulphated carboxymethylcellulose.

14. The implant of claim 1, in which the articular chondroprogenitor cells are mesenchymal precursor cells.

15. The implant of claim 1, in which the articular chondroprogenitor cells are autologous with the human with the defect site.

16. The implant of claim 1, in which the articular chondroprogenitor cells are allogenic with the human with the defect site.

17. The implant of 1, wherein the implant is seeded with the articular chondroprogenitor cells and wherein the articular chondroprogenitor cells comprise colony forming ability in vitro, and expressing a cell marker bound by a chondroprogenitor binding material selected from the group consisting of type IV collagen, anti-Notch, antibody, anti-integrin $\beta_i$ antibody cellular fibronectin, plasma, fibronectin, fibronectin extra domain A (fibronectin-EDA), and the EDA domain of fibronectin-EDA on its own.

* * * * *